(12) United States Patent
Sigurdsson

(10) Patent No.: US 10,358,503 B2
(45) Date of Patent: Jul. 23, 2019

(54) ANTIBODY-BASED MOLECULES SELECTIVE FOR THE {P}SER404 EPITOPE OF TAU AND THEIR USES IN THE DIAGNOSIS AND TREATMENT OF TAUOPATHY

(71) Applicant: New York University, New York, NY (US)

(72) Inventor: Einar Sigurdsson, Scarsdale, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/750,982

(22) PCT Filed: Aug. 11, 2016

(86) PCT No.: PCT/US2016/046520
§ 371 (c)(1),
(2) Date: Jul. 19, 2018

(87) PCT Pub. No.: WO2017/027691
PCT Pub. Date: Feb. 16, 2017

(65) Prior Publication Data
US 2018/0312608 A1 Nov. 1, 2018

Related U.S. Application Data

(60) Provisional application No. 62/204,711, filed on Aug. 13, 2015.

(51) Int. Cl.
| | |
|---|---|
| *A61K 9/00* | (2006.01) |
| *A61K 39/00* | (2006.01) |
| *A61K 49/00* | (2006.01) |
| *A61P 25/28* | (2006.01) |
| *C07K 16/18* | (2006.01) |
| *C07K 16/44* | (2006.01) |
| *G01N 33/58* | (2006.01) |
| *G01N 33/68* | (2006.01) |

(52) U.S. Cl.
CPC ........... *C07K 16/44* (2013.01); *A61K 9/0019* (2013.01); *A61K 49/0058* (2013.01); *A61P 25/28* (2018.01); *C07K 16/18* (2013.01); *G01N 33/58* (2013.01); *G01N 33/6896* (2013.01); *A61K 2039/505* (2013.01); *C07K 2317/24* (2013.01); *C07K 2317/32* (2013.01); *C07K 2317/56* (2013.01); *C07K 2317/565* (2013.01); *C07K 2317/622* (2013.01); *C07K 2317/70* (2013.01); *C07K 2317/76* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS

| | | | | |
|---|---|---|---|---|
| 2010/0316564 A1* | 12/2010 | Sigurdsson | ........ | A61K 39/0005 424/1.49 |
| 2014/0302046 A1 | 10/2014 | Sigurdsson | | |
| 2015/0266947 A1* | 9/2015 | Sierks | ................ | G01N 33/6896 424/135.1 |
| 2017/0355756 A1* | 12/2017 | Julien | .................... | C07K 16/18 |

FOREIGN PATENT DOCUMENTS

| | | | |
|---|---|---|---|
| WO | WO 2008068048 | * | 6/2008 |
| WO | WO 2012/045882 | | 4/2012 |
| WO | WO 2016/007414 | | 1/2016 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
International Search Report PCT/US2016/046520 (WO 2017/027691) (dated 2016) (4 pages).
Written Opinion of the International Searching Authority PCT/US2016/046520 (WO 2017/027691) (dated 2016) (5 pages).
Extended European Search Report EP 16835899.2 (dated Mar. 21, 2019) (9 pages).
Gu, J. et al. (2013) "*Two Novel Tau Antibodies Targeting the 396/404 Region are Primarily Taken Up by Neurons and Reduce Tau Protein Pathology*," J. Biol. Chem. 288(46):33081-33095.
Krishnaswamy, S., et al. (2014) "*Antibody-Derived in Vivo Imaging of Tau Pathology*," J. Neurosci. 34(50):16835-16850.

* cited by examiner

*Primary Examiner* — Adam Weidner
(74) *Attorney, Agent, or Firm* — Jeffrey I. Auerbach; AuerbachSchrot LLC

(57) ABSTRACT

The present invention relates to antibody-based molecules (including single domain antibody fragment, scFv molecules, antibodies, antibody fragments, diabodies, and the epitope-binding domains thereof) that are capable of immunospecifically and selectively binding to the {P}Ser404 Epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules of the present invention have particular utility as diagnostic markers for, Alzheimer's disease and related tauopathies and as pharmaceutical compositions for the treatment of such conditions.

21 Claims, 18 Drawing Sheets
Specification includes a Sequence Listing.

Panel A: Antibody 4E6G7 CSF Maze Pre- vs. Post-Treatment

Panel B: Antibody 6B2G12 CSF Maze Pre- vs. Post-Treatment

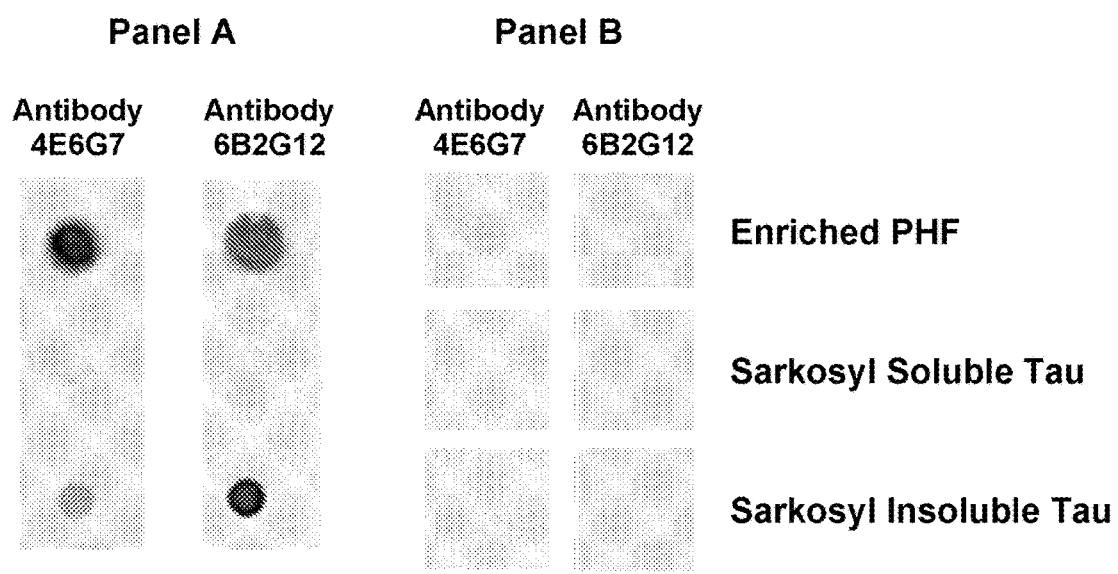
Figure 16, Panels A and B

Panel C
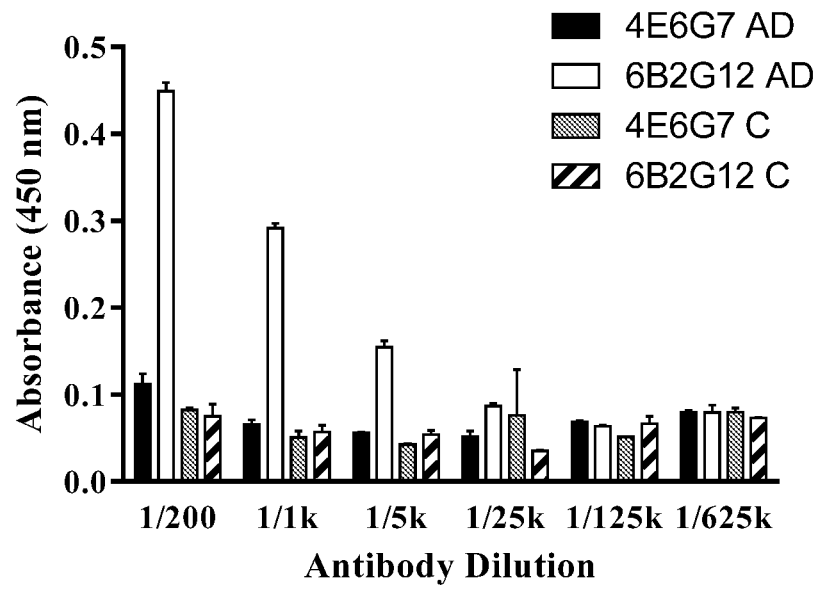
Panel D
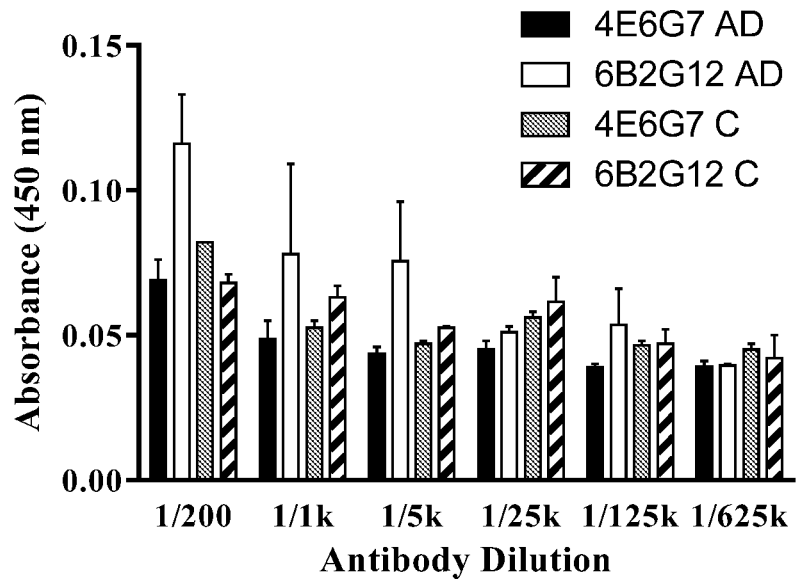
Figure 16, Panels C and D

Panel E
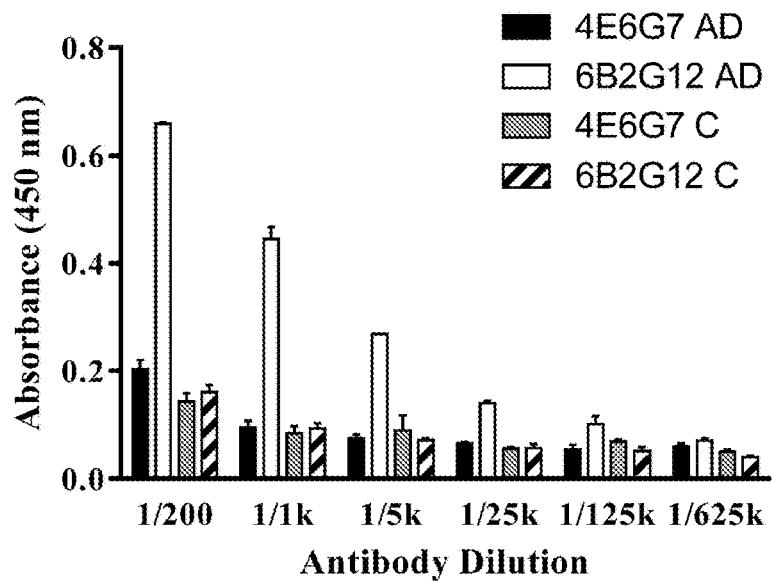
Panel F
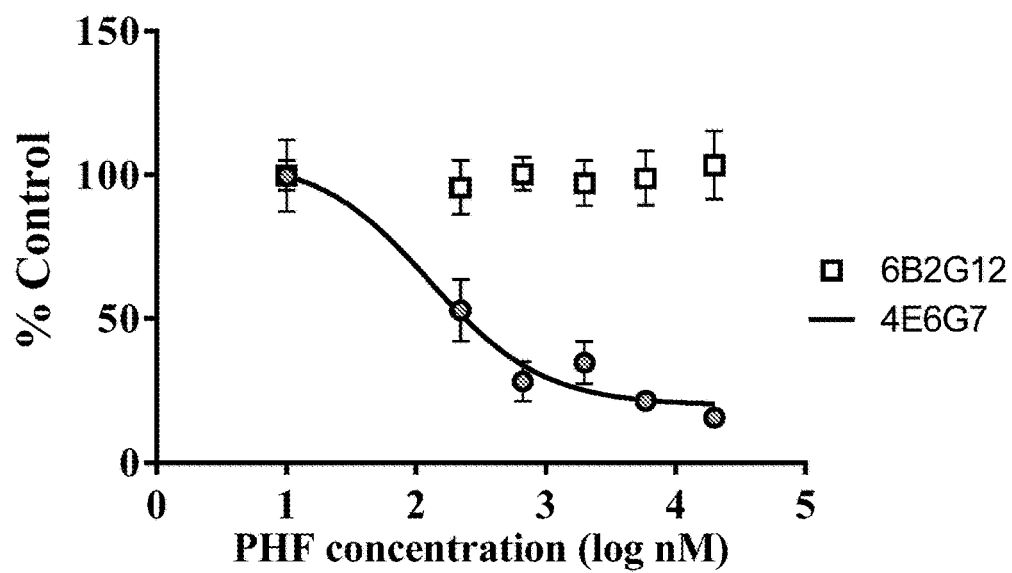
Figure 16, Panels E and F

SEQUENCE LISTING

```
<160> NUMBER OF SEQ ID NOS: 31

<210> SEQ ID NO 1
<211> LENGTH: 441
<212> TYPE: PRT
<213> ORGANISM: Homo sapiens
<220> FEATURE:
<221> NAME/KEY: MISC_FEATURE
<222> LOCATION: (1)..(441)
<223> OTHER INFORMATION: Human Tau residues

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
```

```
                      275                 280                 285
Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 15
<212> TYPE: PRT
<213> ORGANISM: Artificial Sequence
<220> FEATURE:
<223> OTHER INFORMATION: Glycine-Containing Linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Linker

<400> SEQUENCE: 3

Gly Ser Thr Ser Gly Ser Gly Lys Pro Gly Ser Gly Glu Gly Ser Thr
1               5                   10                  15

Lys Gly

<210> SEQ ID NO 4
<211> LENGTH: 18
<212> TYPE: PRT
<213> ORGANISM: Artificial Sequence
<220> FEATURE:
<223> OTHER INFORMATION: Preferred Linker

<400> SEQUENCE: 4

Ser Ser Gly Gly Gly Gly Ser Gly Gly Gly Gly Gly Gly Ser Ser Arg
1               5                   10                  15

Ser Ser

<210> SEQ ID NO 5
<211> LENGTH: 6
<212> TYPE: PRT
```

```
<213> ORGANISM: Artificial Sequence
<220> FEATURE:
<223> OTHER INFORMATION: His-Tag

<400> SEQUENCE: 5

His His His His His His
1               5

<210> SEQ ID NO 6
<211> LENGTH: 12
<212> TYPE: PRT
<213> ORGANISM: Artificial Sequence
<220> FEATURE:
<223> OTHER INFORMATION: HA-Tag

<400> SEQUENCE: 6

Gly Ala Tyr Pro Tyr Asp Val Pro Asp Tyr Ala Ser
1               5                   10

<210> SEQ ID NO 7
<211> LENGTH: 23
<212> TYPE: PRT
<213> ORGANISM: Artificial Sequence
<220> FEATURE:
<223> OTHER INFORMATION: Immunogen containing the
Ser404    Epitope
<220> FEATURE:
<221> NAME/KEY: MOD_RES
<222> LOCATION: (11)..(11)
<223> OTHER INFORMATION: PHOSPHORYLATION (Residue is Phosphoserine)
<220> FEATURE:
<221> NAME/KEY: MOD_RES
<222> LOCATION: (19)..(19)
<223> OTHER INFORMATION: PHOSPHORYLATION (Residue is Phosphoserine)

<400> SEQUENCE: 7

Thr Asp His Gly Ala Glu Ile Val Tyr Lys Ser Pro Val Val Ser Gly
1               5                   10                  15

Asp Thr Ser Pro Arg His Leu
            20

<210> SEQ ID NO 8
<211> LENGTH: 23
<212> TYPE: PRT
<213> ORGANISM: Artificial Sequence
<220> FEATURE:
<223> OTHER INFORMATION: Immunogen containing the
Ser404    Epitope
<220> FEATURE:
<221> NAME/KEY: MOD_RES
<222> LOCATION: (11)..(11)
<223> OTHER INFORMATION: PHOSPHORYLATION (Residue is Phosphoserine)
<220> FEATURE:
<221> NAME/KEY: MOD_RES
<222> LOCATION: (19)..(19)
<223> OTHER INFORMATION: PHOSPHORYLATION (Residue is Phosphoserine)

<400> SEQUENCE: 8

Thr Asp His Gly Ala Glu Ile Val Tyr Lys Ser Pro Val Val Ser Gly
1               5                   10                  15

Asp Thr Ser Pro Arg His Leu
            20

<210> SEQ ID NO 9
<211> LENGTH: 108
<212> TYPE: PRT
<213> ORGANISM: Mus musculus
<220> FEATURE:
<221> NAME/KEY: MISC_FEATURE
```

```
<222> LOCATION: (1)..(108)
<223> OTHER INFORMATION: Light Chain Variable Domain of Antibody 4E6G7

<400> SEQUENCE: 9

Asp Ile Gln Met Asn Gln Ser Pro Ser Ser Leu Ser Ala Ser Leu Gly
1               5                   10                  15

Asp Thr Ile Thr Ile Ser Cys His Ala Ser Gln Asn Ile Asn Val Trp
                20                  25                  30

Leu Ser Trp Tyr Gln Gln Lys Pro Gly Asn Ile Pro Lys Leu Leu Ile
            35                  40                  45

Phe Glu Ala Ser Thr Leu Tyr Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg
            100                 105

<210> SEQ ID NO 10
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDR1 of Light Chain of Antibody 4E6G7

<400> SEQUENCE: 10

His Ala Ser Gln Asn Ile Asn Val Trp Leu Ser
1               5                   10

<210> SEQ ID NO 11
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR2 of Light Chain of Antibody 4E6G7

<400> SEQUENCE: 11

Glu Ala Ser Thr Leu Tyr Thr
1               5

<210> SEQ ID NO 12
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR3 of Light Chain of Antibody 4E6G7

<400> SEQUENCE: 12

Gln Gln Gly Gln Ser Tyr Pro Trp Thr
1               5

<210> SEQ ID NO 13
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
```

<223> OTHER INFORMATION: Heavy Chain Variable Domain of Antibody 4E6G7

<400> SEQUENCE: 13

Val Gln Leu Gln Gln Ser Gly Ala Glu Leu Val Gln Pro Gly Ala Ser
1               5                   10                  15

Val Lys Leu Ser Cys Thr Ala Ser Gly Phe Asn Ile Lys Asp Thr Ser
            20                  25                  30

Met His Trp Val Arg Gln Arg Pro Glu Gln Gly Leu Glu Trp Ile Gly
        35                  40                  45

Arg Ile Ala Pro Ala Asn Gly Asn Thr Lys Tyr Asp Pro Lys Phe Gln
    50                  55                  60

Gly Lys Ala Thr Ile Thr Thr Asp Thr Ser Ser Asn Thr Ala Tyr Leu
65                  70                  75                  80

Gln Leu Ser Ser Leu Thr Ser Glu Asp Thr Ala Val Tyr Tyr Cys Ser
                85                  90                  95

Gly Ser Gly Asn Tyr Asp Trp Gly Gln Gly Thr Thr Leu Thr Val Ser
            100                 105                 110

<210> SEQ ID NO 14
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: CDR1 of Heavy Chain of Antibody 4E6G7

<400> SEQUENCE: 14

Gly Phe Asn Ile Lys Asp Thr Ser Met His
1               5                   10

<210> SEQ ID NO 15
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDR2 of Heavy Chain of Antibody 4E6G7

<400> SEQUENCE: 15

Arg Ile Ala Pro Ala Asn Gly Asn Thr Lys Tyr Asp Pro Lys Phe Gln
1               5                   10                  15

Gly

<210> SEQ ID NO 16
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDR3 of Heavy Chain of Antibody 4E6G7

<400> SEQUENCE: 16

Ser Gly Asn Tyr Asp
1               5

<210> SEQ ID NO 17
<211> LENGTH: 238
<212> TYPE: PRT
<213> ORGANISM: Artificial Sequence
<220> FEATURE:
<223> OTHER INFORMATION: Antibody 4E6G7 scFv Fusion Protein

```
<220> FEATURE:
<221> NAME/KEY: MISC_FEATURE
<222> LOCATION: (1)..(108)
<223> OTHER INFORMATION: Light Chain Variable Domain of Antibody 4E6G7
<220> FEATURE:
<221> NAME/KEY: MISC_FEATURE
<222> LOCATION: (109)..(126)
<223> OTHER INFORMATION: Linker
<220> FEATURE:
<221> NAME/KEY: MISC_FEATURE
<222> LOCATION: (127)..(238)
<223> OTHER INFORMATION: Heavy Chain Variable Domain of Antibody 4E6G7

<400> SEQUENCE: 17
```

Asp Ile Gln Met Asn Gln Ser Pro Ser Ser Leu Ser Ala Ser Leu Gly
1               5                   10                  15

Asp Thr Ile Thr Ile Ser Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Phe Glu Ala Ser Thr Leu Tyr Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg Ser Ser Gly Gly
            100                 105                 110

Gly Gly Ser Gly Gly Gly Gly Ser Ser Arg Ser Ser Val Gln
        115                 120                 125

Leu Gln Gln Ser Gly Ala Glu Leu Val Gln Pro Gly Ala Ser Val Lys
    130                 135                 140

Leu Ser Cys Thr Ala Ser Gly Phe Asn Ile Lys Asp Thr Ser Met His
145                 150                 155                 160

Trp Val Arg Gln Arg Pro Glu Gln Gly Leu Glu Trp Ile Gly Arg Ile
                165                 170                 175

Ala Pro Ala Asn Gly Asn Thr Lys Tyr Asp Pro Lys Phe Gln Gly Lys
            180                 185                 190

Ala Thr Ile Thr Thr Asp Thr Ser Asn Thr Ala Tyr Leu Gln Leu
        195                 200                 205

Ser Ser Leu Thr Ser Glu Asp Thr Ala Val Tyr Tyr Cys Ser Gly Ser
    210                 215                 220

Gly Asn Tyr Asp Trp Gly Gln Gly Thr Thr Leu Thr Val Ser
225                 230                 235

```
<210> SEQ ID NO 18
<211> LENGTH: 28
<212> TYPE: PRT
<213> ORGANISM: Artificial Sequence
<220> FEATURE:
<223> OTHER INFORMATION: N-Terminal Leader Peptide

<400> SEQUENCE: 18
```

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala
            20                  25

```
<210> SEQ ID NO 19
<211> LENGTH: 15
```

```
<212> TYPE: PRT
<213> ORGANISM: Artificial Sequence
<220> FEATURE:
<223> OTHER INFORMATION: C-Terminal Peptide

<400> SEQUENCE: 19

Ala Lys Thr Thr Pro Pro Ser Val Thr Ser Gly Gln Ala Gly Gln
1               5                   10                  15

<210> SEQ ID NO 20
<211> LENGTH: 33
<212> TYPE: PRT
<213> ORGANISM: Artificial Sequence
<220> FEATURE:
<223> OTHER INFORMATION: C-Terminal Peptide

<400> SEQUENCE: 20

Ala Lys Thr Thr Pro Pro Ser Val Thr Ser Gly Gln Ala Gly Gln His
1               5                   10                  15

His His His His His Gly Ala Tyr Pro Tyr Asp Val Pro Asp Tyr Ala
            20                  25                  30

Ser

<210> SEQ ID NO 21
<211> LENGTH: 266
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(28)
<223> OTHER INFORMATION: N-Terminal Leader Peptide (SEQ ID NO:18)
<220> FEATURE:
<221> NAME/KEY: MISC_FEATURE
<222> LOCATION: (29)..(266)
<223> OTHER INFORMATION: Antibody 4E6G7 scFv Fusion Protein (SEQ ID NO:
      17)

<400> SEQUENCE: 21

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Ile Gln Met
            20                  25                  30

Asn Gln Ser Pro Ser Ser Leu Ser Ala Ser Leu Gly Asp Thr Ile Thr
        35                  40                  45

Ile Ser Cys His Ala Ser Gln Asn Ile Asn Val Trp Leu Ser Trp Tyr
    50                  55                  60

Gln Gln Lys Pro Gly Asn Ile Pro Lys Leu Leu Ile Phe Glu Ala Ser
65                  70                  75                  80

Thr Leu Tyr Thr Gly Val Pro Ser Arg Phe Ser Gly Ser Gly Ser Gly
                85                  90                  95

Thr Gly Phe Thr Leu Thr Ile Ser Ser Leu Gln Pro Glu Asp Ile Ala
            100                 105                 110

Thr Tyr Tyr Cys Gln Gln Gly Gln Ser Tyr Pro Trp Thr Phe Gly Gly
        115                 120                 125

Gly Thr Lys Leu Glu Ile Lys Arg Ser Ser Gly Gly Gly Gly Ser Gly
    130                 135                 140

Gly Gly Gly Gly Ser Ser Arg Ser Ser Val Gln Leu Gln Gln Ser
145                 150                 155                 160

Gly Ala Glu Leu Val Gln Pro Gly Ala Ser Val Lys Leu Ser Cys Thr
                165                 170                 175
```

```
Ala Ser Gly Phe Asn Ile Lys Asp Thr Ser Met His Trp Val Arg Gln
            180                 185                 190

Arg Pro Glu Gln Gly Leu Glu Trp Ile Gly Arg Ile Ala Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Ser Asn Thr Ala Tyr Leu Gln Leu Ser Ser Leu Thr
225                 230                 235                 240

Ser Glu Asp Thr Ala Val Tyr Tyr Cys Ser Gly Ser Gly Asn Tyr Asp
                245                 250                 255

Trp Gly Gln Gly Thr Thr Leu Thr Val Ser
                260                 265

<210> SEQ ID NO 22
<211> LENGTH: 253
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(238)
<223> OTHER INFORMATION: Antibody 4E6G7 scFv Fusion Protein (SEQ ID NO:
      17)
<220> FEATURE:
<221> NAME/KEY: MISC_FEATURE
<222> LOCATION: (239)..(253)
<223> OTHER INFORMATION: C-Terminal Peptide (SEQ ID NO:19)

<400> SEQUENCE: 22

Asp Ile Gln Met Asn Gln Ser Pro Ser Ser Leu Ser Ala Ser Leu Gly
1               5                   10                  15

Asp Thr Ile Thr Ile Ser Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Phe Glu Ala Ser Thr Leu Tyr Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg Ser Ser Gly Gly
            100                 105                 110

Gly Gly Ser Gly Gly Gly Gly Gly Ser Ser Arg Ser Ser Val Gln
        115                 120                 125

Leu Gln Gln Ser Gly Ala Glu Leu Val Gln Pro Gly Ala Ser Val Lys
    130                 135                 140

Leu Ser Cys Thr Ala Ser Gly Phe Asn Ile Lys Asp Thr Ser Met His
145                 150                 155                 160

Trp Val Arg Gln Arg Pro Glu Gln Gly Leu Glu Trp Ile Gly Arg Ile
                165                 170                 175

Ala Pro Ala Asn Gly Asn Thr Lys Tyr Asp Pro Lys Phe Gln Gly Lys
            180                 185                 190

Ala Thr Ile Thr Thr Asp Thr Ser Ser Asn Thr Ala Tyr Leu Gln Leu
        195                 200                 205

Ser Ser Leu Thr Ser Glu Asp Thr Ala Val Tyr Tyr Cys Ser Gly Ser
    210                 215                 220
```

```
Gly Asn Tyr Asp Trp Gly Gln Gly Thr Thr Leu Thr Val Ser Ala Lys
225                 230                 235                 240

Thr Thr Pro Pro Ser Val Thr Ser Gly Gln Ala Gly Gln
            245                 250
```

<210> SEQ ID NO 23
<211> LENGTH: 244
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(238)
<223> OTHER INFORMATION: Antibody 4E6G7 scFv Fusion Protein (SEQ ID NO: 17)
<220> FEATURE:
<221> NAME/KEY: MISC_FEATURE
<222> LOCATION: (239)..(244)
<223> OTHER INFORMATION: C-Terminal Peptide (SEQ ID NO:5)

<400> SEQUENCE: 23

```
Asp Ile Gln Met Asn Gln Ser Pro Ser Ser Leu Ser Ala Ser Leu Gly
1               5                   10                  15

Asp Thr Ile Thr Ile Ser Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Phe Glu Ala Ser Thr Leu Tyr Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg Ser Ser Gly Gly
            100                 105                 110

Gly Gly Ser Gly Gly Gly Gly Gly Ser Ser Arg Ser Ser Val Gln
        115                 120                 125

Leu Gln Gln Ser Gly Ala Glu Leu Val Gln Pro Gly Ala Ser Val Lys
    130                 135                 140

Leu Ser Cys Thr Ala Ser Gly Phe Asn Ile Lys Asp Thr Ser Met His
145                 150                 155                 160

Trp Val Arg Gln Arg Pro Glu Gln Gly Leu Glu Trp Ile Gly Arg Ile
                165                 170                 175

Ala Pro Ala Asn Gly Asn Thr Lys Tyr Asp Pro Lys Phe Gln Gly Lys
            180                 185                 190

Ala Thr Ile Thr Thr Asp Thr Ser Asn Thr Ala Tyr Leu Gln Leu
        195                 200                 205

Ser Ser Leu Thr Ser Glu Asp Thr Ala Val Tyr Tyr Cys Ser Gly Ser
    210                 215                 220

Gly Asn Tyr Asp Trp Gly Gln Gly Thr Thr Leu Thr Val Ser His His
225                 230                 235                 240

His His His His
```

<210> SEQ ID NO 24
<211> LENGTH: 250
<212> TYPE: PRT
<213> ORGANISM: Artificial Sequence
<220> FEATURE:

<223> OTHER INFORMATION: Antibody 4E6G7 scFv Fusion Protein
<220> FEATURE:
<221> NAME/KEY: MISC_FEATURE
<222> LOCATION: (1)..(238)
<223> OTHER INFORMATION: Antibody 4E6G7 scFv Fusion Protein (SEQ ID NO: 17)
<220> FEATURE:
<221> NAME/KEY: MISC_FEATURE
<222> LOCATION: (239)..(250)
<223> OTHER INFORMATION: C-Terminal Peptide (SEQ ID NO:6)

<400> SEQUENCE: 24

```
Asp Ile Gln Met Asn Gln Ser Pro Ser Ser Leu Ser Ala Ser Leu Gly
1               5                   10                  15
Asp Thr Ile Thr Ile Ser Cys His Ala Ser Gln Asn Ile Asn Val Trp
            20                  25                  30
Leu Ser Trp Tyr Gln Gln Lys Pro Gly Asn Ile Pro Lys Leu Leu Ile
        35                  40                  45
Phe Glu Ala Ser Thr Leu Tyr Thr Gly Val Pro Ser Arg Phe Ser Gly
    50                  55                  60
Ser Gly Ser Gly Thr Gly Phe Thr Leu Thr Ile Ser Ser Leu Gln Pro
65                  70                  75                  80
Glu Asp Ile Ala Thr Tyr Tyr Cys Gln Gln Gly Gln Ser Tyr Pro Trp
                85                  90                  95
Thr Phe Gly Gly Gly Thr Lys Leu Glu Ile Lys Arg Ser Ser Gly Gly
            100                 105                 110
Gly Gly Ser Gly Gly Gly Gly Ser Ser Arg Ser Ser Val Gln
        115                 120                 125
Leu Gln Gln Ser Gly Ala Glu Leu Val Gln Pro Gly Ala Ser Val Lys
    130                 135                 140
Leu Ser Cys Thr Ala Ser Gly Phe Asn Ile Lys Asp Thr Ser Met His
145                 150                 155                 160
Trp Val Arg Gln Arg Pro Glu Gln Gly Leu Glu Trp Ile Gly Arg Ile
                165                 170                 175
Ala Pro Ala Asn Gly Asn Thr Lys Tyr Asp Pro Lys Phe Gln Gly Lys
            180                 185                 190
Ala Thr Ile Thr Thr Asp Thr Ser Ser Asn Thr Ala Tyr Leu Gln Leu
        195                 200                 205
Ser Ser Leu Thr Ser Glu Asp Thr Ala Val Tyr Tyr Cys Ser Gly Ser
    210                 215                 220
Gly Asn Tyr Asp Trp Gly Gln Gly Thr Thr Leu Thr Val Ser Gly Ala
225                 230                 235                 240
Tyr Pro Tyr Asp Val Pro Asp Tyr Ala Ser
                245                 250
```

<210> SEQ ID NO 25
<211> LENGTH: 271
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(238)
<223> OTHER INFORMATION: Antibody 4E6G7 scFv Fusion Protein (SEQ ID NO: 17)
<220> FEATURE:
<221> NAME/KEY: MISC_FEATURE
<222> LOCATION: (239)..(271)
<223> OTHER INFORMATION: C-Terminal Peptide (SEQ ID NO:20)

<400> SEQUENCE: 25

Asp Ile Gln Met Asn Gln Ser Pro Ser Ser Leu Ser Ala Ser Leu Gly
1               5                   10                  15

Asp Thr Ile Thr Ile Ser Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Phe Glu Ala Ser Thr Leu Tyr Thr Gly Val Pro Ser Arg Phe Ser Gly
50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys Arg Ser Ser Gly Gly
            100                 105                 110

Gly Gly Ser Gly Gly Gly Gly Ser Ser Arg Ser Ser Val Gln
        115                 120                 125

Leu Gln Gln Ser Gly Ala Glu Leu Val Gln Pro Gly Ala Ser Val Lys
    130                 135                 140

Leu Ser Cys Thr Ala Ser Gly Phe Asn Ile Lys Asp Thr Ser Met His
145                 150                 155                 160

Trp Val Arg Gln Arg Pro Glu Gln Gly Leu Glu Trp Ile Gly Arg Ile
                165                 170                 175

Ala Pro Ala Asn Gly Asn Thr Lys Tyr Asp Pro Lys Phe Gln Gly Lys
            180                 185                 190

Ala Thr Ile Thr Thr Asp Thr Ser Asn Thr Ala Tyr Leu Gln Leu
        195                 200                 205

Ser Ser Leu Thr Ser Glu Asp Thr Ala Val Tyr Tyr Cys Ser Gly Ser
    210                 215                 220

Gly Asn Tyr Asp Trp Gly Gln Gly Thr Thr Leu Thr Val Ser Ala Lys
225                 230                 235                 240

Thr Thr Pro Pro Ser Val Thr Ser Gly Gln Ala Gly Gln His His His
                245                 250                 255

His His His Gly Ala Tyr Pro Tyr Asp Val Pro Asp Tyr Ala Ser
            260                 265                 270

<210> SEQ ID NO 26
<211> LENGTH: 281
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(28)
<223> OTHER INFORMATION: N-Terminal Leader Peptide (SEQ ID NO:18)
<220> FEATURE:
<221> NAME/KEY: MISC_FEATURE
<222> LOCATION: (29)..(266)
<223> OTHER INFORMATION: Antibody 4E6G7 scFv Fusion Protein (SEQ ID NO: 17)
<220> FEATURE:
<221> NAME/KEY: MISC_FEATURE
<222> LOCATION: (267)..(281)
<223> OTHER INFORMATION: C-Terminal Peptide (SEQ ID NO:5)

<400> SEQUENCE: 26

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Ile Gln Met

```
                    20                  25                  30

Asn Gln Ser Pro Ser Ser Leu Ser Ala Ser Leu Gly Asp Thr Ile Thr
            35                  40                  45

Ile Ser Cys His Ala Ser Gln Asn Ile Asn Val Trp Leu Ser Trp Tyr
        50                  55                  60

Gln Gln Lys Pro Gly Asn Ile Pro Lys Leu Leu Ile Phe Glu Ala Ser
65                  70                  75                  80

Thr Leu Tyr Thr Gly Val Pro Ser Arg Phe Ser Gly Ser Gly Ser Gly
                85                  90                  95

Thr Gly Phe Thr Leu Thr Ile Ser Ser Leu Gln Pro Glu Asp Ile Ala
            100                 105                 110

Thr Tyr Tyr Cys Gln Gln Gly Gln Ser Tyr Pro Trp Thr Phe Gly Gly
        115                 120                 125

Gly Thr Lys Leu Glu Ile Lys Arg Ser Ser Gly Gly Gly Ser Gly
    130                 135                 140

Gly Gly Gly Gly Ser Ser Arg Ser Val Gln Leu Gln Gln Ser
145                 150                 155                 160

Gly Ala Glu Leu Val Gln Pro Gly Ala Ser Val Lys Leu Ser Cys Thr
                165                 170                 175

Ala Ser Gly Phe Asn Ile Lys Asp Thr Ser Met His Trp Val Arg Gln
            180                 185                 190

Arg Pro Glu Gln Gly Leu Glu Trp Ile Gly Arg Ile Ala Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Ser Asn Thr Ala Tyr Leu Gln Leu Ser Ser Leu Thr
225                 230                 235                 240

Ser Glu Asp Thr Ala Val Tyr Tyr Cys Ser Gly Ser Gly Asn Tyr Asp
                245                 250                 255

Trp Gly Gln Gly Thr Thr Leu Thr Val Ser Ala Lys Thr Thr Pro Pro
            260                 265                 270

Ser Val Thr Ser Gly Gln Ala Gly Gln
        275                 280

<210> SEQ ID NO 27
<211> LENGTH: 272
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(28)
<223> OTHER INFORMATION: N-Terminal Leader Peptide (SEQ ID NO:18)
<220> FEATURE:
<221> NAME/KEY: MISC_FEATURE
<222> LOCATION: (29)..(266)
<223> OTHER INFORMATION: Antibody 4E6G7 scFv Fusion Protein (SEQ ID NO:
      17)
<220> FEATURE:
<221> NAME/KEY: MISC_FEATURE
<222> LOCATION: (267)..(272)
<223> OTHER INFORMATION: C-Terminal Peptide (SEQ ID NO:18)

<400> SEQUENCE: 27

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Ile Gln Met
                20                  25                  30
```

Asn Gln Ser Pro Ser Ser Leu Ser Ala Ser Leu Gly Asp Thr Ile Thr
            35                  40                  45

Ile Ser Cys His Ala Ser Gln Asn Ile Asn Val Trp Leu Ser Trp Tyr
 50                  55                  60

Gln Gln Lys Pro Gly Asn Ile Pro Lys Leu Leu Ile Phe Glu Ala Ser
 65                  70                  75                  80

Thr Leu Tyr Thr Gly Val Pro Ser Arg Phe Ser Gly Ser Gly Ser Gly
                85                  90                  95

Thr Gly Phe Thr Leu Thr Ile Ser Ser Leu Gln Pro Glu Asp Ile Ala
            100                 105                 110

Thr Tyr Tyr Cys Gln Gln Gly Gln Ser Tyr Pro Trp Thr Phe Gly Gly
            115                 120                 125

Gly Thr Lys Leu Glu Ile Lys Arg Ser Gly Gly Gly Gly Ser Gly
            130                 135                 140

Gly Gly Gly Gly Ser Ser Arg Ser Ser Val Gln Leu Gln Gln Ser
145                 150                 155                 160

Gly Ala Glu Leu Val Gln Pro Gly Ala Ser Val Lys Leu Ser Cys Thr
                165                 170                 175

Ala Ser Gly Phe Asn Ile Lys Asp Thr Ser Met His Trp Val Arg Gln
            180                 185                 190

Arg Pro Glu Gln Gly Leu Glu Trp Ile Gly Arg Ile Ala Pro Ala Asn
            195                 200                 205

Gly Asn Thr Lys Tyr Asp Pro Lys Phe Gln Gly Lys Ala Thr Ile Thr
            210                 215                 220

Thr Asp Thr Ser Ser Asn Thr Ala Tyr Leu Gln Leu Ser Ser Leu Thr
225                 230                 235                 240

Ser Glu Asp Thr Ala Val Tyr Tyr Cys Ser Gly Ser Gly Asn Tyr Asp
                245                 250                 255

Trp Gly Gln Gly Thr Thr Leu Thr Val Ser His His His His His His
            260                 265                 270

<210> SEQ ID NO 28
<211> LENGTH: 278
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(28)
<223> OTHER INFORMATION: N-Terminal Leader Peptide (SEQ ID NO:18)
<220> FEATURE:
<221> NAME/KEY: MISC_FEATURE
<222> LOCATION: (29)..(266)
<223> OTHER INFORMATION: Antibody 4E6G7 scFv Fusion Protein (SEQ ID NO:
    17)
<220> FEATURE:
<221> NAME/KEY: MISC_FEATURE
<222> LOCATION: (267)..(278)
<223> OTHER INFORMATION: C-Terminal Peptide (SEQ ID NO:6)

<400> SEQUENCE: 28

Ile Gln Glu Glu Phe Lys Met Lys Lys Thr Ala Ile Ala Ile Ala Val
 1               5                  10                  15

Ala Leu Ala Gly Phe Ala Thr Val Ala Gln Ala Ala Asp Ile Gln Met
            20                  25                  30

Asn Gln Ser Pro Ser Ser Leu Ser Ala Ser Leu Gly Asp Thr Ile Thr
            35                  40                  45

Ile Ser Cys His Ala Ser Gln Asn Ile Asn Val Trp Leu Ser Trp Tyr
 50                  55                  60

```
Gln Gln Lys Pro Gly Asn Ile Pro Lys Leu Leu Ile Phe Glu Ala Ser
 65                  70                  75                  80

Thr Leu Tyr Thr Gly Val Pro Ser Arg Phe Ser Gly Ser Gly Ser Gly
                 85                  90                  95

Thr Gly Phe Thr Leu Thr Ile Ser Ser Leu Gln Pro Glu Asp Ile Ala
            100                 105                 110

Thr Tyr Tyr Cys Gln Gln Gly Gln Ser Tyr Pro Trp Thr Phe Gly Gly
        115                 120                 125

Gly Thr Lys Leu Glu Ile Lys Arg Ser Ser Gly Gly Gly Gly Ser Gly
    130                 135                 140

Gly Gly Gly Gly Ser Ser Arg Ser Ser Val Gln Leu Gln Gln Ser
145                 150                 155                 160

Gly Ala Glu Leu Val Gln Pro Gly Ala Ser Val Lys Leu Ser Cys Thr
                165                 170                 175

Ala Ser Gly Phe Asn Ile Lys Asp Thr Ser Met His Trp Val Arg Gln
            180                 185                 190

Arg Pro Glu Gln Gly Leu Glu Trp Ile Gly Arg Ile Ala Pro Ala Asn
        195                 200                 205

Gly Asn Thr Lys Tyr Asp Pro Lys Phe Gln Gly Lys Ala Thr Ile Thr
    210                 215                 220

Thr Asp Thr Ser Ser Asn Thr Ala Tyr Leu Gln Leu Ser Ser Leu Thr
225                 230                 235                 240

Ser Glu Asp Thr Ala Val Tyr Tyr Cys Ser Gly Ser Gly Asn Tyr Asp
                245                 250                 255

Trp Gly Gln Gly Thr Thr Leu Thr Val Ser Gly Ala Tyr Pro Tyr Asp
            260                 265                 270

Val Pro Asp Tyr Ala Ser
            275

<210> SEQ ID NO 29
<211> LENGTH: 299
<212> TYPE: PRT
<213> ORGANISM: Artificial Sequence
<220> FEATURE:
<223> OTHER INFORMATION: Antibody 4E6G7 scFv Fusion Protein
<220> FEATURE:
<221> NAME/KEY: MISC_FEATURE
<222> LOCATION: (1)..(28)
<223> OTHER INFORMATION: N-Terminal Leader Peptide (SEQ ID NO:18)
<220> FEATURE:
<221> NAME/KEY: MISC_FEATURE
<222> LOCATION: (29)..(266)
<223> OTHER INFORMATION: Antibody 4E6G7 scFv Fusion Protein (SEQ ID NO:
      17)
<220> FEATURE:
<221> NAME/KEY: MISC_FEATURE
<222> LOCATION: (267)..(299)
<223> OTHER INFORMATION: C-Terminal Peptide (SEQ ID NO:20)

<400> SEQUENCE: 29

Ile Gln Glu Glu Phe Lys Met Lys Lys Thr Ala Ile Ala Ile Ala Val
 1               5                  10                  15

Ala Leu Ala Gly Phe Ala Thr Val Ala Gln Ala Ala Asp Ile Gln Met
                 20                  25                  30

Asn Gln Ser Pro Ser Ser Leu Ser Ala Ser Leu Gly Asp Thr Ile Thr
             35                  40                  45

Ile Ser Cys His Ala Ser Gln Asn Ile Asn Val Trp Leu Ser Trp Tyr
         50                  55                  60

Gln Gln Lys Pro Gly Asn Ile Pro Lys Leu Leu Ile Phe Glu Ala Ser
```

```
                65                  70                  75                  80
        Thr Leu Tyr Thr Gly Val Pro Ser Arg Phe Ser Gly Ser Gly
                        85                  90                  95
        Thr Gly Phe Thr Leu Thr Ile Ser Ser Leu Gln Pro Glu Asp Ile Ala
                        100                 105                 110
        Thr Tyr Tyr Cys Gln Gln Gly Gln Ser Tyr Pro Trp Thr Phe Gly Gly
                        115                 120                 125
        Gly Thr Lys Leu Glu Ile Lys Arg Ser Gly Gly Gly Ser Gly
                130                 135                 140
        Gly Gly Gly Gly Ser Ser Arg Ser Val Gln Leu Gln Ser
        145                 150                 155                 160
        Gly Ala Glu Leu Val Gln Pro Gly Ala Ser Val Lys Leu Ser Cys Thr
                        165                 170                 175
        Ala Ser Gly Phe Asn Ile Lys Asp Thr Ser Met His Trp Val Arg Gln
                        180                 185                 190
        Arg Pro Glu Gln Gly Leu Glu Trp Ile Gly Arg Ile Ala Pro Ala Asn
                        195                 200                 205
        Gly Asn Thr Lys Tyr Asp Pro Lys Phe Gln Gly Lys Ala Thr Ile Thr
                        210                 215                 220
        Thr Asp Thr Ser Ser Asn Thr Ala Tyr Leu Gln Leu Ser Ser Leu Thr
        225                 230                 235                 240
        Ser Glu Asp Thr Ala Val Tyr Tyr Cys Ser Gly Ser Gly Asn Tyr Asp
                        245                 250                 255
        Trp Gly Gln Gly Thr Thr Leu Thr Val Ser Ala Lys Thr Thr Pro Pro
                        260                 265                 270
        Ser Val Thr Ser Gly Gln Ala Gly Gln His His His His His His Gly
                        275                 280                 285
        Ala Tyr Pro Tyr Asp Val Pro Asp Tyr Ala Ser
                        290                 295

<210> SEQ ID NO 30
<211> LENGTH: 30
<212> TYPE: PRT
<213> ORGANISM: Artificial Sequence
<220> FEATURE:
<223> OTHER INFORMATION: Tau 379-408 (
Ser396/
Ser404)
<220> FEATURE:
<221> NAME/KEY: MOD_RES
<222> LOCATION: (18)..(18)
<223> OTHER INFORMATION: PHOSPHORYLATION (residue is phosphoserine)
<220> FEATURE:
<221> NAME/KEY: MOD_RES
<222> LOCATION: (26)..(26)
<223> OTHER INFORMATION: PHOSPHORYLATION (residue is phosphoserine)

<400> SEQUENCE: 30

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
                20                  25                  30

<210> SEQ ID NO 31
<211> LENGTH: 30
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Tau 379-408
```

```
<400> SEQUENCE: 31

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30
```

US 10,358,503 B2

ANTIBODY-BASED MOLECULES SELECTIVE FOR THE $^{\{P\}}$SER404 EPITOPE OF TAU AND THEIR USES IN THE DIAGNOSIS AND TREATMENT OF TAUOPATHY

CROSS-REFERENCE TO RELATED APPLICATIONS

This application is a § 371 Application of PCT/US2016/046520 (filed Aug. 11, 2016), which application claims priority to U.S. Patent Appln. Ser. No. 62/204,711 (filed Aug. 13, 2015), each of which applications is incorporated by reference herein in its entirety.

STATEMENT REGARDING FEDERALLY SPONSORED RESEARCH OR DEVELOPMENT

This invention was made with government support under Grant Nos. NS077239, AG032611 and AG020197, awarded by the National Institutes of Health (NIH). The government has certain rights in the invention.

REFERENCE TO SEQUENCE LISTING

This application includes one or more Sequence Listings pursuant to 37 C.F.R. 1.821 et seq., which are disclosed in computer-readable media (file name: 1400-0009PCT_ST25.txt, created on Aug. 6, 2016, and having a size of 38,518 bytes), which file is herein incorporated by reference in its entirety.

FIELD OF THE INVENTION

The present invention relates to antibody-based molecules (including single domain antibody fragment, scFv molecules, antibodies, antibody fragments, diabodies, and the epitope-binding domains thereof) that are capable of immunospecifically and selectively binding to the $^{\{P\}}$Ser404 Epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules (and in particular, scFv molecules) of the present invention have particular utility as diagnostic markers for, Alzheimer's disease and related tauopathies and as pharmaceutical compositions for the treatment of such conditions.

BACKGROUND OF THE INVENTION

Alzheimer's disease is the most common form of dementia affecting more than 20 million people worldwide. Diagnosis of the disease, in particular at an early point, is troublesome and difficult and there exists a need for accurate diagnosis of tauopathies such as Alzheimer's disease. Antibody detection of abnormal Tau in cerebrospinal fluid has shown some promise (Blennow, K. et al. "*Cerebrospinal Fluid And Plasma Biomarkers In Alzheimer Disease,*" Nat. Rev. Neurol. 6, 131-144 (2010) and Weiner et al. "*The Alzheimer's Disease Neuroimaging Initiative: A Review Of Papers Published Since Its Inception,*" Alzheimers. Dement. 9, e111-e194 (2013)).

Over the years, antibody detection of phospho-Tau protein in cerebrospinal fluid has shown some utility for diagnosis of Alzheimer's disease (Blennow, K. et al. "*Cerebrospinal Fluid And Plasma Biomarkers In Alzheimer Disease,*" Nat. Rev. Neurol. 6, 131-144 (2010); Lewis, J. et al. "*Neurofibrillary Tangles, Amyotrophy And Progressive Motor Disturbance In Mice Expressing Mutant (P301L) Tau Protein,*" Nat. Genet. 25, 402-405; Weiner, M. W. et al. (2013) "*The Alzheimer's Disease Neuroimaging Initiative: A Review Of Papers Published Since Its Inception,*" Alzheimers. Dement. 9: e111-e194), suggesting that further development in this arena is warranted (see, Congdon, E. E. (2014) "*Harnessing The Immune System For Treatment And Detection Of Tau Pathology,*" J. Alzheimers Dis. 40: S113-S121). However, CSF Tau levels in other tauopathies are usually not altered compared to controls (Theunis, C. et al. "*Efficacy And Safety Of A Liposome-Based Vaccine Against Protein Tau, Assessed In Tau.P301L Mice That Model Tauopathy,*" PLoS. One. 8, e72301 (2013); Hales, C. M. et al. (2013) "*From Frontotemporal Lobar Degeneration Pathology To Frontotemporal Lobar Degeneration Biomarkers,*" Int. Rev. Psychiatry 25:210-220), and imaging dyes may not detect pathological Tau in all tauopathies (Fodero-Tavoletti, M. T. et al. (2014) "*Assessing THK523 Selectivity For Tau Deposits In Alzheimer's Disease And Non-Alzheimer's Disease Tauopathies,*" Alzheimers. Res. Ther. 6:11). Imaging these Tau lesions in concert with amyloid-β (Aβ) is more likely to lead to accurate diagnosis as the regional pattern of Tau aggregates differs between the different tauopathies. Furthermore, all of them except Alzheimer's disease are in part defined by lack of Aβ deposition. In vivo imaging of AP plaques using compounds that bind well to β-sheets is already in clinical use (Mason, N. S. et al. (2013) "*Positron Emission Tomography Radioligands For In Vivo Imaging Of ABeta Plaques,*" J. Labelled Comp. Radiopharm. 56:89-95). Several such dye-based Tau-binding ligands have been identified recently in preclinical studies and some of those are being evaluated (Fodero-Tavoletti, M. T. et al. (2014) "*Assessing THK523 Selectivity For Tau Deposits In Alzheimer's Disease And Non-Alzheimer's Disease Tauopathies,*" Alzheimers. Res. Ther. 6:11; Fodero-Tavoletti, M. T. et al. (2011) "*18F-THK523: A Novel In Vivo Tau Imaging Ligand For Alzheimer's Disease,*" Brain 134:1089-1100; Zhang, W. et al. (2012) "*A Highly Selective And Specific PET Tracer For Imaging Of Tau Pathologies,*" J. Alzheimers. Dis. 31:601-612; Chien, D. T. et al. (2013) "*Early Clinical PET Imaging Results With The Novel PHF-Tau Radioligand [F-18]-T807,*" J. Alzheimers. Dis. 34:457-468; Maruyama, M. H. et al. (2013) "*Imaging Of Tau Pathology In A Tauopathy Mouse Model And In Alzheimer Patients Compared To Normal Controls,*" Neuron 79:1094-1108; Okamura, N. et al. (2005) "*Quinoline And Benzimidazole Derivatives: Candidate Probes For In Vivo Imaging Of Tau Pathology In Alzheimer's Disease,*" J. Neurosci. 25:10857-10862; Harada, R., et al. (2013) "*Comparison Of The Binding Characteristics Of [18F]THK-523 And Other Amyloid Imaging Tracers To Alzheimer's Disease Pathology,*" Eur. J. Nucl. Med. Mol. Imaging 40:125-132; Ono, M. et al. (2011) "*Rhodanine And Thiohydantoin Derivatives For Detecting Tau Pathology In Alzheimer's Brains,*" ACS Chem. Neurosci. 2:269-275; Xia, C. F. et al. (2013) "*[(18)F] T807, A Novel Tau Positron Emission Tomography Imaging Agent For Alzheimer's Disease,*" Alzheimers. Dement. 9:666-676; Chien, D. T. (2014) "*Early Clinical PET Imaging Results With The Novel PHF-Tau Radioligand [F18]-T808,*" J. Alzheimers. Dis. 38:171-184; Villemagne, V. L. et al. (2014) "*In Vivo Evaluation Of A Novel Tau Imaging Tracer For Alzheimer's Disease,*" Eur. J. Nucl. Med. Mol. Imaging 41:816-826; Okamura, N. et al. (2014) "*Non-Invasive Assessment Of Alzheimer's Disease*

Neurofibrillary Pathology Using 18F-THK5105 PET," Brain 137:1762-1771). The hope and promise for Tau based ligands is that they will be better than Aβ ligands to monitor the status and progression of neurodegeneration. Antibody-based probes are likely to provide greater specificity for detecting Tau lesions. In particular, smaller antibody fragments that bind to Tau are attractive as ligands for in vivo imaging to detect Tau lesions in patients with Alzheimer's disease or other tauopathies.

Within the cancer field, therapeutic antibodies have routinely been co-developed as imaging agents, and several such antibodies and Fab molecules are FDA approved for tumor imaging (Kaur, S. et al. "Recent Trends In Antibody-Based Oncologic Imaging," Cancer Lett. 315, 97-111 (2012)).

The present inventors have found antibody-derived molecules that provide excellent specificity for detecting Tau lesions, and in particular smaller single-chain variable antibody fragments (scFv molecules) which are attractive for in vivo imaging of Tau aggregates. It is envisaged that these antibody-derived imaging ligands can be useful in monitoring disease progression of Tau pathology, the efficacy of Tau-targeting therapies, and to identify Aβ negative tauopathies. Additionally, such antibody-derived molecules have utility as therapeutics in the prevention, treatment and management of Alzheimer's disease and other tauopathies.

SUMMARY OF THE INVENTION

The present invention relates to antibody-based molecules (including single domain antibody fragment, scFv molecules, antibodies, antibody fragments, diabodies, and the epitope-binding domains thereof) that are capable of immunospecifically and selectively binding to the $^{\{p\}}$Ser404 Epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules (and in particular, scFv molecules) of the present invention have particular utility as diagnostic markers for, Alzheimer's disease and related tauopathies and as pharmaceutical compositions for the treatment of such conditions.

In detail, the invention concerns an antibody-based molecule that is capable of immunospecifically binding to the $^{\{p\}}$Ser404 Epitope of Tau, wherein the epitope is present on a peptide having the sequence of Tau 386-408 ($^{\{p\}}$Ser396/$^{\{p\}}$Ser404) (SEQ ID NO:8):

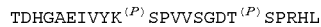

TDHGAEIVYK$^{(P)}$SPVVSGDT$^{(P)}$SPRHL wherein the residues at positions 11 and 19 thereof are phosphoserine, and wherein the antibody-based molecule is additionally capable of binding to phosphorylated Tau with greater selectivity than to non-phosphorylated Tau.

The invention particularly concerns the embodiment of the above-described antibody-based molecule wherein the molecule is an antibody or comprises an epitope-binding fragment of an antibody.

The invention particularly concerns the embodiment of the above-described antibody-based molecule wherein the molecule is a humanized antibody or comprises an epitope-binding fragment of a humanized antibody.

The invention particularly concerns the embodiment of the above-described antibody-based molecule wherein the molecule comprises a $^{\{p\}}$Ser404 Epitope-binding fragment of an antibody and is an isolated CDR, a single domain antibody fragment, an immunoglobulin Light Chain Variable Domain, an immunoglobulin Heavy Chain Variable Domain, an scFv or a diabody.

The invention particularly concerns the embodiment of the above-described antibody-based molecule wherein the molecule is an antibody or an epitope-binding fragment thereof that, upon peripheral injection into a recipient, substantially co-localizes with a Tau aggregate.

The invention particularly concerns the embodiment of the above-described antibody-based molecule wherein the epitope-binding fragment comprises any one, any two, any three, any four, any five or all six of:

(a) a Light Chain CDR1 having the amino acid sequence of SEQ ID NO:10;
(b) a Light Chain CDR2 having the amino acid sequence of SEQ ID NO:11;
(c) a Light Chain CDR3 having the amino acid sequence of SEQ ID NO:12;
(d) a Heavy Chain CDR1 having the amino acid sequence of SEQ ID NO:14;
(e) a Heavy Chain CDR2 having the amino acid sequence of SEQ ID NO:15; and/or
(f) a Heavy Chain CDR3 having the amino acid sequence of SEQ ID NO:16.

The invention particularly concerns the embodiment of the above-described antibody-based molecule wherein the epitope-binding fragment comprises a Variable Light Chain Domain having the amino acid sequence of SEQ ID NO:9 and/or a Variable Heavy Chain Domain having the amino acid sequence of SEQ ID NO:13.

The invention particularly concerns the embodiment of the above-described antibody-based molecule wherein the molecule is an scFv that comprises the amino acid sequence of SEQ ID NO:17.

The invention particularly concerns the embodiment of the above-described antibody-based molecule wherein the molecule is Antibody 4E6G7.

The invention particularly concerns the embodiment of any of the above-described antibody-based molecules wherein the molecule is detectably labeled, and in particular wherein the detectable label is a fluorescent label, a chemoluminescent label, a paramagnetic label, a radioisotopic label or an enzyme label.

The invention particularly concerns the use of any of the above-described antibody-based molecules for detecting or measuring the presence or amount of the phosphorylated Tau protein in the brain, cerebrospinal fluid, blood, serum or plasma of a recipient subject.

The invention particularly concerns such use of any of the above-described antibody-based molecules wherein the detection or measurement comprises in vivo or ex vivo imaging of the antibody-based molecule bound to the phosphorylated Tau protein.

The invention particularly concerns such use of any of the above-described antibody-based molecules wherein the detection or measurement is for diagnosing Alzheimer's disease or another tauopathy of a subject.

The invention additionally provides an in vivo medicament for the treatment of Alzheimer's disease or another tauopathy of a subject, wherein the medicament comprises any of the above-described antibody-based molecules in an amount effective to treat the Alzheimer's disease or other tauopathy, and one or more carriers, diluents and/or stabilizers.

The invention additionally provides the use of such vivo medicament for the treatment of Alzheimer's disease or another tauopathy of the subject.

The invention particularly concerns any of such uses wherein the subject is a human.

The invention additionally provides a kit for detecting or measuring the presence or amount of the phosphorylated Tau protein in the brain of a subject, or for diagnosing Alzheimer's disease or another tauopathy in a subject, wherein the kit comprises any of the above-described antibody-based molecules.

The invention particularly concerns any of the above-described uses, medicaments or kits, wherein the tauopathy is selected from the group comprising frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

BRIEF DESCRIPTION OF THE DRAWINGS

FIG. 9, Panel A shows a schematic of the microfluidic chambers, showing the reservoirs that receive the sampled cells. FIG. 9, Panel B is a magnified schematic of the central box in Panel A, showing the microgrooves that connect the two reservoirs. FIG. 9, Panel C is a confocal image showing axons (marked with arrows) growing through the microgrooves. The cell is stained with a pan-Tau antibody. FIG. 9, Panels D-F show fluorescently labeled PHF material (1 μg/mL) that was added to a chamber of the microfluidic device containing JNPL3 cells. FIG. 9, Panel D shows the location of Tau protein. FIG. 9, Panel E shows the location of PHF. FIG. 9, Panel F is a merged image showing both the location of Tau protein and the location of PHF.

FIG. 14, Panel C shows a quantitative analysis of the PHF-1 staining of brain cells of control and immunized mice.

FIG. 16, Panels A-F show that Antibody 4E6G7 and Antibody 6B2G12 differ in their binding to human derived PHF material. Panel A: Different tau species were spotted onto nitrocellulose and incubated with either Antibody 4E6G7 or Antibody 6B2G12 as the primary antibody. Antibody 4E6G7 bound better to solubilized PHF but Antibody 6B2G12 reacted more strongly with the sarkosyl insoluble tau fraction. Both antibodies had limited reactivity with sarkosyl soluble tau protein. Panel B: The same three tau fractions were prepared from control brain, and spotted onto nitrocellulose. Neither antibody showed binding to the sarkosyl soluble fraction, and only limited binding to the solubilized PHF and sarkosyl insoluble tau. (Images for all three samples for the Antibody 4E6G7 and Antibody 6B2G12 treated control brains were taken from the same strip, the order has been changed for clarity.) Panel C: Plates were coated with solubilized PHF from AD and control brains. Antibody 6B2G12 showed significantly higher binding to AD than control, and than Antibody 4E6G7 to either AD or control at dilutions, 1/200-1/125 (p<0.0001-0.05). Antibody 4E6G7 did not show significantly higher binding to AD versus control. Panel D: The assay plate was coated with sarkosyl soluble tau from AD and control brains, and serial dilutions of Antibody 4E6G7 and Antibody 6B2G12 were added. At the 1/200 dilution Antibody 6B2G12 showed significantly higher binding to AD than control, and higher binding than Antibody 4E6G7 to either fraction (p<0.01, 0.05 and 0.05 respectively). Panel E: Assay plates were coated with sarkosyl insoluble tau. Antibody 6B2G12 showed significantly higher binding to AD relative to control, and than Antibody 4E6G7 to either AD or control, from dilutions 1/200-1/125 k (p<0.0001-0.05). As before, no significant differences between AD and control sample were seen with Antibody 4E6G7. Panel F: Competitive ELISA assays were performed by pre-incubating the antibodies with increasing concentrations of solubilized PHF material (0.01-1 µg/ml). Antibody 6B2G12 binding was not inhibited at any PHF concentration. However, Antibody 4E6G7 binding was inhibited in a dose-dependent manner with an IC50 of 71 nM. All of the results show that Antibody 4E6G7 preferentially binds solubilized tau species, while Antibody 6B2G12 primarily binds to insoluble highly aggregated tau.

Figure 1:
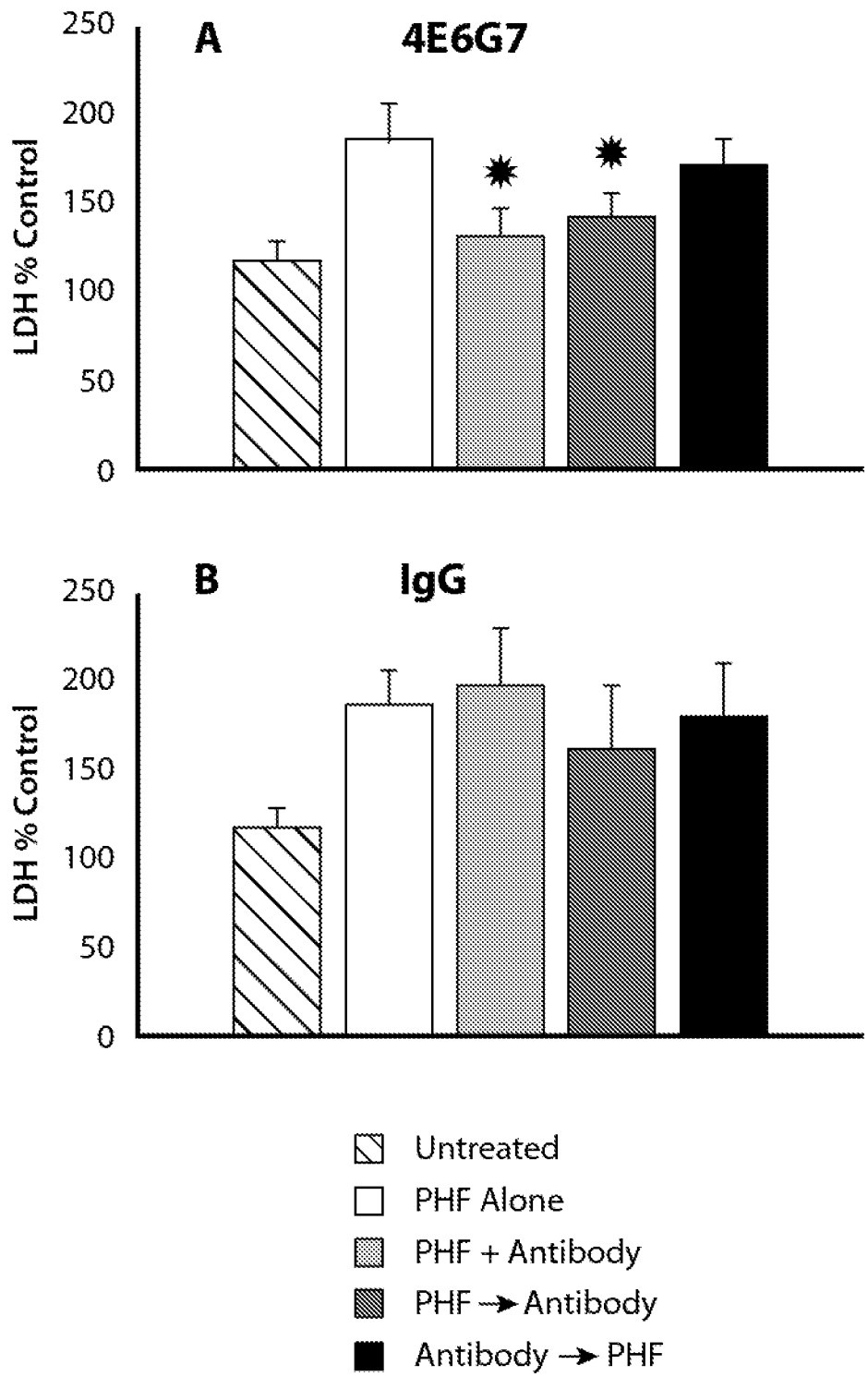
FIG. 1, Panels A-B show the effect of Antibody 4E6G7 (Panel A; *p=0.05) and IgG Control (Panel B) on cellular toxicity mediated by 10 μg/mL PHF as determined by LDH release.

All columns or points on each graph have SEM error bars, however some of those are too small to be visible.

DETAILED DESCRIPTION OF THE INVENTION

The present invention relates to antibody-based molecules (including single domain antibody fragment, scFv molecules, antibodies, antibody fragments, diabodies, and the epitope-binding domains thereof) that are capable of immunospecifically and selectively binding to the $^{\{p\}}$Ser404 Epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules (and in particular, scFv molecules) of the present invention have particular utility as diagnostic markers for, tauopathy (and in particular for Alzheimer's disease and related tauopathies) and as pharmaceutical compositions for the treatment of such conditions.

The term "tauopathy," as used herein, encompasses any neurodegenerative disease that involves the pathological aggregation of the microtubule protein Tau within the brain. Accordingly, in addition to both familial and sporadic Alzheimer's disease, the tauopathies of the present invention include, without limitation: frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

The antibody-based molecules of the present invention provide greater specificity than β-sheet dyes for detecting Tau lesions in patients with AD or other tauopathies. In particular, smaller antibody fragments that bind to Tau are attractive as ligands for in vivo imaging. Their smaller size compared to antibodies leads to better access to Tau aggregates. Another advantage is their relatively rapid clearance from the circulation compared to unmodified antibodies that have longer half-lives. Within the cancer field, therapeutic antibodies have routinely been co-developed as imaging agents, and several such antibodies and Fab's or smaller diabodies and scFv molecules with better pharmacokinetic properties approved or proposed as tumor imaging agents (see, Kaur, S. et al. (2012) "*Recent Trends In Antibody Based Oncologic Imaging*," Cancer Lett. 315:97-111; Olafsen, T. et al. (2010) "*Antibody Vectors For Imaging*," Semin. Nucl. Med. 40:167-181).

I. Tau and the Preferred Immunogenic Tau Peptides of the Present Invention

As used herein, the term "Tau" is synonymous with the Tau protein and refers to any of the Tau protein isoforms (identified in, for example, UniProt as P10636, 1-9). Tau is a soluble microtubule-associated protein that is dynamically phosphorylated and dephosphorylated by a host of kinase enzymes during the cell cycle. Tau's ability to stabilize microtubules is dependent on the extent of its phosphorylation. In its dephosphorylated form, the protein is able to interact with tubulin to stabilize microtubules and promote tubulin assembly into microtubules (which form the cytoskeleton of the cell and are the major constituents of the mitotic spindles that pull apart eukaryotic chromosomes in mitosis). In its phosphorylated form, Tau is able to dissociate from microtubules, thereby permitting mitosis to occur. The phosphorylation of Tau acts thus as a direct microtubule association-dissociation switch within the neuron (Pedersen, J. T. et al. (2015) "*Tau Immunotherapy For Alzheimer's Disease*," Trends Mol. Med. 2015 Apr. 3. pii: S1471-4914 (15)00058-1; pages 1-9, hereby incorporated by reference herein in its entirety).

The amino acid numbering of Tau residues provided herein is given with respect to SEQ ID NO: 1, as shown below, with methionine being the first amino acid residue thereof.

```
SEQ ID NO: 1:
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIINK

KLDLSNVQSK CGSKDNIKHV PGGGSVQIVY KPVDLSKVTS

KCGSLGNIHH KPGGGQVEVK SEKLDFKDRV QSKIGSLDNI

THVPGGGNKK IETHKLTFRE NAKAKTDHGA EIVYKSPVVS

GDTSPRHLSN VSSTGSIDMV DSPQLATLAD EVSASLAKQG L
```

The term "Phospho-Tau" or "P-Tau" refers to a Tau protein or peptide that has been phosphorylated at one or more serine or threonine residues. As used herein, the notation "$^{\{p\}}$Ser" or "$^{\{p\}}$S" denote the amino acid residue phosphoserine. For example, the notation "$^{\{p\}}$Ser396/$^{\{p\}}$Ser404" refers to a polypeptide portion of SEQ ID NO:1 wherein the residues that correspond to residues 396 and 404 of SEQ ID NO:1 (shown underlined above) are phosphoserine residues. In contrast, the notation "Ser396/Ser404" refers to a polypeptide portion of SEQ ID NO:1 wherein the residues that correspond to residues 396 and 404 of SEQ ID NO:1 are both serine residues. Thus, for example, the notation "$^{\{p\}}$Ser396/Ser404" refers to a polypeptide portion of SEQ ID NO:1 wherein the residue that corresponds to residue 396 of SEQ ID NO:1 is a phosphoserine residue, and the residue that corresponds to residue 404 of SEQ ID NO:1 is serine.

Hyperphosphorylation of Tau can result in the formation of insoluble self-assembling "tangles," referred to herein as "Tau aggregates," of paired helical filaments and straight filaments. Such Tau aggregates may be intracellular (e.g., intraneuronal), but may also form outside of the cells. The presence of Tau aggregates impairs Tau's ability to stabilize microtubules and thus leads to microtubule disassembly, dendritic spinal collapse, and the degeneration of axons. Normal Tau contains, on average two phosphorylated sites; the hyperphosphorylated Tau filaments average seven to eight phosphorylated sites. Hyperphosphorylated Tau is the main constituent of the intracellular neurofibrillary tangles that are a main hallmark of Alzheimer's Disease and other tauopathies. As used herein, the term "pathological Tau" refers to the hyperphosphorylated Tau that is characteristic of Alzheimer's Disease and other tauopathies.

II. The Preferred Antibody-Based Molecules of the Present Invention

The "antibody-based molecules" of the present invention include antibodies that are capable of immunospecifically and selectively binding to the $^{\{p\}}$Ser404 Epitope of Tau, as well as fragments and derivatives thereof that exhibit such binding immunospecificity and selectively. As used herein, a molecule is said to be a "fragment" of another molecule if it is obtained through the actual fragmenting of such parental molecule (for example, a Fab or (Fab)$_2$ fragment), or if it comprises an amino acid sequence that comprises a portion of the amino acid sequence of such parental molecule. As used herein, a molecule is said to be a "derivative" of another molecule (or relevant portion thereof) if it is obtained through the actual chemical modification of such parental molecule or portion thereof, or if it comprises an amino acid sequence that is substantially similar to the amino acid sequence of such parental molecule or relevant portion thereof (for example, differing by less than 30%, less than 20%, less than 10%, or less than 5% from such parental molecule or such relevant portion thereof, or by 10 amino acid residues, or by fewer than 10, 9, 8, 7, 6, 5, 4, 3 or 2 amino acid residues from such parental molecule or relevant portion thereof).

As used herein, the term "antibody" refers to an intact immunoglobulin as well as a molecule having an epitope-binding fragment thereof. As used herein, the terms "fragment," region" and "domain" are generally intended to be synonymous, unless the context of their use indicates otherwise. Naturally occurring antibodies typically comprise a tetramer which is usually composed of at least two heavy (H) chains and at least two light (L) chains. Each heavy chain is comprised of a heavy chain variable region (abbreviated herein as a "VH region") and a heavy chain constant region, usually comprised of three domains (CH1, CH2 and CH3 domains). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as a "VL region") and a light chain constant region (CL). Light chains include kappa chains and lambda chains. The heavy and light chain variable region is typically responsible for antigen recognition, while the heavy and light chain constant region may mediate the binding of the immunoglobulin to host tissues or factors, including various cells of the immune system (e.g., effector cells) and the first component (Clq) of the classical complement system. The VH and VL regions can be further subdivided into regions of hypervariability, termed "complementarity determining regions," or "CDRs," that are interspersed with regions of more conserved sequence, termed "framework regions" (FR). Each VH and VL region is composed of three CDR Domains and four FR Domains arranged from amino-terminus to carboxy-terminus in the following order: FR1-CDR1-FR2-CDR2-FR3-CDR3-FR4. The variable regions of the heavy and light chains contain a binding domain that interacts with an antigen. Of particular relevance are antibodies and their epitope-binding fragments that have been "isolated" so as to exist in a physical milieu distinct from that in which it may occur in nature or that have been modified so as to differ from a naturally-occurring antibody in amino acid sequence.

Fragments of antibodies (including Fab and (Fab)$_2$ fragments) that exhibit epitope-binding ability can be obtained, for example, by protease cleavage of intact antibodies. More preferably, such fragments will be single domain antibody fragments, scFv molecules, and the epitope-binding domains of antibodies, etc., that are formed using recombinant techniques. For example, although the two domains of the Fv fragment, the VL region and the VH region, are encoded by separate genes, such gene sequences or their encoding cDNA can be joined, using recombinant methods, by a flexible linker (typically of about 10, 12, 15 or more amino acid residues) that enables them to be made as a single protein chain in which the VL and VH regions associate to form monovalent epitope-binding molecules (known as single chain Fv (scFv) molecules; see e.g., Bird et al. (1988) "Single-Chain Antigen Binding Proteins," Science 242:423-426; and Huston et al. (1988) "Protein Engineering Of Antibody Binding Sites: Recovery Of Specific Activity In An Anti Digoxin Single-Chain Fv Analogue Produced In Escherichia coli," Proc. Natl. Acad. Sci. (U.S.A.) 85:5879-5883). Alternatively, by employing a flexible linker that is too short (e.g., less than about 9 residues) to enable the VL and VH regions of a single polypeptide chain to associate together, one can form a bispecific antibody, diabody, or similar molecule (in which two such polypeptide chains associate together to form a bivalent epitope-binding molecule) (see for instance Holliger, P. et al. (1993) "Diabodies': Small Bivalent And Bispecific Antibody Fragments," Proc. Natl. Acad. Sci. (U.S.A.) 90(14), 6444-8 (1993) for a description of diabodies). Single domain antibody fragments possess only one variable domain (e.g., VL or VH). Examples of the epitope-binding fragments encompassed within the present invention include (i) Fab' or Fab fragments, a monovalent fragment consisting of the VL, VN, CL and CH1 domains, or a monovalent antibody as described in WO2007059782; (ii) F(ab')$_2$ fragments, bivalent fragments comprising two Fab fragments linked by a disulfide bridge at the hinge region; (iii) Fd fragments consisting essentially of the VH and CH1 domains; (iv) Fv fragments consisting essentially of a VL and VH domain, (v) dAb fragments (Ward, E. S. et al. "Binding Activities Of A Repertoire Of Single Immunoglobulin Variable Domains Secreted From Escherichia coli," Nature 341:544-546 (1989)), which consist essentially of a VH domain and also called domain antibodies (Holt, L. J. et al. (2003) "Domain Antibodies: Proteins For Therapy," Trends Biotechnol. 21(11):484-490); (vi) camelid or nanobodies (Revets, H. et al. (2005) "Nanobodies As Novel Agents For Cancer Therapy," Expert Opin. Biol. Ther. 5(1)111-124) and (vii) isolated complementarity determining regions (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single-chain antibodies or single-chain Fv (scFv), see for instance Bird et al. (1988) "Single-Chain Antigen Binding Proteins," Science 242:423-426 and Huston et al. (1988) "Protein Engineering Of Antibody Binding Sites: Recovery Of Specific Activity In An Anti-Digoxin Single-Chain Fv Analogue Produced In Escherichia coli," Proc. Natl. Acad. Sci. (U.S.A.) 85:5879-5883). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3, IgG4, IgD, IgA, IgE, or IgM) that is encoded by heavy chain constant region genes. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-Tau antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1, κ.

Such antibody fragments are obtained using conventional techniques known to those of skill in the art. For example, F(ab')2 fragments may be generated by treating antibody with pepsin. The resulting F(ab')2 fragment may be treated to reduce disulfide bridges to produce Fab' fragments. Fab fragments may be obtained by treating an IgG antibody with papain; Fab' fragments may be obtained with pepsin digestion of IgG antibody. An F(ab') fragment may also be produced by binding Fab' described below via a thioether bond or a disulfide bond. A Fab' fragment is an antibody fragment obtained by cutting a disulfide bond of the hinge region of the F(ab')2. A Fab' fragment may be obtained by treating an F(ab')$_2$ fragment with a reducing agent, such as dithiothreitol. Antibody fragment may also be generated by expression of nucleic acids encoding such fragments in recombinant cells (see for instance Evans, M. J. et al. (1995) "Rapid Expression Of An Anti-Human C5 Chimeric Fab Utilizing A Vector That Replicates In COS And 293 Cells," J. Immunol. Meth. 184:123-38). For example, a chimeric gene encoding a portion of an F(ab')$_2$ fragment could include DNA sequences encoding the CH1 domain and hinge region of the H chain, followed by a translational stop codon to yield such a truncated antibody fragment molecule. Suitable fragments capable of binding to a desired epitope may be readily screened for utility in the same manner as an intact antibody.

In one embodiment, such antibody fragments are a monovalent antibody, preferably a monovalent antibody as described in PCT Publication WO 2007/059782 (which is incorporated herein by reference in its entirety) having a deletion of the hinge region. Such an antibody may be constructed by a method comprising: i) providing a nucleic acid construct encoding the light chain of said monovalent antibody, said construct comprising a nucleotide sequence encoding the VL region of a selected antigen-specific anti-alpha-synuclein antibody and a nucleotide sequence encoding the constant CL region of an Ig, wherein said nucleotide sequence encoding the VL region of a selected antigen-specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen-specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulfide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen-specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the antibody is a monovalent antibody, which comprises:
(i) a variable region of an antibody of the invention as described herein or an antigen-binding part of the said region, and
(ii) a CH region of an immunoglobulin or a fragment thereof comprising the CH2 and CH3 regions, wherein the CH region or fragment thereof has been modified such that the region corresponding to the hinge region and, if the immunoglobulin is not an IgG4 subtype, other regions of the CH region, such as the CH3 region, do not comprise any amino acid residues, which are capable of forming disulfide bonds with an identical CH region or other covalent or stable non-covalent inter-heavy chain bonds with an identical CH region in the presence of polyclonal human IgG.

In a further embodiment, the heavy chain of the monovalent antibody has been modified such that the entire hinge has been deleted.

In another further embodiment, the sequence of said monovalent antibody has been modified so that it does not comprise any acceptor sites for N-linked glycosylation.

As used herein, an antibody or an epitope-binding fragment thereof is said to "immunospecifically" bind a region of another molecule (i.e., an epitope) if it reacts or associates more frequently, more rapidly, with greater duration and/or with greater affinity or avidity with that epitope relative to alternative epitopes. It is also understood by reading this definition that, for example, an antibody or an epitope-binding fragment thereof that immunospecifically binds to a first target may or may not specifically or preferentially bind to a second target.

As used herein, the term "binding" in the context of the binding of an antibody or binding fragment thereof to a predetermined antigen typically refers to binding with an affinity corresponding to a $K_D$ of about $10^{-7}$ M or less, such as about $10^{-8}$ M or less, such as about $10^{-9}$ M or less when determined by, for instance, surface plasmon resonance (SPR) technology in a BIACORE™ 3000 instrument (preferably using the antibody as the ligand and the antigen as the analyte), and which binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., bovine serum albumin ("BSA"), casein, etc.) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$k_d$" ($sec^{-1}$ or 1/s), as used herein, refers to the dissociation rate constant of a particular antibody-antigen interaction. Said value is also referred to as the $k_{off}$ value. The term "$k_a$" ($M^{-1} \times sec^{-1}$ or 1/M), as used herein, refers to the association rate constant of a particular antibody-antigen interaction. The term "$K_D$" (M), as used herein, refers to the dissociation equilibrium constant of a particular antibody-antigen interaction and is obtained by dividing the $k_d$ by the $k_a$. The term "$K_A$" ($M^{-1}$ or 1/M), as used herein, refers to the association equilibrium constant of a particular antibody-antigen interaction and is obtained by dividing the $k_a$ by the $k_d$.

As used herein, an antibody or an epitope-binding fragment thereof is said to "selectively" bind to a phosphorylated peptide epitope if it immunospecifically binds to an epitope with higher affinity than it binds (if it binds at all) to a non-phosphorylated peptide epitope having the same amino acid sequence. Most preferably, such higher affinity will be at least 10-fold higher, at least 30-fold higher, at least 100-fold higher, at least 300-fold higher, at least 1,000-fold higher, at least 3,000-fold higher, or at least 10,000-fold higher. The extent of "selectivity" of an antibody, or of an epitope-binding fragment thereof, for phosphorylated Tau is determined by comparing, via ELISA or BIACORE™, the affinity with which an antibody or an epitope-binding fragment thereof immunospecifically binds to a non-phosphorylated target Tau peptide and to a phosphorylated variant thereof.

The term "epitope" refers to an antigenic determinant capable of being immunospecifically bound to an antibody. Epitopes usually comprise surface groupings of molecules such as amino acids or sugar side chains and usually have specific three dimensional structural characteristics, as well as specific charge characteristics. Conformational and non-conformational epitopes are distinguished in that the binding to the former, but not the latter, is lost in the presence of denaturing solvents. An epitope may comprise amino acid residues directly involved in the binding (also called the immunodominant component of the epitope) and other amino acid residues, which are not directly involved in the binding, such as amino acid residues that are effectively blocked by the specific antigen-binding peptide (in other words, the amino acid residue is within the footprint of the specific antigen-binding peptide).

As used herein, the term "epitope-binding fragment of an antibody" means a fragment of an antibody capable of immunospecifically binding to an epitope. An epitope-binding fragment may contain 1, 2, 3, 4, 5 or all 6 of the CDR Domains of such antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino-terminus and a carboxyl terminus (e.g., a diabody, an Fab fragment, an (Fab)$_2$ fragment, etc.).

The antibody-based molecules of the present invention, and their Tau epitope-binding fragments will preferably be "humanized," particularly if they are to be employed for therapeutic purposes. The term "humanized" refer to a chimeric molecule, generally prepared using recombinant techniques, having an antigen-binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild-type (e.g., fully human) or they may be modified to contain one or more amino acid substitutions not found in the human antibody whose sequence has served as the basis for humanization. Humanization lessens or eliminates the likelihood that a constant region of the molecule will act as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856, Riechmann, L. et al. (1988) "*Reshaping Human Antibodies for Therapy*," Nature 332: 323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody. The ability to humanize an antigen is well-known (see, e.g., U.S. Pat. Nos. 5,225,539; 5,530,101; 5,585,089; 5,859,205; 6,407,213; 6,881,557).

In one embodiment, an antibody-based molecule of the invention is a human antibody. Suitable human antibodies may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice."

The HuMAb mouse contains a human immunoglobulin gene minilocus that encodes unrearranged human heavy variable and constant (μ and Y) and light variable and constant (K) chain immunoglobulin sequences, together with targeted mutations that inactivate the endogenous μ and K chain loci (Lonberg, N. et al. (1994) "*Antigen-Specific Human Antibodies From Mice Comprising Four Distinct Genetic Modifications*," Nature 368:856-859). Accordingly, such mice exhibit reduced expression of mouse IgM or IgK and in response to immunization, the introduced human heavy and light chain transgenes, undergo class switching and somatic mutation to generate high affinity human IgG, κ monoclonal antibodies (Lonberg, N. et al. (1994) "*Antigen-Specific Human Antibodies From Mice Comprising Four Distinct Genetic Modifications*," Nature 368:856-859; Lonberg, N. (1994) "*Human Monoclonal Antibodies from Transgenic Mice,*" In: HANDBOOK EXPERIMENTAL PHARMACOLOGY, Volume 181 (Starke, K. et al., Eds.) Springer-Verlag Berlin Heidelberg; Lonberg, N. et al. (1995) "*Human Antibodies From Transgenic Mice*," Intern. Rev. Immunol. 13(1): 65-93; Harding, F. et al. (1995) "*Class Switching In Human Immunoglobulin Transgenic Mice*," Ann. N.Y. Acad. Sci 764:536-546). The preparation of HuMAb mice is described in detail in Taylor, L. et al. (1992) "*A Transgenic Mouse That Expresses A Diversity Of Human Sequence Heavy And Light Chain Immunoglobulins*," Nucl. Acids Res. 20(23):6287-6295; Chen, J. et al. (1993) "*Immunoglobulin Gene Rearrangement In B Cell Deficient Mice Generated By Targeted Deletion Of The JH Locus*," Int'l. Immunol. 5:647-656; Tuaillon, N. et al. (1994) "*Biased Utilization Of DHQ52 And JH4 Gene Segments In A Human Ig Transgenic Minilocus Is Independent Of Antigenic Selection*," J. Immunol. 152:2912-2920; Taylor, L. et al. (1994) "*Human Immunoglobulin Transgenes Undergo Rearrangement, Somatic Mutation And Class Switching In Mice That Lack Endogenous IgM*," Int'l. Immunol. 6:579-591; Fishwild, D. et al. (1996) "*High Avidity Human IgG Kappa Monoclonal Antibodies From A Novel Strain Of Minilocus Transgenic Mice*," Nature Biotechnol. 14:845-851; see also U.S. Pat. No. 5,545,806; 5,569,825; 5,625,126; 5,633,425; 5,789,650; 5,877,397; 5,661,016; 5,814,318; 5,874,299; 5,770,429; 5,545,807; PCT Publications WO 98/24884, WO 94/25585, WO 93/1227, WO 92/22645, WO 92/03918 and WO 01/09187).

The HCo7 mice have a JKD disruption in their endogenous light chain (kappa) genes (as described in Chen et al. (1993) "*B Cell Development In Mice That Lack One Or Both Immunoglobulin Kappa Light Chain Genes*," EMBO J. 12:821-830), a CMD disruption in their endogenous heavy chain genes (as described in Example 1 of PCT Publication WO 01/14424), a KCo5 human kappa light chain transgene (as described in Fishwild, D. et al. (1996) "*High-Avidity Human IgG Kappa Monoclonal Antibodies From A Novel Strain Of Minilocus Transgenic Mice*," Nature Biotechnol. 14:845-851), and a HCo7 human heavy chain transgene (as described in U.S. Pat. No. 5,770,429).

The HCo12 mice have a JKD disruption in their endogenous light chain (kappa) genes (as described in Chen et al. (1993) "*B Cell Development In Mice That Lack One Or Both Immunoglobulin Kappa Light Chain Genes*," EMBO J. 12:821-830), a CMD disruption in their endogenous heavy chain genes (as described in Example 1 of PCT Publication WO 01/14424), a KCo5 human kappa light chain transgene (as described in Fishwild, D. et al. (1996) "*High-Avidity Human IgG Kappa Monoclonal Antibodies From A Novel Strain Of Minilocus Transgenic Mice*," Nature Biotechnol. 14:845-851), and a HCo12 human heavy chain transgene (as described in Example 2 of PCT Publication WO 01/14424).

In the KM mouse strain, the endogenous mouse kappa light chain gene has been homozygously disrupted as described in Chen et al. (1993) "*B Cell Development In Mice That Lack One Or Both Immunoglobulin Kappa Light Chain Genes*," EMBO J. 12:821-830) and the endogenous mouse heavy chain gene has been homozygously disrupted as described in Example 1 of PCT Publication WO 01/09187. This mouse strain carries a human kappa light chain transgene, KCo5, as described in Fishwild, D. et al. (1996) "*High-Avidity Human IgG Kappa Monoclonal Antibodies From A Novel Strain Of Minilocus Transgenic Mice*," Nature Biotechnol. 14:845-851). This mouse strain also carries a human heavy chain transchromosome composed of chromosome 14 fragment hCF (SC20) as described in PCT Publication WO 02/43478.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690; 5,756,687; 5,750,172 and 5,741,957.

In some antibodies only part of a CDR, namely the subset of CDR residues required for binding, termed the "SDRs," are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable Regions Of Immunoglobulins*," J. Mol. Biol. 196:901-917), by molecular modeling and/or empirically, or as described in Gonzales, N. R. et al. (2004) "*SDR Grafting Of A Murine Antibody Using Multiple Human Germline Templates To Minimize Its Immunogenicity*," Mol. Immunol. 41:863-872. In such humanized antibodies at positions in which one or more donor CDR residues is absent or in which an entire donor CR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The fact that a single amino acid alteration of a CDR residue can result in loss of functional binding (Rudikoff, S. et al. (1982) "*Single Amino Acid Substitution Altering Antigen Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "*Amino acid substitution matrices from protein blocks*," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to ROR1, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |

TABLE 1-continued

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| N | -2 | 0 | +6 | +1 | -3 | 0 | 0 | 0 | +1 | -3 | -3 | 0 | -2 | -3 | -2 | +1 | 0 | -4 | -2 | -3 |
| D | -2 | -2 | +1 | +6 | -3 | 0 | +2 | -1 | -1 | -3 | -4 | -1 | -3 | -3 | -1 | 0 | -1 | -4 | -3 | -3 |
| C | 0 | -3 | -3 | -3 | +9 | -3 | -4 | -3 | -3 | -1 | -1 | -3 | -1 | -2 | -3 | -1 | -1 | -2 | -2 | -1 |
| Q | -1 | +1 | 0 | 0 | -3 | +5 | +2 | -2 | 0 | -3 | -2 | +1 | 0 | -3 | -1 | 0 | -1 | -2 | -1 | -2 |
| E | -1 | 0 | 0 | +2 | -4 | +2 | +5 | -2 | 0 | -3 | -3 | +1 | -2 | -3 | -1 | 0 | -1 | -3 | -2 | -2 |
| G | 0 | -2 | 0 | -1 | -3 | -2 | -2 | +6 | -2 | -4 | -4 | -2 | -3 | -3 | -2 | 0 | -2 | -2 | -3 | -3 |
| H | -2 | 0 | +1 | -1 | -3 | 0 | 0 | -2 | +8 | -3 | -3 | -1 | -2 | -1 | -2 | -1 | -2 | -2 | +2 | -3 |
| I | -1 | -3 | -3 | -3 | -1 | -3 | -3 | -4 | -3 | +4 | +2 | -3 | +1 | 0 | -3 | -2 | -1 | -3 | -1 | +3 |
| L | -1 | -2 | -3 | -4 | -1 | -2 | -3 | -4 | -3 | +2 | +4 | -2 | +2 | 0 | -3 | -2 | -1 | -2 | -1 | +1 |
| K | -1 | +2 | 0 | -1 | -3 | +1 | +1 | -2 | -1 | -3 | -2 | +5 | -1 | -3 | -1 | 0 | -1 | -3 | -2 | -2 |
| M | -1 | -1 | -2 | -3 | -1 | 0 | -2 | -3 | -2 | +1 | +2 | -1 | +5 | 0 | -2 | -1 | -1 | -1 | -1 | +1 |
| F | -2 | -3 | -3 | -3 | -2 | -3 | -3 | -3 | -1 | 0 | 0 | -3 | 0 | +6 | -4 | -2 | -2 | +1 | +3 | -1 |
| P | -1 | -2 | -2 | -1 | -3 | -1 | -1 | -2 | -2 | -3 | -3 | -1 | -2 | -4 | +7 | -1 | -1 | -4 | -3 | -2 |
| S | +1 | -1 | +1 | 0 | -1 | 0 | 0 | 0 | -1 | -2 | -2 | 0 | -1 | -2 | -1 | +4 | +1 | -3 | -2 | -2 |
| T | 0 | -1 | 0 | -1 | -1 | -1 | -1 | -2 | -2 | -1 | -1 | -1 | -1 | -2 | -1 | +1 | +5 | -2 | -2 | 0 |
| W | -3 | -3 | -4 | -4 | -2 | -2 | -3 | -2 | -2 | -3 | -2 | -3 | -1 | +1 | -4 | -3 | -2 | +11 | +2 | -3 |
| Y | -2 | -2 | -2 | -3 | -2 | -1 | -2 | -3 | +2 | -1 | -1 | -2 | -1 | +3 | -3 | -2 | -2 | +2 | +7 | -1 |
| V | 0 | -3 | -3 | -3 | -1 | -2 | -2 | -3 | -3 | +3 | +1 | -2 | +1 | -1 | -2 | -2 | 0 | -3 | -1 | +4 |

The invention thus contemplates the use of guided or random mutagenesis to identify improved CDRs.

In the context of the present invention, conservative substitutions may be defined by substitutions within the classes of amino acids reflected in one or more of the following three tables:

Amino Acid Residue Classes for Conservative Substitutions:

TABLE 2

| Acidic Residues | Asp (D) and Glu (E) |
|---|---|
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| 1 | A | S | T |
|---|---|---|---|
| 2 | D | E | |
| 3 | N | Q | |
| 4 | R | K | |
| 5 | I | L | M |
| 6 | F | Y | W |

Alternative Physical and Functional Classifications of Amino Acid Residues:

TABLE 4

| Alcohol Group-Containing Residues | S and T |
|---|---|
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) PROTEINS: STRUCTURE AND MOLECULAR PROPERTIES (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (See, e.g. Glaser et al. (1992) "Antibody Engineering By Codon-Based Mutagenesis In A Filamentous Phage Vector System," J. Immunology 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu, H. et al. (1998) "Stepwise In Vitro Affinity Maturation Of Vitaxin, An Alphav Beta3-Specific Humanized mAb," Proc. Natl. Acad. Sci. (U.S.A.) 95:6037-6042; Yelton et al. (1995) "Affinity Maturation Of The BR96 Anti-Carcinoma Antibody By Codon-Based Mutagenesis," J. Immunology 155:1994). CDR walking, which randomizes the Light Chain, may be used (see, Schier, R. et al. (1996) "Isolation Of Picomolar Affinity Anti-c-erbB-2 Single-Chain Fv By Molecular Evolution Of The Complementarity Determining Regions In The Center Of The Antibody Binding Site," J. Mol. Biol. 263:551-567).

Methods for accomplishing such affinity maturation are described for example in: Krause, J. C. et al. (2011) "An Insertion Mutation That Distorts Antibody Binding Site Architecture Enhances Function Of A Human Antibody," MBio. 2(1) pii: e00345-10. doi: 10.1128/mBio.00345-10; Kuan, C. T. et al. (2010) "Affinity Matured Anti-Glycoprotein NMB Recombinant Immunotoxins Targeting Malignant Gliomas And Melanomas," Int. J. Cancer 10.1002/ijc.25645; Hackel, B. J. et al. (2010) "Stability And CDR Composition Biases Enrich Binder Functionality Landscapes," J. Mol. Biol. 401(1):84-96; Montgomery, D. L. et al. (2009) "Affinity Maturation And Characterization Of A Human Monoclonal Antibody Against HIV-1 gp41," MAbs 1(5):462-474; Gustchina, E. et al. (2009) "Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth," Virology 393(1):112-119; Finlay, W. J. et al. (2009) "Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions," J. Mol. Biol. 388(3):541-558; Bostrom, J. et al. (2009) "Improving Antibody Binding Affinity And Specificity For Therapeutic Development," Methods Mol. Biol. 525: 353-376; Steidl, S. et al. (2008) "In Vitro Affinity Maturation Of Human GM-CSF Antibodies By Targeted CDR-Diversification," Mol. Immunol. 46(1):135-144; and Barderas, R. et al. (2008) "Affinity Maturation Of Antibodies Assisted By In Silico Modeling," Proc. Natl. Acad. Sci. (USA) 105(26): 9029-9034.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-Tau antibody when immunized with Tau antigen and/or cells expressing Tau. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in PCT Publication WO 02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

The use of the antibody-based molecules of the present invention as Tau imaging probes has great potential due to their specificity. Because of the general impermeability of the blood-brain barrier, smaller single-chain variable antibody fragments (scFv molecules) have been found to be preferred as in vivo imaging ligands to detect Tau lesions. scFv molecules are formed as a fusion protein of the variable regions of the heavy (H) and light chains (L) domains of an antibody, connected to one another via a short linker peptide of from about 10 to about 25 amino acid residues. The linker is usually rich in glycine for flexibility (e.g., GGGGSGGGGSGGGGS (SEQ ID NO:2) (Fisher, A. et al. (2009) "Efficient Isolation Of Soluble Intracellular Single-Chain Antibodies Using The Twin Arginine Translocation Machinery," J. Nol. Biol. 385(1):299-311; Bird, R. E. et al. (1988) "Single-Chain Antigen-Binding Proteins," Science 242:423-426; Huston, J. S. et al. (1988) "Protein Engineering Of Antibody Binding Sites: Recovery Of Specific Activity In An Anti-Digoxin Single-Chain Fv Analogue Produced In Escherichia coli," Proc. Natl. Acad. Sci. (U.S.A.) 85:5879-5883), as well as serine or threonine for solubility, and can either connect the N-terminus of the Heavy Chain Variable Domain with the C-terminus of the Light Chain Variable Domain VL, or vice versa (Huang, L. et al. (2013) "Single-Chain Fragment Variable Passive Immunotherapies For Neurodegenerative Diseases," Int. J. Mol. Sci. 14(9): 19109-19127; Ahmad, Z. A. et al. (2012) "scFv Antibody: Principles And Clinical Application," Clin. Dev. Immunol. 2012: 980250; Huhalov, A. et al. (2004) "Engineered Single-Chain Antibody Fragments For Radioimmunotherapy," Q. J. Nucl. Med. Mol. Imaging 48(4):279-288). An example of such a linker is GSTSGSGKPGSGEGSTKG (SEQ ID NO:3) (Whitlow, M. et al. (1993) "An Improved Linker For Single-Chain Fv With Reduced Aggregation And Enhanced Proteolytic Stability," Protein Eng. 6:989-995). A particularly preferred linker for the present invention has the amino acid sequence (SEQ ID NO:4): SSGGGGSGGGGGGSSRSS.

In order to facilitate purification and/or recovery, the scFv may include a poly histidine ("His-Tag") (e.g., (SEQ ID NO:5) HHHHHH). The imidazole side chains of the histidine residues of the His-Tag can engage in reversible coordinative bonds to certain transition metal ions, such as $Co^{2+}$, $Zn^{2+}$ and especially $Ni^{+2}$. Thus, when His-tagged scFv molecules are applied to a matrix containing such metal ions, they specifically bind to the matrix, while most untagged proteins do not. The scFv may additionally or alternatively include an "HA-Tag" such as (SEQ ID NO:6) GAYPYDVPDYAS. Human influenza hemagglutinin (HA) is a surface glycoprotein required for the infectivity of the human virus. The HA-tag is derived from the human influenza hemagglutinin (HA) surface glycoprotein, and permits detection of the scFv using an anti-HA-Tag antibody (Millipore).

scFv molecules may be expressed directly or as a fusion protein that is linked to an N-terminal leader peptide that is cleaved in order to yield the scFv (see, e.g., Huston, J. S. et al. (1988) "Protein Engineering Of Antibody Binding Sites: Recovery Of Specific Activity In An Anti-Digoxin Single-Chain Fv Analogue Produced In Escherichia coli," Proc. Natl. Acad. Sci. (U.S.A.) 85:5879-5883). For example, the scFv may be fused to the modified trp LE leader peptide (MLE)), and cleaved away by acid cleavage of the Asp-Pro peptide bond (Piszkiewicz, D. et al. (1970) "Anomalous Cleavage Of Aspartyl-Proline Peptide Bonds During Amino Acid Sequence Determinations," Biochem. Biophys. Res. Commun. 40(5):1173-1178; Fraser, K. J. et al. (1972) "Specific Cleavage Between Variable And Constant Domains Of Rabbit Antibody Light Chains By Dilute Acid Hydrolysis," Biochemistry 11(26):4974-4977; Poulsen, K. et al. (1972) "An Active Derivative Of Rabbit Antibody Light Chain Composed Of The Constant And The Variable Domains Held Together Only By A Native Disulfide Bond," Proc. Natl. Acad. Sci. (U.S.A.) 69(9):2495-2499).

In a further embodiment, an scFv can be linked to another scFv (which may be the same or different) in order to form a bivalent molecule. This can be done by producing a single peptide chain with two VH and two VL regions, yielding tandem scFv molecules (Xiong, C.-Y. et al. (2006) "Development Of Tumor Targeting Anti-MUC-1 Multimer: Effects Of di-scFv Unpaired Cysteine Location On PEGylation And Tumor Binding," Protein Engineering Design and Selection 19(8):359-367; Kufer, P. et al. (2004) "A Revival Of Bispecific Antibodies," Trends in Biotechnology 22(5):238-24). Alternatively, by an forming scFv whose Heavy Chain Variable Domain is separated from its Light Chain Variable Domain by a linker that is too short to permit such domains to complex with one another and form an epitope-binding site, one can force two scFv molecules to dimerize as a diabody (Hollinger, P. et al. (1993) "*Diabodies*": *Small Bivalent And Bispecific Antibody Fragments*," Proc. Natl. Acad. Sci. (U.S.A.) 90(14):6444-6448). Diabodies have been shown to have dissociation constants up to 40-fold lower than corresponding scFv molecules, meaning that they have a much higher affinity to their target. Consequently, diabody drugs could be dosed much lower than other therapeutic antibodies and are capable of highly specific targeting of tumors in vivo (Adams, G. P. et al. (1998) "*Prolonged in vivo Tumour Retention Of A Human Diabody Targeting The Extracellular Domain Of Human HER2/neu*," Brit. J. Cancer 77(9):1405-1412). Still shorter linkers (one or two amino acids) lead to the formation of trimers, so-called triabodies or tribodies. Tetrabodies have also been produced. They exhibit an even higher affinity to their targets than diabodies (Le Gall, F. et al. (1999) "*Di-, Tri-And Tetrameric Single-Chain Fv Antibody Fragments Against Human CD19: Effect Of Valency On Cell Binding*," FEBS Letters 453(1):164-168). All of these formats can be composed from variable scFv molecules so as to form dimers, trimers, etc. having specificity for two or more different epitopes (i.e., bispecific diabodies, etc.) (Dincq, S. et al. (2001) "*Expression And Purification Of Monospecific And Bispecific Recombinant Antibody Fragments Derived From Antibodies That Block The CD80/CD86-CD28 Costimulatory Pathway*," Protein Express. Purificat. 22(1):11-24).

A. The "$^{\{P\}}$Ser404 Epitope"

The antibody-based molecules of the present invention exhibit immunospecificity to the phosphoserine residue $^{\{P\}}$Ser404 of Tau (SEQ ID NO:1) and its related isoforms, and are therefore referred to herein as exhibiting immunospecificity for the "$^{\{P\}}$Ser404 Epitope." As used herein, an antibody is said to exhibit immunospecificity for the $^{\{P\}}$Ser404 Epitope if it exhibits enhanced binding to the $^{\{P\}}$Ser404 phosphoserine residue relative to $^{\{P\}}$Ser396 or to any other amino acid residue(s) of the immunogen, such that replacement of $^{\{P\}}$Ser404 with Ser404 diminishes binding by such $^{\{P\}}$Ser404 Epitope-specific antibody to such variant immunogen to a greater extent than the replacement of any other residue of such immunogen. Although any immunogen containing the $^{\{P\}}$Ser404 Epitope may be employed to isolate and characterize such antibodies, it is preferred to employ a peptide having the amino acid sequence (SEQ ID NO:7): TDHGAEIVYKSPVVSGDTSPRHL (which corresponds to amino acid residues 386-408 of Tau protein (SEQ ID NO:1)) that has been phosphorylated at positions 396 and 404, such that the amino acid sequence of the preferred immunogen has the amino acid sequence of SEQ ID NO:8: TDHGAEIVYK$\underline{S^{\{P\}}}$ PVVSGDT$\underline{S^{\{P\}}}$ PRHL. The underlined serine residues at positions 11 and 19 of SEQ ID NO:7, and the underlined phosphoserine residues at positions 11 and 19 of SEQ ID NO:8 correspond to positions 396 and 404 of Tau (SEQ ID NO:1). The employed immunogen contained this peptide, and is preferably modified to contain an N-terminal cysteine residue that is conjugated to keyhole limpet hemocyanin (KLH). Such efforts led to the isolation of Antibody 4E6G7 (also referred to as Antibody 4E6), which immunospecifically binds to the $^{\{P\}}$Ser404 Epitope (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance*," J. Biol. Chem. 288:35452-35465; Gu, J. et al. (2013) "*Two Novel Tau Antibodies Targeting The 396/404 Region Are Primarily Taken Up By Neurons And Reduce Tau Protein Pathology*," J. Biol. Chem. 288(46):33081-33095).

As discussed below, Antibody 4E6G7 exhibits a desirable spectrum of functionalities, including in particular, acute antibody-mediated improvement in cognition relates to clearance of soluble phospho-tau and a high affinity binding to solubilized PHF. One aspect of the present invention relates to the recognition that therapeutic efficacy in treating tauopathy positively correlates with an antibody's affinity for solubilized PHF. Thus, in addition to providing Antibody 4E6G7, the invention provides a method for isolating additional therapeutically effective antibody species, in which such antibodies are obtained by screening anti-Tau antibodies for those that exhibit high affinity for solubilized PHF.

B. Antibody 4E6G7

The Light Chain Variable Domain of Antibody 4E6G7 has the amino acid sequence (SEQ ID NO:9; CDRs are underlined):

```
DIQMNQSPSS LSASLGDTIT ISCHASQNIN VWLSWYQQKP

GNIPKLLIFE ASTLYTGVPS RFSGSGSGTG FTLTISSLQP

EDIATYYCQQ GQSYPWTFGG GTKLEIKR
```

The Light Chain Variable Domain CDR1 of Antibody 4E6G7 thus has the amino acid sequence (SEQ ID NO:10): HASQNINVWLS The Light Chain Variable Domain CDR2 of Antibody 4E6G7 thus has the amino acid sequence (SEQ ID NO:11): EASTLYT The Light Chain Variable Domain CDR3 of Antibody 4E6G7 thus has the amino acid sequence (SEQ ID NO:12): QQGQSYPWT The Heavy Chain Variable Domain of Antibody 4E6G7 has the amino acid sequence (SEQ ID NO:13; CDRs are underlined):

```
VQLQQSGAEL VQPGASVKLS CTASGFNIKD TSMHWVRQRP

EQGLEWIGRI APANGNTKYD PKFQGKATIT TDTSSNTAYL

QLSSLTSEDT AVYYCSGSGN YDWGQGTTLT VS
```

Thus, the Heavy Chain Variable Domain CDR1 of Antibody 4E6G7 has the amino acid sequence (SEQ ID NO:14): GFNIKDTSMH Thus, the Heavy Chain Variable Domain CDR2 of Antibody 4E6G7 has the amino acid sequence (SEQ ID NO:15): RIAPANGNTKYDPKFQG Thus, the Heavy Chain Variable Domain CDR3 of Antibody 4E6G7 has the amino acid sequence (SEQ ID NO:16): SGNYD C. scFv Molecules scFv molecules may be generated from Antibody 4E6G7, and thus possess the same Light and Heavy Chain Variable Domains CDR1, CDR2 and CDR3 as Antibody 4E6G7.

The complete sequence of an exemplary scFv is (SEQ ID NO:17) (CDR residues are underlined):

```
DIQMNQSPSS LSASLGDTIT ISCHASQNIN VWLSWYQQKP

GNIPKLLIFE ASTLYTGVPS RFSGSGSGTG FTLTISSLQP

EDIATYYCQQ GQSYPWTFGG GTKLEIKRss ggggsggggg gssrssVQLQ QSGAELVQPG ASVKLSCTAS GFNIKDTSMH

WVRQRPEQGL EWIGRIAPAN GNTKYDPKFQ GKATITTDTS

SNTAYLQLSS LTSEDTAVYY CSGSGNYDWG QGTTLTVS
``` wherein amino acid residues 1-108 are the amino acid residues of the Light Chain Variable Domain of Antibody 4E6G7 (SEQ ID NO:9), amino acid residues 109-126 are the amino acid residues of the linker (SEQ ID NO:4) (shown in lowercase italics), and amino acid residues 127-238 are the amino acid residues of the Heavy Chain Variable Domain of Antibody 4E6G7 (SEQ ID NO:13).

In a preferred embodiment, an exemplary scFv is prepared as a fusion protein that includes an N-terminal leader peptide portion having the amino acid sequence (SEQ ID NO:18): IQEEFKMKKTAIAIAVALAGFATVAQAA, and/or a C-terminal peptide portion. The C-terminal peptide portion may include: an antibody constant domain, such as (SEQ ID NO:19): AKTTPPSVTSGQAGQ (Hussein, A. H. et al. (2007) "*Construction and Characterization of Single-Chain Variable Fragment Antibodies Directed against the Bordetella pertussis Surface Adhesins Filamentous Hemagglutinin and Pertactin*," Infect. Immun. 75(11):5476-5482), a His-Tag, such as (SEQ ID NO:5): HHHHHH), and/or an HA-Tag such as (SEQ ID NO:6): GAYPYDVPDYAS, or any combination or sub-combination thereof, and in any order. A preferred C-terminal peptide portion has the amino acid sequence (SEQ ID NO:20): AKTTPPSVTSGQAGQHHHHHHGAYPYDVPDYAS, and thus includes (in the N-terminus to C-Terminus direction) SEQ ID NO:19, SEQ ID NO:5, and SEQ ID NO:6.

Thus, in preferred embodiments, exemplary scFv fusion proteins will comprise the amino acid sequence of any of SEQ ID NOs:21-29 (in which the N-terminal and/or C-Terminal peptide portions of the ScFv fusion are underlined):

```
SEQ ID NO: 21 (a fusion of SEQ ID NOs: 18 and 17):
IQEEFKMKKT AIAIAVALAG FATVAQAADI QMNQSPSSLS

ASLGDTITIS CHASQNINVW LSWYQQKPGN IPKLLIFEAS

TLYTGVPSRF SGSGSGTGFT LTISSLQPED IATYYCQQGQ

SYPWTFGGGT KLEIKRSSGG GGSGGGGGS SRSSVQLQQS

GAELVQPGAS VKLSCTASGF NIKDTSMHWV RQRPEQGLEW

IGRIAPANGN TKYDPKFQGK ATITTDTSSN TAYLQLSSLT

SEDTAVYYCS GSGNYDWGQG TTLTVS

SEQ ID NO: 22 (a fusion of SEQ ID NOs: 17 and 19):
DIQMNQSPSS LSASLGDTIT ISCHASQNIN VWLSWYQQKP

GNIPKLLIFE ASTLYTGVPS RFSGSGSGTG FTLTISSLQP

EDIATYYCQQ GQSYPWTFGG GTKLEIKRss ggggsggggg gssrssVQLQ QSGAELVQPG ASVKLSCTAS GFNIKDTSMH

WVRQRPEQGL EWIGRIAPAN GNTKYDPKFQ GKATITTDTS

SNTAYLQLSS LTSEDTAVYY CSGSGNYDWG QGTTLTVSAK

TTPPSVTSGQ AGQ

SEQ ID NO: 23 (a fusion of SEQ ID NOs: 17 and 5):
DIQMNQSPSS LSASLGDTIT ISCHASQNIN VWLSWYQQKP

GNIPKLLIFE ASTLYTGVPS RFSGSGSGTG FTLTISSLQP

EDIATYYCQQ GQSYPWTFGG GTKLEIKRss ggggsggggg gssrssVQLQ QSGAELVQPG ASVKLSCTAS GFNIKDTSMH

WVRQRPEQGL EWIGRIAPAN GNTKYDPKFQ GKATITTDTS

SNTAYLQLSS LTSEDTAVYY CSGSGNYDWG QGTTLTVSHH

HHHH

SEQ ID NO: 24 (a fusion of SEQ ID NOs: 17 and 6):
DIQMNQSPSS LSASLGDTIT ISCHASQNIN VWLSWYQQKP

GNIPKLLIFE ASTLYTGVPS RFSGSGSGTG FTLTISSLQP

EDIATYYCQQ GQSYPWTFGG GTKLEIKRss ggggsggggg gssrssVQLQ QSGAELVQPG ASVKLSCTAS GFNIKDTSMH

WVRQRPEQGL EWIGRIAPAN GNTKYDPKFQ GKATITTDTS

SNTAYLQLSS LTSEDTAVYY CSGSGNYDWG QGTTLTVSGA

YPYDVPDYAS

SEQ ID NO: 25 (a fusion of SEQ ID NOs: 17 and 20):
DIQMNQSPSS LSASLGDTIT ISCHASQNIN VWLSWYQQKP

GNIPKLLIFE ASTLYTGVPS RFSGSGSGTG FTLTISSLQP

EDIATYYCQQ GQSYPWTFGG GTKLEIKRss ggggsggggg gssrssVQLQ QSGAELVQPG ASVKLSCTAS GFNIKDTSMH

WVRQRPEQGL EWIGRIAPAN GNTKYDPKFQ GKATITTDTS

SNTAYLQLSS LTSEDTAVYY CSGSGNYDWG QGTTLTVSAK

TTPPSVTSGQ AGQHHHHHHG AYPYDVPDYA S

SEQ ID NO: 26 (a fusion of SEQ ID NOs: 18, 17 and 19):
IQEEFKMKKT AIAIAVALAG FATVAQAADI QMNQSPSSLS

ASLGDTITIS CHASQNINVW LSWYQQKPGN IPKLLIFEAS

TLYTGVPSRF SGSGSGTGFT LTISSLQPED IATYYCQQGQ

SYPWTFGGGT KLEIKRSSGG GGSGGGGGS SRSSVQLQQS

GAELVQPGAS VKLSCTASGF NIKDTSMHWV RQRPEQGLEW

IGRIAPANGN TKYDPKFQGK ATITTDTSSN TAYLQLSSLT

SEDTAVYYCS GSGNYDWGQG TTLTVSAKTT PPSVTSGQAG Q

SEQ ID NO: 27 (a fusion of SEQ ID NOs: 18, 17 and 5):
IQEEFKMKKT AIAIAVALAG FATVAQAADI QMNQSPSSLS

ASLGDTITIS CHASQNINVW LSWYQQKPGN IPKLLIFEAS

TLYTGVPSRF SGSGSGTGFT LTISSLQPED IATYYCQQGQ

SYPWTFGGGT KLEIKRSSGG GGSGGGGGS SRSSVQLQQS

GAELVQPGAS VKLSCTASGF NIKDTSMHWV RQRPEQGLEW

IGRIAPANGN TKYDPKFQGK ATITTDTSSN TAYLQLSSLT

SEDTAVYYCS GSGNYDWGQG TTLTVSHHHH HH

SEQ ID NO: 28 (a fusion of SEQ ID NOs: 18, 17 and 6):
IQEEFKMKKT AIAIAVALAG FATVAQAADI QMNQSPSSLS

ASLGDTITIS CHASQNINVW LSWYQQKPGN IPKLLIFEAS

TLYTGVPSRF SGSGSGTGFT LTISSLQPED IATYYCQQGQ

SYPWTFGGGT KLEIKRSSGG GGSGGGGGS SRSSVQLQQS

GAELVQPGAS VKLSCTASGF NIKDTSMHWV RQRPEQGLEW
```

```
                          -continued
IGRIAPANGN TKYDPKFQGK ATITTDTSSN TAYLQLSSLT

SEDTAVYYCS GSGNYDWGQG TTLTVSGAYP YDVPDYAS

SEQ ID NO: 29 (a fusion of SEQ ID NOs: 18, 17 and
20):
IQEEFKMKKT AIAIAVALAG FATVAQAADI QMNQSPSSLS

ASLGDTITIS CHASQNINVW LSWYQQKPGN IPKLLIFEAS

TLYTGVPSRF SGSGSGTGFT LTISSLQPED IATYYCQQGQ

SYPWTFGGGT KLEIKRSSGG GGSGGGGGS SRSSVQLQQS

GAELVQPGAS VKLSCTASGF NIKDTSMHWV RQRPEQGLEW

IGRIAPANGN TKYDPKFQGK ATITTDTSSN TAYLQLSSLT

SEDTAVYYCS GSGNYDWGQG TTLTVSAKTT PPSVTSGQAG

QHHHHHHGAY PYDVPDYAS
```

Although scFv are able to transit across the blood-brain barrier, various ancillary approaches may be used to further promote such transit (Huang, L. et al. (2013) "*Single-Chain Fragment Variable Passive Immunotherapies For Neurodegenerative Diseases*," Int. J. Mol. Sci. 14(9):19109-19127). A limited set of proteins and peptides are transported across the blood-brain barrier via receptor-mediated transcytosis (Hervé, F. et al. (2008) "*CNS Delivery Via Adsorptive Transcytosis*," AAPS J. 10(3):455-472), the three best-studied ligands being insulin, iron-transferrin and LDL-cholesterol (Bickel, U. et al. (2001) "*Delivery Of Peptides And Proteins Through The Blood-Brain Barrier*," Adv. Drug Deliv. Rev. 46:247-279; Tuma, P. L. et al. (2003) "*Transcytosis: Crossing Cellular Barriers*," Physiol. Rev. 83:871-932). Thus, transport of an scFv across the blood-brain barrier can be promoted by fusing the scFv to an antibody, or an epitope-binding fragment thereof, that is immunospecific for a receptor of such ligands (e.g., the human insulin receptor (HIR), the transferrin receptor (TfR), low density lipoprotein receptor-related proteins 1 (LRP1) and 2 (LRP2), non-toxic diphtheria toxin receptor/Heparin binding epidermal growth factor-like growth factor, etc.). The resulting fusion protein can be transported across the blood-brain barrier through its binding to the receptor (Boado, R. J. et al. (2010) "*IgG-Single-Chain Fv Fusion Protein Therapeutic For Alzheimer's Disease: Expression In CHO cells And Pharmacokinetics And Brain Delivery In The Rhesus Monkey*," Biotechnol. Bioeng. 105:627-635; Jones, A. R. et al. (2007) "*Blood-Brain Barrier Transport Of Therapeutics Via Receptor-Mediation*," Pharm. Res. 24(9):1759-1771; Wang, Y. Y. et al. (2009) "*Receptor-Mediated Therapeutic Transport Across The Blood-Brain Barrier*," Immunotherapy 1(6):983-993; Lajoie, J. M. et al. (2015) "*Targeting Receptor-Mediated Transport For Delivery Of Biologics Across The Blood-Brain Barrier*," Annu. Rev. Pharmacol. Toxicol. 55:613-631; Pardridge, W. M. (2102) "*Drug Transport Across The Blood-Brain Barrier*," J. Cereb. Blood Flow Metab. 32(11):1959-1972; Bhaskar, S. et al. (2010) "*Multifunctional Nanocarriers For Diagnostics, Drug Delivery And Targeted Treatment Across Blood-Brain Barrier: Perspectives On Tracking And Neuroimaging*," Part. Fibre. Toxicol. 7:3 pp. 1-25).

The scFv may be augmented to contain a polycationic peptide that facilitates adsorptive-mediated transcytosis. Suitable polycationic peptides include hexamethylene-diamine, putrescine, spermidine and spermine (Hervé, F. et al. (2008) "*CNS Delivery Via Adsorptive Transcytosis*," AAPS J. 10(3):455-472; Kandimalla, K. K. et al. (2006) "*Physi-ological And Biophysical Factors That Influence Alzheimer's Disease Amyloid Plaque Targeting Of Native And Putrescine Modified Human Amyloid Beta40*," J. Pharmacol. Exp. Ther. 318:17-25). The scFv may be augmented to comprise polycationic groups via treatment that amidates some or all of its carboxylic groups (i.e., the carboxyterminal group, or the carboxylic side chains of glutamate or aspartate residue(s) of the scFv).

Alternatively, the scFv may be augmented to contain a cell-penetrating peptide ("CPP") (Rao, K. S. et al. (2009) "*Targeting Anti-HIV Drugs To The CNS*," Expert Opin. Drug Deliv. 6(8):771-784; Mathupala, S. P. et al. (2009) "*Delivery Of Small-Interfering RNA (siRNA) To The Brain*," Expert Opin. Ther. Pat. 19(2):137-140; Hervé, F. et al. (2008) "*CNS Delivery Via Adsorptive Transcytosis*," AAPS J. 10(3):455-472). Such peptides include the HIV-1 trans-activating transcriptional activator (TAT) peptide, the Herpes Simplex Virus type-1 transcription factor (HSV VP-22) peptide, antennapedia and penetratin (Wadia, J. S. et al. (2004) "*Transducible TAT-HA Fusogenic Peptide Enhances Escape Of TAT-Fusion Proteins After Lipid Raft Macropinocytosis*," Nat. Med. 10:310-315; Richard, J. P. et al. (2003) "*Cell-Penetrating Peptides. A Reevaluation Of The Mechanism Of Cellular Uptake*," J. Biol. Chem. 278:585-590; Temsamani, J. et al. (2004) "*The Use Of Cell-Penetrating Peptides For Drug Delivery,*" Drug Discov. Today 9:1012-1019).

III. Uses of the Antibodies and Antibody Fragments of the Present Invention

The present invention relates to the use of antibody-based molecules that are immunospecific for the $^{\{P\}}$Ser404 Epitope to diagnose and/or treat Alzheimer's disease or tauopathy in a subject patient. With respect to such diagnostic utility, such uses may involve detecting, in the subject (i.e., in vivo), the presence of a pathological Tau conformer using, for example, Antibody 4E6G7, or a $^{\{P\}}$Ser404 Epitope-binding fragment thereof (especially an scFv fragment thereof), that has preferably been detectably labeled (such molecules being collectively referred to herein as the diagnostic molecules of the present invention). Alternatively, such uses may involve detecting the presence of a pathological Tau conformer ex vivo (e.g., in a biopsy sample, or post-mortem) using the diagnostic molecules of the present invention.

In one embodiment, the $^{\{P\}}$Ser404 Epitope-specific antibody-based molecules of the present invention may be humanized antibodies.

With respect to the therapeutic utility of the $^{\{P\}}$Ser404 Epitope-specific antibody-based molecules of the present invention, such utility may involve the administration of a therapeutically effective amount of such an antibody-based molecule (e.g., Antibody 4E6G7, and more particularly, an scFv fragment thereof) to a patient having one or more symptoms of Alzheimer's disease or such tauopathy, and thus in need of such therapy, or it may involve the administration of a prophylactically effective amount of such antibody-based molecules to a patient not exhibiting such symptoms, or exhibiting symptoms of mild dementia or pre-tauopathy that is indicative of incipient Alzheimer's disease or tauopathy, such molecules being collectively referred to herein as the therapeutic molecules of the present invention.

The $^{\{P\}}$Ser404 Epitope-specific antibody-based molecules of the present invention may be used in concert for diagnostic and/or therapeutic purposes with antibodies and antibody-based molecules having immunospecificity for epitopes other than the $^{\{P\}}$Ser404 Epitope.

IV. Production of the Tau-Binding Molecules of the Present Invention

The Tau-binding molecules of the present invention are preferably produced via the recombinant expression of a nucleic acid molecule that encodes their constituent polypeptide chain(s). The invention thus accordingly also relates to an expression vector encoding such one or more polypeptide chains of an antibody of the invention or a fragment thereof.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-Tau antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., MoI Ther 3, 793-800 (2001)), or as a precipitated nucleic acid vector construct, such as a CaPO4-precipitated construct (as described in, for instance, WO 00/46147, Benvenisty and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well-known in the art (see for instance U.S. Pat. Nos. 5,589,466 and 5,973,972).

In one embodiment, the vector is suitable for the expression of a $^{\{P\}}$Ser404 Epitope-specific antibody-based molecule of the present invention in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison, Wis.) and the like). An expression vector may also or alternatively be a vector suitable for expression of such antibody-based molecules in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. CURRENT PROTOCOLS IN MOLECULAR BIOLOGY, Greene Publishing and Wiley InterScience New York (1987), and Grant et al., Methods in Enzymol 153, 516-544 (1987)).

In an expression vector of the invention, a nucleic acid molecule encoding a $^{\{P\}}$Ser404 Epitope-specific antibody-based molecule of the present invention may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, that produces a $^{\{P\}}$Ser404 Epitope-specific antibody-based molecule of the present invention. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of a $^{\{P\}}$Ser404 Epitope-specific antibody-based molecule of the present invention. In another embodiment, the present invention provides a cell comprising a non-integrated nucleic acid, such as a plasmid, cosmid, phagemid, or linear expression element, that which comprises a sequence coding for expression of a $^{\{P\}}$Ser404 Epitope-specific antibody-based molecule of the present invention.

In a further aspect, the invention relates to a method for producing a $^{\{P\}}$Ser404 Epitope-specific antibody-based molecule of the present invention, said method comprising the steps of a) culturing a hybridoma or a host cell of the invention as described herein above, and b) purifying the antibody of the invention from the culture media.

In general, a $^{\{P\}}$Ser404 Epitope-specific antibody-based molecule of the present invention may be modified by inclusion of any suitable number of modified amino acids and/or associations with such conjugated substituents. Suitability in this context is generally determined by the ability to at least substantially retain the immunospecificity for the $^{\{P\}}$Ser404 Epitope associated with the non-derivatized parent anti-Tau antibody. The presence of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) *Protein Protocols On CD-Rom*, Humana Press, Totowa, N.J. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

As indicated above, when it is desired to increase the half-life of an administered therapeutic molecule of the present invention, such molecules may be formed to comprise carbohydrate moieties, such as polyoxyethylated polyols or polyethylene glycol (PEG) (e.g., a PEG with a molecular weight of between about 1,000 and about 40,000, such as between about 2,000 and about 20,000, e.g., about 3,000-12,000 g/mol) (Moosmann, A. et al. (2014) "*Purification Of PEGylated Proteins, With The Example Of PEGylated Lysozyme and PEGylated scFv,*" Methods Mol. Biol. 1129:527-538; Jevsevar, S. et al. (2010) "*PEGylation Of Therapeutic Proteins,*" Biotechnol. J. 5:113-228), or through glycosylation or by adding or associating proteins such as human serum albumin (Müller, M. R. et al. (2012) "*Improving The Pharmacokinetic Properties Of Biologics By Fusion*

To An Anti-HSA Shark VNAR Domain," MAbs. 4(6):673-685; Stork, R. et al. (2008) "N-Glycosylation As Novel Strategy To Improve Pharmacokinetic Properties Of Bispecific Single-Chain Diabodies," J. Biol. Chem. 283:7804-7812; Alt, M. et al. (1999) "Novel Tetravalent And Bispecific IgG-like Antibody Molecules Combining Single-Chain Diabodies With The Immunoglobulin Gammal Fc or CH3 Region," FEBS Lett. 454:90-94; Peters T. et al. (1985) "Serum Albumin," Adv. Protein Chem. 37:161-245). Illustrative polymers and methods to attach them to peptides, are known, (see, for example, U.S. Pat. Nos. 4,766,106; 4,179,337; 4,495,285 and 4,609,546).

V. Pharmaceutical Compositions of the Present Invention

The $^{\{P\}}$Ser404 Epitope-specific antibody-based molecules of the present invention are advantageously administered as pharmaceutical compositions comprising an active therapeutic agent and one or more of a variety of other pharmaceutically acceptable components. See REMINGTON: THE SCIENCE AND PRACTICE OF PHARMACY (21$^{st}$ Edition) (2005) (Troy, D. B. et al. (Eds.) Lippincott Williams & Wilkins (Publs.), Baltimore Md.), which is hereby incorporated by reference in its entirety. The preferred form depends on the intended mode of administration and therapeutic application. The compositions can also include, depending on the formulation desired, pharmaceutically acceptable, non-toxic carriers, excipients, diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition, and which are vehicles commonly used to formulate pharmaceutical compositions for animal or human administration. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well-known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Suitability for carriers and other components of pharmaceutical compositions is determined based on the lack of significant negative impact on the desired biological properties of the chosen compound or pharmaceutical composition of the present invention (e.g., less than a substantial impact (e.g., 10% or less relative inhibition, 5% or less relative inhibition, etc.)) on antigen binding.

The pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well-known in the art. Methods for the preparation of such formulations are generally known to those skilled in the art. See, e.g., SUSTAINED AND CONTROLLED RELEASE DRUG DELIVERY SYSTEMS, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

For parenteral administration, agents of the present invention are typically formulated as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention can be administered in the form of a depot injection or implant preparation which can be formulated in such a manner as to permit a sustained release of the active ingredient. An exemplary composition comprises an scFv at about 5 mg/mL, formulated in aqueous buffer consisting of 50 mM L-histidine, 150 mM NaCl, adjusted to pH 6.0 with HCl.

Typically, compositions are thus prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, et al., Science 249:1527 (1990); Hanes, et al., Advanced Drug Delivery Reviews 28:97-119 (1997), which are hereby incorporated by reference in their entirety). Additional formulations suitable for other modes of administration include oral, intranasal, and pulmonary formulations, suppositories, and transdermal applications.

VI. Administration of the Pharmaceutical Compositions of the Present Invention

The molecules of the present invention can be administered by parenteral, topical, oral or intranasal means for prophylactic and/or therapeutic treatment. Intramuscular injection (for example, into the arm or leg muscles) and intravenous infusion are preferred methods of administration of the molecules of the present invention. In some methods, such molecules are administered as a sustained release composition or device, such as a Medipad™ device (Elan Pharm. Technologies, Dublin, Ireland). In some methods, the molecules of the present invention are injected directly into a particular tissue where deposits have accumulated, for example intracranial injection.

In one embodiment, a pharmaceutical composition of the present invention is administered parenterally. The phrases "parenteral administration" and "administered parenterally" as used herein denote modes of administration other than enteral and topical administration, usually by injection, and include epidermal, intravenous, intramuscular, intraarterial, intrathecal, intracapsular, intracranial, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection, subcutaneous and infusion. In one embodiment that pharmaceutical composition is administered by intravenous or subcutaneous injection or infusion.

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presented during development of the disease.

In therapeutic applications (i.e., in applications involving a patient who has been diagnosed as having Alzheimer's disease or other tauopathy) the therapeutic molecules of the present invention are administered to such patient in an amount sufficient to cure, treat, or at least partially arrest, the symptoms of the disease (as adduced by biochemical, histologic and/or behavioral assessment), including its complications and intermediate pathological phenotypes in development of the disease. In some embodiments, the administration of the therapeutic molecules of the present invention reduces or eliminates mild cognitive impairment in patients that have not yet developed characteristic Alzheimer's pathology.

Effective doses of the provided therapeutic molecules of the present invention, for the treatment of the above-described conditions may vary depending upon many different factors, including means of administration, target site, physiological state of the patient, other medications administered, and whether treatment is prophylactic or therapeutic. Treatment dosages are typically titrated to optimize their safety and efficacy. On any given day that a dosage is given, the dosage may range from about 0.0001 to about 100 mg/kg, and more usually from about 0.01 to about 5 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight.

A physician or veterinarian having ordinary skill in the art may readily determine and prescribe the effective amount of the pharmaceutical composition required. For example, the physician or veterinarian could start doses of the anti-Tau antibody or fragment employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

An exemplary treatment regime entails administration once per every two weeks or once a month or once every 3 to 6 months. In some methods, one, two or more antibodies (or epitope-binding fragments thereof) will be administered in conjunction with the administration of the therapeutic molecules of the present invention, in which case the dosage of each such administered molecule falls within the ranges indicated.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered such therapeutic molecule using a prophylactic dosage regime.

For therapeutic purposes, the molecules of the present invention are usually administered on multiple occasions. Intervals between single dosages (e.g., a bolus or infusion) can be weekly, monthly, or yearly. In some methods, dosage is adjusted to achieve a plasma concentration of 1-1000 µg/mL and in some methods 25-300 µg/mL. Alternatively, the therapeutic molecules of the present invention can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and non-human antibodies. scFv molecules generally have short serum half-lives.

Another aspect of the present invention is a combination therapy wherein an additional antibody, or an epitope-binding fragment thereof, recognizing the Tau protein, or an immunogenic epitope thereof, is administered in combination with a therapeutic molecule of the present invention. In the case of amyloidogenic diseases such as, Alzheimer's disease and Down's syndrome, immune modulation to clear amyloid-beta (Aβ) deposits is an emerging therapy. Immunotherapies targeting Aβ have consistently resulted in cognitive improvements. It is likely that Tau and Aβ pathologies are synergistic. Therefore, a combination therapy targeting the clearance of both pathologies at the same time may be more effective than targeting each individually. In the case of Parkinson's Disease and related neurodegenerative diseases, immune modulation to clear aggregated forms of the α-synuclein protein is also an emerging therapy. A combination therapy which targets the clearance of both Tau and α-synuclein proteins simultaneously may be more effective than targeting each individually.

VII. Utility of the Tau-Binding Molecules of the Present Invention

D. Diagnostic Utility

Detecting the presence of a pathological Tau conformer in a subject using a $^{\{P\}}$Ser404 Epitope-specific antibody-based diagnostic molecule of the present invention can be achieved by obtaining a biological sample from the subject (e.g., blood, urine, cerebral spinal fluid), contacting the biological sample with said diagnostic antibody, and detecting binding of the diagnostic molecule to a pathological Tau protein conformer in the sample from the subject. Assays for carrying out the detection of a pathological Tau protein in a biological sample that may be readily adapted to the detection of the diagnostic molecules of the present invention are well-known in the art and include, without limitation, ELISA, immunohistochemistry, Western blot, etc.

Alternatively, detecting the presence of a pathological Tau protein conformer in a subject using a $^{\{P\}}$Ser404 Epitope-specific antibody-based diagnostic molecule of the present invention can be achieved using in vivo imaging techniques. In vivo imaging involves administering to the subject the diagnostic antibody having antigenic specificity for a pathological Tau peptide and detecting binding of the diagnostic antibody reagent to the pathological Tau protein conformer in vivo.

The $^{\{P\}}$Ser404 Epitope-specific antibody-based diagnostic molecules of the present invention can be administered by injection (e.g., intravenous injection, intracarotid injection, etc.) into the body of the patient, or directly into the brain by intracranial injection. The dosage of such molecule should be from about 0.0001 mg/kg to about 100 mg/kg, and more usually from about 0.01 mg/kg to about 5 mg/kg, of the host body weight. For example, dosages can be about 1 mg/kg body weight or about 10 mg/kg body weight or within the range of about 1-10 mg/kg.

Typically, a $^{\{P\}}$Ser404 Epitope-specific antibody-based diagnostic molecule of the present invention is labeled, although in some methods, the molecule may be unlabeled and a secondary labeling agent is used to bind to such molecule (coupled or conjugated either directly to the molecule or indirectly, through an intermediate (such as, for example, a linker known in the art) using techniques known in the art). The choice of label depends on the means of detection. For example, a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, is suitable for optical detection. Chemoluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/ biotin and avidin/biotin. Paramagnetic labels and radioisotopic labels can also be employed, and are preferably detected using Positron Emission Tomography (PET) or Single-Photon Emission Computed Tomography (SPECT). Radiolabels include, but are not limited to, bismuth ($^{213}$Bi), carbon ($^{11}$C, $^{13}$C, $^{14}$C), chromium ($^{51}$Cr), cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho), hydrogen ($^{3}$H), indium ($^{111}$In, $^{112}$In, $^{113}$In,) $^{115}$In), iodine ($^{121}$I, $^{123}$I, $^{125}$I, $^{131}$I), iridium ($^{192}$Ir), iron ($^{59}$Fe), krypton ($^{81m}$Kr), lanthanum (140La), lutetium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium ($^{186}$Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y) and zinc ($^{65}$Zn); positron emitting metals using various positron emission tomographies, and non-radioactive paramagnetic metal ions (such as paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581; 4,735,210; 5,101,827; 5,102,990; RE 35,500; 5,648,471 and 5,697,902. For example, a radioisotope may be conjugated by a chloramine-T method (Lindegren, S. et al. (1998) "Chloramine-T In High-Specific-Activity Radioiodination Of Antibodies Using N-Succinimidyl-3-(Trimethylstannyl) Benzoate As An Intermediate," Nucl. Med. Biol. 25(7):659-665; Kurth, M. et al. (1993) "Site-Specific Conjugation Of A Radioiodinated Phenethylamine Derivative To A Monoclonal Antibody Results In Increased Radioactivity Localization In Tumor," J. Med. Chem. 36(9):1255-1261; Rea, D. W. et al. (1990) "Site-specifically radioiodinated antibody for targeting tumors," Cancer Res. 50(3 Suppl):857s-861s).

Diagnosis is performed by comparing the number, size, and/or intensity of labeled pathological Tau conformers, Tau aggregates, and/or neurofibrillary tangles in a sample from the subject, or in the subject, to corresponding baseline values. The base line values can represent the mean levels in a population of non-diseased individuals. Baseline values can also represent previous levels determined in the same subject.

The diagnostic methods described above can also be used to monitor a subject's response to therapy. In this embodiment, detecting the presence of pathological Tau in a subject is determined prior to the commencement of treatment. The level of pathological Tau in the subject at this time point is used as a baseline value. At various times during the course of treatment the detection of pathological Tau protein conformers, Tau aggregates, and/or neurofibrillary tangles is repeated, and the measured values thereafter compared with the baseline values. A decrease in values relative to baseline signals a positive response to treatment. Values can also increase temporarily in biological fluids as pathological Tau is being cleared from the brain.

The present invention is further directed to a kit for performing the above-described diagnostic and monitoring methods. Typically, such kits contain the diagnostic antibody of the present invention. The kit can also include a detectable label. The diagnostic antibody itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring pathological Tau protein in a biological sample, the antibodies of the kit may be supplied pre-bound to a solid phase, such as to the wells of a microtiter dish.

The presence of labeled anti-Tau antibodies or their Tau-binding fragments may be detected in vivo for diagnosis purposes. In one embodiment, such diagnosis comprises: a) administering to a subject an effective amount of such labeled molecule; b) waiting for a time interval following administration in order to allow the labeled molecule to concentrate at sites (if any) of aggregated Tau and to allow unbound labeled molecule to be cleared to a background level; c) determining a background level; and d) detecting such labeled molecule in the subject, such that detection of labeled molecule above the background level is indicative that the subject has a tauopathy, or is indicative of the severity of such tauopathy. In accordance with such embodiment, the antibody is labeled with an imaging moiety suitable for detection using a particular imaging system known to those skilled in the art. Background levels may be determined by various methods known in the art, including comparing the amount of labeled molecule detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MM), and sonography.

E. Therapeutic Utility

As indicated above, one aspect of the present invention relates to a method of preventing or treating Alzheimer's disease or other tauopathy in a subject via the administration of an effective amount of a $^{\{P\}}$Ser404 Epitope-specific antibody-based molecule of the present invention (especially Antibody 4E6G7 or an scFv fragment thereof) in an amount effective to prevent or treat such Alzheimer's disease or other tauopathy. Such administration may be provided in order to promote the clearance of Tau aggregates from the brain of a subject or may be provided in order to slow a tangle-related behavioral phenotype in a subject. Additionally, such administration may be provided prophylactically in order to delay, impede, attenuate or prevent the onset of Alzheimer's disease, or other tauopathy associated with the neurofibrillary tangle.

The term "treatment" or "treating" as used herein means ameliorating, slowing or reversing the progress or severity of a disease or disorder, or ameliorating, slowing or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," when applied to an antibody of the invention, refers to an amount sufficient, at dosages and for periods of time necessary, to achieve an intended biological effect or a desired therapeutic result including, without limitation, clinical results. The phrase "therapeutically effective amount" when applied to an antibody of the invention is intended to denote an amount of the antibody that is sufficient to ameliorate, palliate, stabilize, reverse, slow or delay the progression of a disorder or disease state, or of a symptom of the disorder or disease. In an embodiment, the method of the present invention provides for administration of the antibody in combinations with other compounds. In such instances, the "effective amount" is the amount of the combination sufficient to cause the intended biological effect.

An amount adequate to accomplish therapeutic or prophylactic treatment is defined, respectively, as a therapeutically effective dose or a prophylactically effective dose. In both prophylactic and therapeutic regimes, agents are usually administered in several dosages until a sufficient immune response has been achieved. Typically, the immune response is monitored and repeated dosages are given if the immune response starts to wane. A therapeutically effective or prophylactically effective dose of such an antibody or epitope-binding fragment thereof may vary according to factors such as the disease state, age, sex, and weight of the individual, and the ability of the molecule to elicit a desired response in the subject. A therapeutically effective amount is also one in which any toxic or detrimental effects of the antibody or antibody portion are outweighed by the therapeutically beneficial effect.

Patients amenable to treatment include individuals having Alzheimer's disease or such other tauopathy who show clinically recognized symptoms or indications of such conditions, as well as patients not presently showing symptoms of such conditions. Although Alzheimer's disease is definitively diagnosed only post-mortem biopsy, individuals suffering from Alzheimer's disease are clinically diagnosed using the "*Alzheimer's Disease and Related Disorders Association*" ("ADRDA") Criteria (Carrillo, M. C. et al. (2013) "*Revisiting The Framework Of The National Institute On Aging-Alzheimer's Association Diagnostic Criteria*," Alzheimers Dement. 9(5):594-601; Budson, A. E. et al. (2012) "*New Criteria For Alzheimer Disease And Mild Cognitive Impairment: Implications For The Practicing Clinician*," Neurologist 18(6):356-363; Sarazin, M. et al. (2012) "*Clinical And Research Diagnostic Criteria For Alzheimer's Disease*," Neuroimaging Clin. N. Amer. 22(1): 23-32; Husain, M. M. (2005) "*Clinical Diagnosis And Management Of Alzheimer's Disease*," Neuroimaging Clin. N. Amer. 15(4):767-777; Small, G. W. et al. (1997) "*Diagnosis And Treatment Of Alzheimer Disease And Related Disorders. Consensus Statement Of The American Association For Geriatric Psychiatry, The Alzheimer's Association, And The American Geriatrics Society*," JAMA 278(16): 1363-1371). Such individuals can alternatively be distinguished from those having diseases or conditions that are un-related to Alzheimer's disease or other tauopathy by the presence of correlated risk factors (i.e., one or more factors that have been found to possess greater than 50% coincidence with Alzheimer's disease or such other tauopathy). Such correlated risk factors include the finding that a patient has had relatives who have experienced Alzheimer's disease or such other tauopathy, or present a family history of hypercholesterolemia or atherosclerosis. Such correlated risk factors particularly include the finding that a patient possesses one or more genetic or biochemical markers that have been correlated with (i.e., found to possess greater than 50% coincidence with) the occurrence of such actual disease. Examples of such genetic markers of risk toward Alzheimer's disease include correlated mutations in the APP gene, for example, mutations at position 717 and positions 670 and 671 of the APP gene (referred to as the Hardy and Swedish mutations respectively). Other suitable markers of known genetic risk include correlated mutations in the presenilin genes (PS1 and PS2) and in the ApoE4 gene (Bekris, L. M. et al. (2010) "*Genetics of Alzheimer Disease*," J. Geriatr. Psychiatry Neurol. 23(4):213-227).

Such PS1 mutations include the substitutions: R35Q; A79V; V82L; L85P; V89L; V94M; V96F; V97L; F105I; F105L; F105V; L113P; L113Q; Y115C; Y115D; Y115H; T116I; T116N; P117A; P117L; P117R; P117S; E120D; E120D; E120G; E120K; E123K; N135D; N135S; A136G; M139I; M139I; M139K; M139T; M139V; I143F; I143M; I143N; I143T; I143V; M146I; M146I; M146I; M146L; M146L; M146V; T147I; L153V; Y154C; Y154N; H163R; H163Y; W165C; W165G; L166H; L166P; L166R; S169L; S169P; S170F; L171P; L173F; L173W; L174M; L174R; F175S; F177L; F177S; S178P; G183V; E184D; V191A; G206A; G206D; G206S; G206V; G209E; G209R; G209V; S212Y; I213F; L213L; I213T; H214D; H214Y; G217D; G217R; L219F; L219P; Q222H; Q222R; Q223R; L226F; L226R; I229F; A231T; A231V; M233I; M233L; M233L; M233T; M233V; L235P; L235V; F237I; F237L; K239N; T245P; A246E; L248R; L250S; L250V; Y256S; A260V; V261F; V261L; L262F; C263F; C263R; P264L; G266S; P267L; P267S; R269G; R269H; L271V; V272A; E273A; T274R; R278I; R278K; R278S; R278T; E280A; E280G; L282F; L282R; L282V; P284L; P284S; A285V; L286P; L286V; T291P; E318G; R358Q; S365A; R377M; G378E; G378V; L381V; G384A; F386S; S390I; V391F; L392P; L392V; G394V; N405S; A409T; C410Y; V412I; L418F; L420R; L424F; L424H; L424R; L424V; A426P; A431E; A431V; A434C; L435F; P436Q; P436S; and I439S.

Such PS2 mutations include the substitutions: R29H; G34S; R62C; R62H; R71W; A85V; T122P; T122R; S130L; V139M; N141I; L143H; V148I; R163H; M174V; S175C; Y231C; Q228L; M239V; M230I; A252T; P334R; T430M; and D439A.

Such ApoE4 alleles include the ε4 allele, ε3 allele and ε2 allele (Verghese, P. B. et al. (2011) "*Apolipoprotein E In Alzheimer's Disease And Other Neurological Disorders*," Lancet Neurol. 10(3):241-252).

In addition, a number of diagnostic tests are available for identifying individuals who have Alzheimer's disease. These include measurement of CSF Tau and Aβ42 levels. Elevated Tau and decreased Aβ42 levels signify the presence of Alzheimer's disease.

In the case of Alzheimer's disease, virtually anyone is at risk of suffering from Alzheimer's disease. Therefore, the therapeutic molecules of the present invention can be administered prophylactically to the general population without the need for any assessment of the risk of the subject patient. The present methods are especially useful for the prophylactic treatment of individuals who do have a known genetic risk of Alzheimer's disease. In asymptomatic patients, treatment can begin at any age (e.g., 10, 20, 30). Usually, however, it is not necessary to begin treatment until a patient reaches 40, 50, 60, 70, 80 or 90 years of age. Treatment typically entails the administration of multiple dosages over a period of time. Treatment can be monitored by assaying antibody, or activated T-cell or B cell responses to the therapeutic agent over time. If the response falls, a booster dosage is indicated. In the case of potential Down's syndrome patients, treatment can begin ante-natally by administering the therapeutic agent to the mother during pregnancy or shortly after the patient's birth.

The present invention provides:

1. A $^{\{P\}}$Ser404 Epitope-specific antibody-based molecule.
2. The embodiment of such $^{\{P\}}$Ser404 Epitope-specific antibody-based molecule, wherein the molecule is an antibody.
3. The embodiment of such $^{\{P\}}$Ser404 Epitope-specific antibody-based molecule, wherein the molecule is the Antibody 4E6G7.
4. The embodiment of such $^{\{P\}}$Ser404 Epitope-specific antibody-based molecule, wherein molecule is an scFv or a diabody.
5. The embodiment of any of the above-described binding molecules, wherein the molecule immunospecifically binds to the Tau 396/404 peptide (SEQ ID NO:8): TDHGAEIVYK{P} PVVSGDT{P}SPRHL, wherein the residues 11 and 19 thereof are phosphoserine.
6. The embodiment of any of the above-described binding molecules, wherein the epitope-binding fragment comprises one or more of:
   (a) a Light Chain CDR1 having the amino acid sequence of SEQ ID NO:10;
   (b) a Light Chain CDR2 having the amino acid sequence of SEQ ID NO:11;
   (c) a Light Chain CDR3 having the amino acid sequence of SEQ ID NO:12;
   (d) a Heavy Chain CDR1 having the amino acid sequence of SEQ ID NO:14;
   (e) a Heavy Chain CDR2 having the amino acid sequence of SEQ ID NO:15; or
   (f) a Heavy Chain CDR3 having the amino acid sequence of SEQ ID NO:16.
7. The embodiment of any of the above-described binding molecules, wherein the epitope-binding fragment comprises:
   (a) a Light Chain CDR1 having the amino acid sequence of SEQ ID NO:10;
   (b) a Light Chain CDR2 having the amino acid sequence of SEQ ID NO:11;
   (c) a Light Chain CDR3 having the amino acid sequence of SEQ ID NO:12;
   (d) a Heavy Chain CDR1 having the amino acid sequence of SEQ ID NO:14;
   (e) a Heavy Chain CDR2 having the amino acid sequence of SEQ ID NO:15; and
   (f) a Heavy Chain CDR3 having the amino acid sequence of SEQ ID NO:16.
8. The embodiment of the above-described binding molecule that comprises a Light Chain Variable Domain that has the sequence of SEQ ID NO:9 and a Heavy Chain Variable Domain that has the sequence of SEQ ID NO:13.
9. The embodiment of the above-described binding molecule that comprises a Light Chain Variable Domain that has the sequence of SEQ ID NO:9 and a Heavy Chain Variable Domain that has the sequence of SEQ ID NO:13, wherein the molecule is Antibody 4E6G7.
10. The embodiment of the above-described binding molecule that comprises a Light Chain Variable Domain that has the sequence of SEQ ID NO:9 and a Heavy Chain Variable Domain that has the sequence of SEQ ID NO:13, wherein the molecule is an scFv.
11. The embodiment of the above-described scFv that comprises the sequence of SEQ ID NO:17.
12. The embodiment of any of the above-described binding molecules, which is detectably labeled.
13. The embodiment of any of the above-described detectably labeled binding molecules, wherein the detectable label is a fluorescent label, a chemoluminescent label, a paramagnetic label, a radioisotopic label or an enzyme label.
14. (A) The embodiment of any of the above-described detectably labeled binding molecules for use in the manufacture of a medicament for detecting or measuring the presence or amount of the phosphorylated Tau protein in the brain of, or in a biological sample of, a recipient subject, or
   (B) the use of any of the above-described detectably embodiments of labeled binding molecules for detecting or measuring the presence or amount of the phosphorylated Tau protein in the brain of, or in a biological sample of, a recipient subject.
15. (A) The embodiment of any of the above-described detectably labeled binding molecules for use in the manufacture of a medicament for detecting or measuring the presence or amount of the phosphorylated Tau protein in the brain of, or in a biological sample of, a recipient subject, or
   (B) the use of any of the above-described embodiments of detectably labeled binding molecules for detecting or measuring the presence or amount of the phosphorylated Tau protein in the brain of, or in a biological sample of, a recipient subject;
wherein the detection or measurement comprises in vivo imaging of the binding molecule bound to the phosphorylated Tau protein.
16. (A) The embodiment of any of the above-described detectably labeled binding molecules for use in the manufacture of a medicament for detecting or measuring the presence or amount of the phosphorylated Tau protein the brain of, or in a biological sample of, a recipient subject, or
   (B) the use of any of the above-described embodiments of detectably labeled binding molecules for detecting or measuring the presence or amount of the phosphorylated Tau protein in the brain of, or in a biological sample of, a recipient subject;
wherein the detection or measurement comprises ex vivo imaging of the binding molecule bound to the phosphorylated Tau protein.
17. (A) (1) The embodiment of any of the above-described binding molecules, which is detectably labeled; or
   (2) the embodiment of any of the above-described detectably labeled binding molecules, wherein the detectable label is a fluorescent label, a chemoluminescent label, a paramagnetic label, a radioisotopic label or an enzyme label;
for use in the manufacture of a medicament for diagnosing Alzheimer's disease or another tauopathy of a subject; or
   (B) (1) the use of any of the above-described embodiments of detectably labeled binding molecules for diagnosing Alzheimer's disease or another tauopathy of a subject; or
   (2) the use of any of the above-described embodiments of detectably labeled binding molecules, wherein the detectable label is a fluorescent label, a chemiluminescent label, a paramagnetic label, a radioisotopic label or an enzyme label, for diagnosing Alzheimer's disease or another tauopathy of a subject.

18. (A) (1) The embodiment of any of the above-described binding molecules, which is detectably labeled; or
    (2) the embodiment of any of the above-described detectably labeled binding molecules, wherein the detectable label is a fluorescent label, a chemiluminescent label, a paramagnetic label, a radioisotopic label or an enzyme label;
for use in the manufacture of a medicament for diagnosing Alzheimer's disease or another tauopathy of a subject; or
    (B) (1) the use of any of the above-described embodiments of detectably labeled binding molecules for diagnosing Alzheimer's disease or another tauopathy of a subject; or
    (2) the use of any of the above-described embodiments of detectably labeled binding molecules, wherein the detectable label is a fluorescent label, a chemiluminescent label, a paramagnetic label, a radioisotopic label or an enzyme label, for diagnosing Alzheimer's disease or another tauopathy of a subject;
wherein the medicament is an in vivo medicament that is administered to the subject.

19. (A) (1) The embodiment of any of the above-described binding molecules, which is detectably labeled; or
    (2) the embodiment of any of the above-described detectably labeled binding molecules, wherein the detectable label is a fluorescent label, a chemiluminescent label, a paramagnetic label, a radioisotopic label or an enzyme label;
for use in the manufacture of a medicament for diagnosing Alzheimer's disease or another tauopathy of a subject; or
    (B) (1) the use of any of the above-described embodiments of detectably labeled binding molecules for diagnosing Alzheimer's disease or another tauopathy of a subject; or
    (2) the use of any of the above-described embodiments of detectably labeled binding molecules, wherein the detectable label is a fluorescent label, a chemiluminescent label, a paramagnetic label, a radioisotopic label or an enzyme label, for diagnosing Alzheimer's disease or another tauopathy of a subject;
wherein the medicament is incubated ex vivo with a biopsy sample of the subject.

20. The embodiment of any of such uses, wherein the tauopathy is selected from the group comprising frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

21. A method for isolating antibodies that are therapeutically effective in treating a tauopathy recited in embodiment 20, in which anti-Tau antibodies are screened for species that exhibit high affinity for solubilized PHF.

The present invention reflects the finding that two antibodies—Antibody 4E6G7 and Antibody 6B2G12—raised against the same epitope region of Tau had very different effects on cognition in a mouse model of early stage tauopathy. Both antibodies have phospho-selectivity for the immunogen but differ in many ways. The lower affinity Antibody 4E6G7 is effective in acutely improving spatial learning and memory and reducing soluble phospho-tau, whereas the higher affinity Antibody 6B2G12 is ineffective. Importantly, the data further show identical efficacy differences in a primary neuronal tauopathy culture model treated with paired helical filaments (PHF) isolated from an Alzheimer brain. This indicates that the ex vivo culture model has similar predictive validity as the mouse model despite differences in the measured parameters. Toxicity and tau seeding were both prevented by Antibody 4E6G7 but not by Antibody 6B2G12. Furthermore, Antibody 4E6G7 reduced PHF spreading between neurons. Thus, Antibody 4E6G7's efficacy relates to its high affinity binding to solubilized PHF, whereas the ineffective Antibody 6B2G12 was found to bind mainly to aggregated PHF. Blocking Antibody 4E6G7 uptake into neurons prevented its protective effects if the antibody was administered after PHF had been internalized. Hence, under these conditions, the antibody is working intracellularly. When Antibody 4E6G7 and PHF were administered at the same time, the antibody was protective extracellularly. Since such a scenario mimics the physiology seen in tauopathy, the data indicate that extracellular administration of Antibody 4E6G7 will be therapeutically effective.

As discussed below, modest tau pathology was detected by immunohistochemistry in brains of hTau mice, and the treatment and control groups did not appear to differ. Under such conditions of early stage tau pathology, it is easier to quantitate early tau pathology on western blots than by immunohistochemistry, and on such blots insoluble tau protein was clearly present in the 12-13 month old hTau mice. Neither tau antibody induced changes in insoluble tau levels as measured by human specific tau antibody (CP27), although Antibody 4E6G7 markedly improved spatial learning and memory. Analyses of the soluble tau fraction revealed that these cognitive benefits were associated with reduced levels of phospho-tau protein (PHF-1 reactive). It is likely that under such acute treatment conditions, global changes in insoluble tau levels may not be readily achievable, whereas soluble pathological tau protein should be more amenable to clearance. Indeed, the PHF-1 antibody recognizes a phospho-tau epitope within the same region as Antibody 4E6G7, which may explain why this tau fraction is preferentially cleared. However, it does not appear to be oligomer-specific clearance, as no differences were observed in T22 immunoblots between Antibody 4E6G7 and IgG-treated mice.

A functional rescue of associative fear memory was not observed following acute treatment with either Antibody 4E6G7 or Antibody 6B2G12. There are many possible explanations for this. First, the training protocol used may have been too 'strong' to detect a subtle memory deficit. This may be particularly important because the overall tau pathology that was observed, although present, was mild. In prior studies, associative memory deficits were observed only in aged mice with greater levels of tau pathology (Levenga, J., et al. (2013) "*Tau Pathology Induces Loss Of Gabaergic Interneurons Leading To Altered Synaptic Plasticity And Behavioral Impairments*," Acta Neuropathol. Commun. 1:34).

Despite the different model systems used, the findings obtained from ex vivo and in vivo experiments are consistent and not model dependent, which supports their validity. In both cases, Antibody 4E6G7 shows efficacy in preventing tau pathology and associated toxicity/cognitive impairment, while Antibody 6B2G12 does not.

An insight into the relevant tau species was obtained from ELISA and dot blot studies of antibody binding to soluble, solubilized, or aggregated human tau species. Antibody 4E6G7 recognizes primarily solubilized PHF, in an ELISA and dot blot assay, which may explain lack of more global tau changes in the animals under such acute conditions. Mice at this age with modest tau pathology may be ideal to assess acute effects of therapies, particularly under pairwise cognitive comparison as used herein, which improves the sensitivity of detecting beneficial effects. Such in vivo learning and memory benefits by Antibody 4E6G7 and lack thereof for Antibody 6B2G12 in the htau mice are in agreement with the efficacy results in vivo and in the tauopathy culture model. Interestingly, soluble tau species have recently been linked to LTP and memory in htau mice (Fa, M. et al. (2016) "Extracellular tau oligomers produce an immediate impairment of LTP and memory," Sci. Rep. 6:19393).

Although the ELISA and dot blot assays provided useful information on the tau binding properties of Antibody 4E6G7 and Antibody 6B2G12, the data obtained from confocal imaging was judged to be of greater value in determining the mechanism and possible explanation for the differences in efficacy. With co-incubation in the culture assay, extracellular complexes of exogenous PHF and Antibody 4E6G7 formed as Antibody 4E6G7 binds to soluble PHF. This complex formation neutralized PHF and prevented its uptake. However, with Antibody 6B2G12, such complexes did not form, as Antibody 6B2G12 does not bind well to solubilized PHF, and PHF was detected intraneuronally. This indicates that Antibody 6B2G12 could not prevent PHF uptake and toxicity. These results support the conclusion that antibodies can be beneficial while working in the interstitial space between cells. In the living brain, these tau-antibody complexes could then be taken up and cleared by microglia (Gu, J. et al. (2013) "*Two Novel Tau Antibodies Targeting The 396/404 Region Are Primarily Taken Up By Neurons And Reduce Tau Protein Pathology*," J. Biol. Chem. 288(46):33081-33095; Funk, K. E., et al. (2015) "*Distinct Therapeutic Mechanisms of Tau Antibodies: Promoting Microglial Clearence Versus Blocking Neuronal Uptake*," J. Biol. Chem. 290(35):21652-21662; Luo, W., et al. (2015) "*Microglial Internalization And Degradation Of Pathological Tau Is Enhanced By An Anti-Tau Monoclonal Antibody*," Sci. Rep. 5:11161).

As discussed below, addition of 10 or 1 µg/mL PHF dose-dependently induced cell loss, as measured using LDH and NeuN levels, as well as increased total and phosphorylated tau in the remaining neurons. It spread between cell populations, through release and subsequent uptake by other neurons. To test the efficacy of the molecules of the present invention, three different dosing methods (differing in the timing of tau and antibody administration) were utilized. For one of the antibodies, Antibody 4E6G7, two of these methods, addition of the PHF and antibody together, and addition of Antibody 4E6G7 24 h after PHF, prevented PHF toxicity, seeding, and spread. Interestingly, although similarly effective, the mechanism through which the protection occurs differed between the dosing paradigms.

When Antibody 4E6G7 or Antibody 6B2G12 were added 24 h after PHF, these co-localized intracellularly with PHF, but only Antibody 4E6G7 prevented PHF toxicity. Based on the confocal data from the co-incubation experiments, as well as dot blot and ELISA data, Antibody 4E6G7 was found to bind better to solubilized PHF than Antibody 6B2G12 (which reacts better with aggregated PHF and insoluble tau). This feature is considered to explain the intracellular efficacy of Antibody 4E6G7, i.e., that by binding to solubilized PHF, Antibody 4E6G7 acts to prevent PHF polymerization, thus facilitating access of lysosomal enzymes to clear PHF and/or directly neutralize soluble PHF, and preventing toxicity. However, Antibody 6B2G12-PHF binding may be inert without promoting disassembly. Furthermore, due to poor binding it may be unable to prevent PHF fibril formation and/or toxicity of soluble PHF.

The findings presented below thus explain the therapeutic efficacy of Antibody 4E6G7. It is capable of both extracellular blockage and intracellular clearance of PHF. Previous data indicate that Antibody 4E6G7 enters the endosomal/lysosomal system within tauopathy neurons and promotes clearance of native tau, possibly by preventing aggregation (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance*," J. Biol. Chem. 288:35452-35465; Gu, J. et al. (2013) "*Two Novel Tau Antibodies Targeting The 396/404 Region Are Primarily Taken Up By Neurons And Reduce Tau Protein Pathology*," J. Biol. Chem. 288(46):33081-33095; Krishnamurthy, P.vK. et al. et al. (2011) "*Mechanistic Studies of Antibody-Mediated Clearance of Tau Aggregates Using an ex vivo Brain Slice Model*," Front. Psychiatry 2:59). Other groups have observed internalization of tau antibodies (Collin, L., et al. (2014) "*Neuronal Uptake Of Tau/Ps422 Antibody And Reduced Progression Of Tau Pathology In A Mouse Model Of Alzheimer's Disease*," Brain 137(Pt 10):2834-2846; Kondo, A. et al. (2015) "*Antibody Against Early Driver Of Neurodegeneration Cis P-Tau Blocks Brain Injury And Tauopathy*," Nature 523(7561): 431-436), and lysosomal colocalization (Collin, L., et al. (2014) "*Neuronal Uptake Of Tau/Ps422 Antibody And Reduced Progression Of Tau Pathology In A Mouse Model Of Alzheimer's Disease*," Brain 137(Pt 10):2834-2846). Further, neuronal co-localization between antibody, target, and endosomal/lysosomal markers has been seen for α-synuclein antibodies in a PD mouse model (Masliah, E., et al. (2011) "*Passive Immunization Reduces Behavioral And Neuropathological Deficits In An Alpha-Synuclein Transgenic Model Of Lewy Body Disease*," PloS One 6(4): e19338). In other experiments, tau antibodies are able to block the uptake of pathological tau or improve experimental outcomes without apparently entering neurons (Castillo-Carranza, D. L., et al. (2014) "*Passive Immunization With Tau Oligomer Monoclonal Antibody Reverses Tauopathy Phenotypes Without Affecting Hyperphosphorylated Neurofibrillary Tangles*," J. Neurosci. 34(12):4260-4272; d'Abramo, C. et al. (2013) "*Tau Passive Immunotherapy In Mutant P301L Mice: Antibody Affinity Versus Specificity*," PLoS One 8(4):e62402; Yanamandra, K. et al. (2013) "*Anti-Tau Antibodies That Block Tau Aggregate Seeding in vitro Markedly Decrease Pathology And Improve Cognition in vivo*," Neuron 80(2):402-414). Whether antibodies are taken into neurons is likely influenced by several factors including, charge, target and Fc receptor affinity, and as data presented herein suggests, location of the target and timing of antibody addition.

In contrast, pre-incubation with Antibody 4E6G7 (i.e., in the absence of PHF) was ineffective at reducing toxicity or seeding of tau pathology that occurs once PHF is added. A likely reason is the relative lack of the target epitope under these conditions. Previously, it has been shown that neuronal Antibody 4E6G7 uptake correlates highly with pathological intracellular tau levels (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance,*" J. Biol. Chem. 288:35452-35465). When the antibody is added first, efficacy requires retention in neurons until PHF addition 24 h later. However, a shortage of the target means the antibody will remain unbound, and more prone to degradation or recycling out of the cell, as seen via confocal imaging. Although Antibody 4E6G7 was ineffective under these conditions, it does not rule out prophylactic administration of tau antibodies, as circulating antibodies could prevent disease initiation by clearing early-stage tau aggregates. Indeed, the findings of the present invention support the conclusion that such prophylactic administration of therapeutically effective tau antibodies (e.g., Antibody 4E6G7 or epitope-binding fragments thereof) to subjects at risk of tauopathy, but who do not have actual tauopathy, is not associated with adverse effects, and that such administration becomes effective upon the establishment of actual tauopathy. Exogenous antibodies have a half-life of one to three weeks and lower doses could be used in pre-symptomatic individuals at risk.

Notably, the different efficacies between dosing methods were also observed in the spreading assay using the microfluidic chambers. In both model systems, only the co-incubation dosing or PHF→Ab was effective, whereas Ab→PHF was not.

In previously published findings (Gu, J. et al. (2013) "*Two Novel Tau Antibodies Targeting The 396/404 Region Are Primarily Taken Up By Neurons And Reduce Tau Protein Pathology,*"J. Biol. Chem. 288(46):33081-33095), both Antibody 4E6G7 and Antibody 6B2G12 showed efficacy in preventing increased phospho-tau levels in a brain slice model, in contrast to Antibody 6B2G12's ineffectiveness in the primary neurons in the current study. There are likely multiple factors which contribute to these differences. In the slice culture system, treatment with antibodies lasted for up to six weeks and no exogenous tau was introduced in that system. In the results presented below, a much shorter time scale is used (seven days as opposed to six weeks) and the PHF tau that is utilized was isolated from a human AD brain. The tau found in the PHF fraction also represents a different stage of tangle formation. Furthermore, the PHF isolated from the AD brain may have additional posttranslational modifications not present in the endogenous tau of the slices. Differences in cell health over the course of the experiments are likely also influenced by the culture model. In the primary cultures, neurons lack the trophic support provided by glial cells, which are present in the brain slices.

Antibody uptake into neurons can be blocked with an antibody against FcII/III receptors or with dansyl cadaverine, which blocks receptor-mediated endocytosis (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance,*" J. Biol. Chem. 288:35452-35465). Under the co-incubation conditions, blocking antibody uptake had no effect on the outcome. However, when Antibody 4E6G7 was added 24 h after PHF addition, blocking its uptake prevented its beneficial effects. These findings confirm that under co-incubation conditions, the antibody is working extracellularly, but when it is added 24 h after PHF, its effects are intracellular.

Both Antibody 4E6G7 and Antibody 6B2G12 are taken up into tauopathy neurons in brain slice- and primary cultures, in which they co-localize with tau aggregates in the endosomal-lysosomal system (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance,*" J. Biol. Chem. 288:35452-35465; Gu, J. et al. (2013) "*Two Novel Tau Antibodies Targeting The 396/404 Region Are Primarily Taken Up By Neurons And Reduce Tau Protein Pathology,*" J. Biol. Chem. 288(46):33081-33095). Furthermore, Antibody 6B2G12 and its single chain variable fragment derivative can be used to image tau lesions in vivo and end up in the same neuronal compartments after peripheral injection (Krishnaswamy, S. et al. (2014) "*Antibody-Derived in vivo Imaging of Tau Pathology,*" J Neurosci. 34(50):16835-16850). Such uptake and co-localization is by itself not an indication of efficacy but we have shown that prevention of Antibody 4E6G7 neuronal uptake blocks acute antibody-mediated tau clearance (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance,*" J. Biol. Chem. 288:35452-35465). The culture data confirms such intracellular clearance and additionally shows prevention of neurotoxicity by Antibody 4E6G7 in a different culture model, which is more relevant to human disease as AD derived PHF material is used. Furthermore, in PHF-treated primary cultures, Antibody 6B2G12 was ineffective under various experimental conditions using multiple outcome measures. Overall, Antibody 4E6G7 is thus found to be better suited as a therapeutic antibody targeting soluble tau species and Antibody 6B2G12, or ideally its smaller derivatives with better access to the target, more useful as an imaging probe for insoluble tau lesions.

Specifically, the ex vivo culture model shows that Antibody 4E6G7, a monoclonal tau antibody targeting the phospho-serine 396/404 region prevented toxicity and reduced tau levels induced by the addition of Alzheimer's brain-derived PHF material. Importantly, another tau monoclonal, Antibody 6B2G12, which has substantially higher affinity for the tau peptide immunogen and aggregated PHF tau than Antibody 4E6G7, was ineffective under these experimental conditions. Further analyses revealed that Antibody 4E6G7 had higher affinity than Antibody 6B2G12 for the solubilized PHF that was used to promote toxicity in cultured neurons. This likely explains the efficacy of the former antibody and lack thereof for the latter. These findings have major implications for the development of passive tau immunotherapies. Efficacy cannot be predicted by affinity to the immunogen alone or to aggregated tau, but has to be determined in biological models of tau pathology. Combined with imaging data, these results provide information on how affinity and efficacy relate.

Other tau immunotherapy studies have reported efficacy differences between antibodies recognizing epitopes of different sequences of tau and one study between different isotypes of two antibodies of similar affinity against the same epitope (for review see Pedersen, J. T. et al. (2015) "Tau Immunotherapy for Alzheimer's Disease," Trends Mol. Med. 21(6):394-402). Antibody 4E6G7 and Antibody 6B2G12 are of the same isotype, IgG1, and the findings presented herein show for the first time that subtle difference in epitope recognition can profoundly affect efficacy. Importantly, such findings confirm and provide mechanistic insight into these in vivo differences in a disease relevant ex vivo neuronal culture model, in which tau pathology is promoted with Alzheimer's brain-derived PHF in primary neurons expressing familial tau mutation. Hence, the contrasting efficacies are seen consistently in different models with or without tau mutation and may have major therapeutic implications for both familial and sporadic tauopathies. The models employed have strong construct and face validity as they are based on sound theoretical rational as normal or familial (mutated) human tau is being expressed, and have the key features associated with tauopathies, namely tau aggregation, toxicity, and associated cognitive impairments in the animals. The human PHF culture model has strong predictive validity for the outcome in the animal model.

EXAMPLES

The following examples illustrate various methods for compositions in the diagnostic or treatment methods of the invention. The examples are intended to illustrate, but in no way limit, the scope of the invention.

Example 1

Materials and Methods

Materials—Pan-Tau rabbit polyclonal antibody corresponding to residues 243-441 was purchased from Dako (Carpinteria, Calif.). Polyclonal rabbit antibody specific for $^{\{P\}}$Ser199 Tau was purchased from Santa Cruz Biotechnology (Dallas, Tex.).

Mice—Mouse pups from the JNPL3 mouse line were collected at postnatal day zero for primary cultures. These animals express the ON4R human Tau isoform containing the naturally occurring P301L mutation, in addition to native mouse Tau (Lewis, J., et al. (2000) "*Neurofibrillary Tangles, Amyotrophy And Progressive Motor Disturbance In Mice Expressing Mutant (P301L) Tau Protein*," Nature Genetics 25(4):402-405). For experiments examining the spread of Tau between cell populations, wild-type ("WT") pups from the same strain background as the transgenic animals were also utilized.

Isolation of Paired Helical Filament (PHF) Material—PHF-Tau was extracted from the brain of a human AD patient. Tissue was homogenized in buffer (1 mL/g of tissue) containing 0.75 M NaCl, 1 mM EGTA, 0.5 mM MgSO$_4$, 100 mM 2-(N-morpholino) ethanesulfonic acid, and Roche protease inhibitor cocktail. Samples were then centrifuged at 11,000 g for 20 min at 4° C. and the pellet discarded. The remaining supernatant was further centrifuged at 100,000 g for 60 min at 4° C. The pellet was resuspended in PHF extraction buffer (10 mM Tris, 10% sucrose, 0.85 M NaCl, and 1 mM EGTA, pH 7.4) and centrifuged at 15,000 g for 20 min at 4° C. This same resuspension and centrifugation was repeated, and the final pellet was dissolved in 50 mM Tris-HCl (pH 7.4) and dialyzed in phosphate-buffered saline (PBS) for 6 hours.

Fluorescent Labeling—Antibody 4E6G7 and human-derived PHF material were labeled using Alexa Fluor 488 and 647 labeling kits, respectively. The antibody or PHF was incubated with reactive dye with stirring for 1 h at room temperature. As per instructions, the elution column was prepared and the dye/substrate mixture was added. Material was collected and labeling verified.

Primary Neuronal Cultures—Primary neuronal cultures were prepared as described in Congdon, E. E. et al. (2013) "*Antibody Uptake Into Neurons Occurs Primarily Via Clathrin Dependent Fcgamma Receptor Endocytosis And Is A Prerequisite For Acute Tau Protein Clearance*," J. Biol. Chem. 288(49):35452-35465. Briefly, plates were coated with poly-L-lysine for 3 h prior to the addition of cells. Brains were harvested from mouse pups at postnatal day zero, and the brainstem discarded. Meninges were removed from the cortex and hippocampus. Tissue was roughly chopped and washed five times in HBSS+++ (Hank's Balanced Salt Solution, 10 mL 1M HEPES, 5 mL penicillin/streptomycin, 10 mL 100 mM sodium pyruvate). After washing, tissue was incubated for 20 min with 200 µl of 0.5% trypsin. Trypsin was neutralized with 5 mL of plating media (Minimum Eagle's medium, 15 mL GlutaMAX, 50 mL FBS, 4 mL B27 supplement, 2.5 mL penicillin/streptomycin), and washed a further three times in HBSS+++. Following this, cells were manually dissociated and centrifuged for 1 min at 0.5×g. Cells were then resuspended in plating media and evenly distributed among the wells. After 24 h in culture, plating media was removed and Neuronal media (Neurobasal A, 1 mL B27, 17 µL basal medium Eagle) was added. The same procedure was utilized for cultures grown in microfluidic chambers. Cells from the JNPL3 mice were plated on one side of the axon isolation device. Cells were allowed to incubate for 72 h. Following this period, brains from WT animals were harvested and cells plated on the opposite side.

LDH Assays—Media was collected from all treatment groups after seven days in culture. LDH (lactate dehydrogenase) levels in the media were determined using a Roche cytotoxicity detection kit. Values obtained from treated samples were compared to values obtained from media collected on day zero in order to ascertain the extent of toxicity. Media from a set of untreated cells was also collected to examine the normal changes in cell health over the culture period. Treated samples, controls and blanks were added to a 96 well plate and the detection reagents were added as per the instructions. Plates were incubated for 20 minutes at 37° C. and read using a BioTek Synergy 2 plate reader.

Microfluidic Chambers And Tau Spreading—Cells were harvested and plated as described above. Following the addition of the WT cells, cultures were given one week in culture to stabilize. The same three treatment methods were utilized. PHF and Antibody 4E6G7 (1 µg/mL each) were added to the chamber containing JNPL3 cells, while the opposing chamber containing WT cells was left untreated. As a negative control, one group of cells was incubated with 1 µg/mL of the PHF material and 50 nM of botulinum toxin. The toxin was chosen due to its ability to prevent membrane fusion and the release of membrane bound vesicles, and thus prevent release of PHF-Tau into the opposite chamber. In neuronal cultures, botulinum toxin has also been shown to prevent the spread of mutant huntingtin by blocking synaptic vesicle release (Pecho-Vrieseling, E., et al. (2014) "*Transneuronal Propagation Of Mutant Huntingtin Contributes To Non-Cell Autonomous Pathology In Neurons*," Nat. Neurosci. 17(8):1064-1072). In all groups, after the final treatment, cells were maintained in culture for a further 72 h. Coverslips were then fixed and the specimens wee stained for antibodies recognizing total Tau. The percentage of cells in the contralateral chamber containing labeled PHF material was determined for each treatment group.

Immunohistochemistry—Media was removed and the cells washed three times in PBS. Coverslips were fixed in 4% formaldehyde containing 0.5% sucrose for 20 min at 37° C. Cells were permeabilized and blocked using PBS containing 3% Pecho-Vrieseling, E., et al., Transneuronal propagation of mutant huntingtin contributes to non-cell autonomous pathology in neurons. Nat Neurosci, 2014. 17(8): p. 1064-72. BSA and 0.1% saponin for 20 minutes at room temperature. Primary antibodies were utilized at a 1:200 dilution for 1 hour, following which cells were washed three times with PBS for five minutes per wash. Secondary antibody was applied at a 1:400 dilution for 30 min, and cells were washed a further three times before coverslips were mounted using Dako Fluorescent mounting medium. Images were collected using a Nikon Eclipse Ti confocal microscope, and processed using Image J.

Immunoblotting—Cells were washed three times in PBS and then lysed in modified RIPA buffer (50 mM Tris-HCl, pH 7.4, 150 mM NaCl, 1 mM EDTA, 1 mM NaF, 1 mM $Na_3VO_4$, 1 µg/mL complete protease inhibitor mixture (Roche Applied Science)). Samples were briefly sonicated, and volume adjusted for total protein concentration. Loading buffer (62.5 mM Tris-HCl pH 6.8, 5% glycerol, 2-mercapoethanol, 2.3% SDS, 1 mM EDTA, 1 mM phenylmethylsulfonyl fluoride, 1 mM $Na_3VO_4$, 1 µg/mL Roche Applied Science complete protease inhibitor) was added and samples were boiled for 5 minutes. All samples were loaded onto a 12% polyacrylamide gel, then transferred at 100 V for 1 hour. Membranes were blocked Tris-Buffered Saline and Tween 20 (TBST) containing 5% non-fat milk for 30 minutes, following which they were incubated in primary antibody overnight at 4° C. Blots were washed and incubated with peroxidase-labeled secondary antibody for 1 hour. Bands were visualized using a Fuji LAS-4000 and chemiluminescent signal was quantified using Multigauge.

Example 2

Isolation of scFv Fragments of Antibody 4E6G7 scFv molecules may be generated from hybridoma clone Antibody 4E6G7 (raised against the preferred immunogen having the amino acid sequence of SEQ ID NO:8: TDH-GAEIVYK${^{\{P\}}}$_ PVVSGDT${^{\{P\}}}$_PRHL) (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance*," J. Biol. Chem. 288:35452-35465; Gu, J. et al. (2013) "*Two Novel Tau Antibodies Targeting The 396/404 Region Are Primarily Taken Up By Neurons And Reduce Tau Protein Pathology*," J. Biol. Chem. 288(46):33081-33095). Briefly, the hybridoma cell line Antibody 4E6G7 may be grown at 37° C. with 5% $CO_2$ in RPMI medium containing streptomycin (50 µg/mL) and Penicillin G (50 U/mL), and its mRNA isolated and purified as per the protocol of an RNA isolation kit (Promega), and subsequently stored at −80° C. The first strand cDNA may be constructed as per the protocol of a first strand cDNA synthesis kit (Takara kit (TAK6115A)).

Clones may then be screened for their ability to express scFv molecules that are immunospecific for the ${^{\{P\}}}$Ser404 Epitope using peptides (Keck Foundation, Yale University) having the sequences of Tau 379-408 (${^{\{P\}}}$Ser396/${^{\{P\}}}$Ser404) (SEQ ID NO:30):

RENAKAKTDH GAEIVYK${^{\{P\}}}$SPV VSGDT${^{\{P\}}}$SPRHL and Tau 379-408 (Ser396/Ser404) (SEQ ID NO:31):

RENAKAKTDH GAEIVYK<u>S</u>PV VSGDT<u>S</u>PRHL

These peptides may also be used for panning, ELISA and in BIACORE™ for binding studies.

Example 3

Antibody 4E6G7: Tau Antibody-Mediated Prevention of Seeding of Tau Pathology and Associated Toxicity Tau pathology spreads between neurons in culture and in vivo and can be targeted with antibodies both intracellularly and extracellularly. The ability of Antibody 4E6G7, which immunospecifically binds to the ${^{\{P\}}}$Ser404 Epitope, to prevent toxicity and the spread of Tau pathology mediated by paired helical filament (PHF) preparation from an Alzheimer's subject was assessed. For this purpose, primary JNPL3 (P301L) neuronal cultures were prepared as described and allowed to recover in culture for one week prior to treatment. Cells were incubated with either 1 or 10 µg/mL of the human-derived PHF material, with cells and culture incubated with either 1 or 10 µg/mL of the human-derived PHF material, with cells and culture media collected at 1, 2, 3, 5 and 7 days. Control cultures were treated for seven days with PHF alone (1 or 10 µg/mL) ("PHF Alone" treated cells). For cultures being treated with a combination of PHF (1 or 10 µg/mL) and Antibody 4E6G7 (10 µg/mL), three different treatment strategies were used. In the first, PHF material was added and allowed to incubate with the cultures for 24 h. Following this period, the cells were washed with Neuronal media, and fresh media containing 1 µg/mL of Antibody 4E6G7 was added ("PHF→Antibody" treated cells). In the second, PHF material and Antibody 4E6G7 were added to the culture media simultaneously ("PHF+Antibody" treated cells). The third dosing strategy is the inverse of the first, Antibody 4E6G7 was added 24 h prior to PHF ("Antibody→PHF" treated cells). As a control, non-specific mouse IgG was used in place of Tau antibody. In experiments using dansylcadaverine (DC), the same methods were employed with 1 µg/mL DC added along with the antibody.

FIG. 1, Panels A-B show the effect of Antibody 4E6G7 (Panel A) and IgG1 Control (Panel B) on cellular toxicity mediated by 10 µg/mL PHF as determined by LDH release. As shown in FIG. 1, Panel A, in cells treated with 10 µg/mL PHF, LDH signal averaged 67% above that of untreated controls (p=0.001). Antibody 4E6G7 (1 µg/mL) in the PHF+Antibody and PHF→Antibody paradigms significantly reduced LDH compared to PHF alone (11% above control p=0.02, and 15% above control p=0.03), and were comparable to untreated samples, indicating that the antibody can prevent toxicity. However, the Antibody→PHF was not effective in reducing LDH signal (53% above control, p=0.009) and showed no significant improvement over PHF alone samples at the 1 µg/mL concentration tested. As shown in FIG. 1, Panel B, IgG1 was also not effective in preventing the increased LDH levels triggered by the addition of PHF. LDH in the PHF+Antibody, PHF→Antibody, and Antibody→PHF groups was increased to 80, 43 and 61% above control values (p=0.004, 0.03, and 0.01, respectively). None of the groups was significantly different from PHF alone. (*p=0.05).

Figure 2:
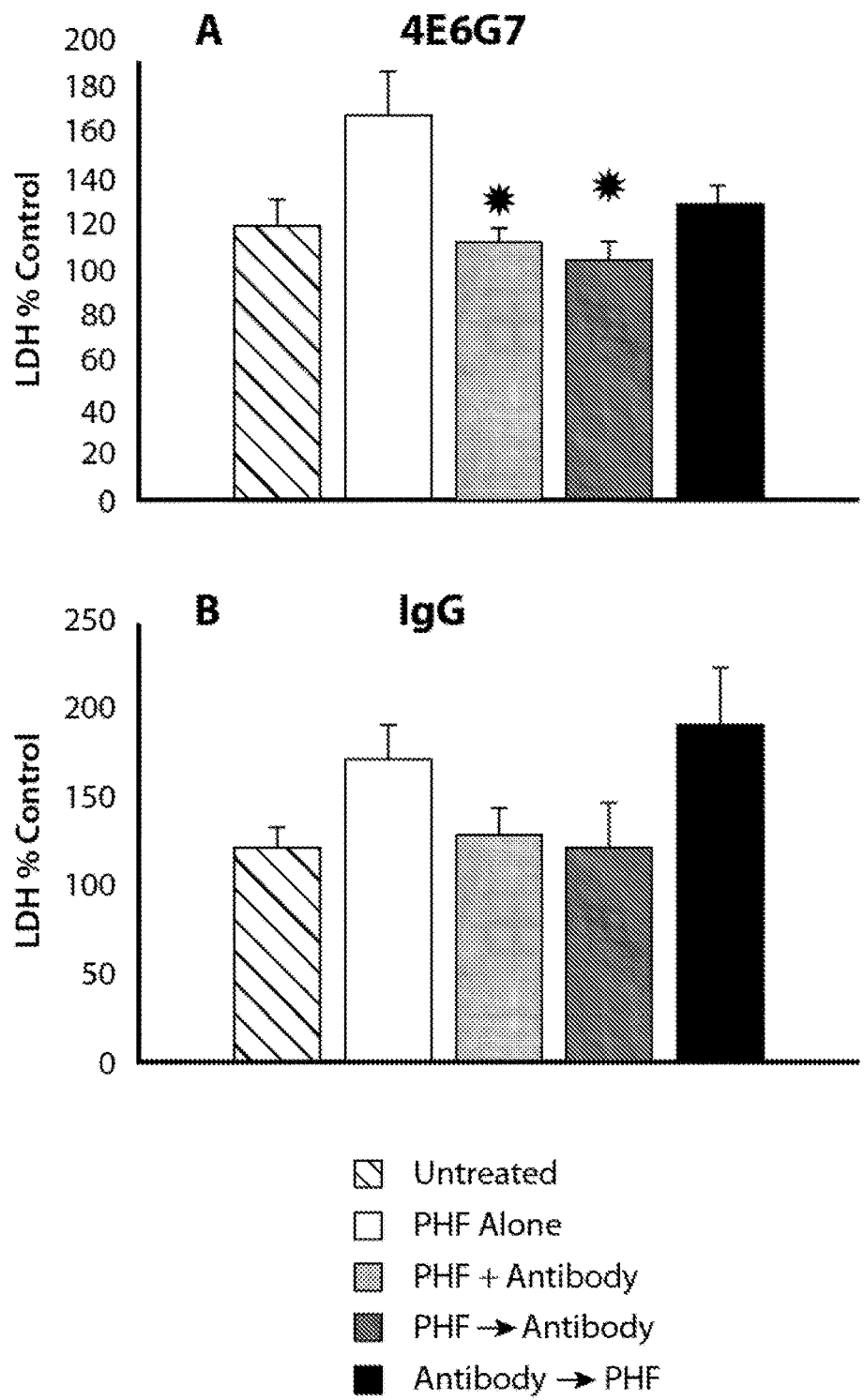
FIG. 2, Panels A-B show the effect of Antibody 4E6G7 (Panel A; *p=0.05) and IgG Control (Panel B) on cellular toxicity mediated by 1 μg/mL PHF as determined by LDH release.

FIG. 2, Panels A-B show the effect of Antibody 4E6G7 (Panel A) and IgG1 Control (Panel B) on cellular toxicity mediated by 1 μg/mL PHF as determined by LDH release. As shown in FIG. 2, Panel A, incubation with 1 μg/mL PHF increased LDH signal by 35% relative to untreated control cells (p=0.04). Tau monoclonal Antibody 4E6G7 in the PHF+Antibody or PHF→Antibody conditions significantly reduced LDH compared to PHF alone samples (p=0.04 and 0.03, respectively) and did not significantly differ from untreated cells. The Antibody→PHF group did not show reduced LDH compared to neurons that received only PHF (11% above control). As shown in FIG. 2, Panel B, at the 1 μg/mL PHF dose, samples treated with IgG1 did not show significantly higher LDH levels than control cells, indicating that it may offer some non-specific protection (PHF+Antibody, PHF→Antibody, and Antibody→PHF groups were 6% above control, equal to control, and 67% above control respectively). However, the IgG1 samples were also not significantly different from the PHF alone samples. (*p=0.05) again confirming the specificity of Antibody 4E6G7 effect to prevent PHF toxicity.

Toxicity was additionally examined via immunoblotting with an antibody recognizing neuronal marker NeuN. NeuN is a neuron-specific nuclear protein observed in most neuronal cell types throughout the nervous system of adult mice (Mullen, R. J. et al. (1992) "*NeuN, A Neuronal Specific Nuclear Protein In Vertebrates*," Development 116(1):201-211). The protein serves as a neuronal marker in the differential diagnosis of clear cell neoplasms of the central nervous system (Soylemezoglu, F. et al. (2003) "*Neuronal Nuclear Antigen (NeuN): A New Tool In The Diagnosis Of Central Neurocytoma*," Pathol. Res. Pract. 199(7):463-468).

Figure 3:
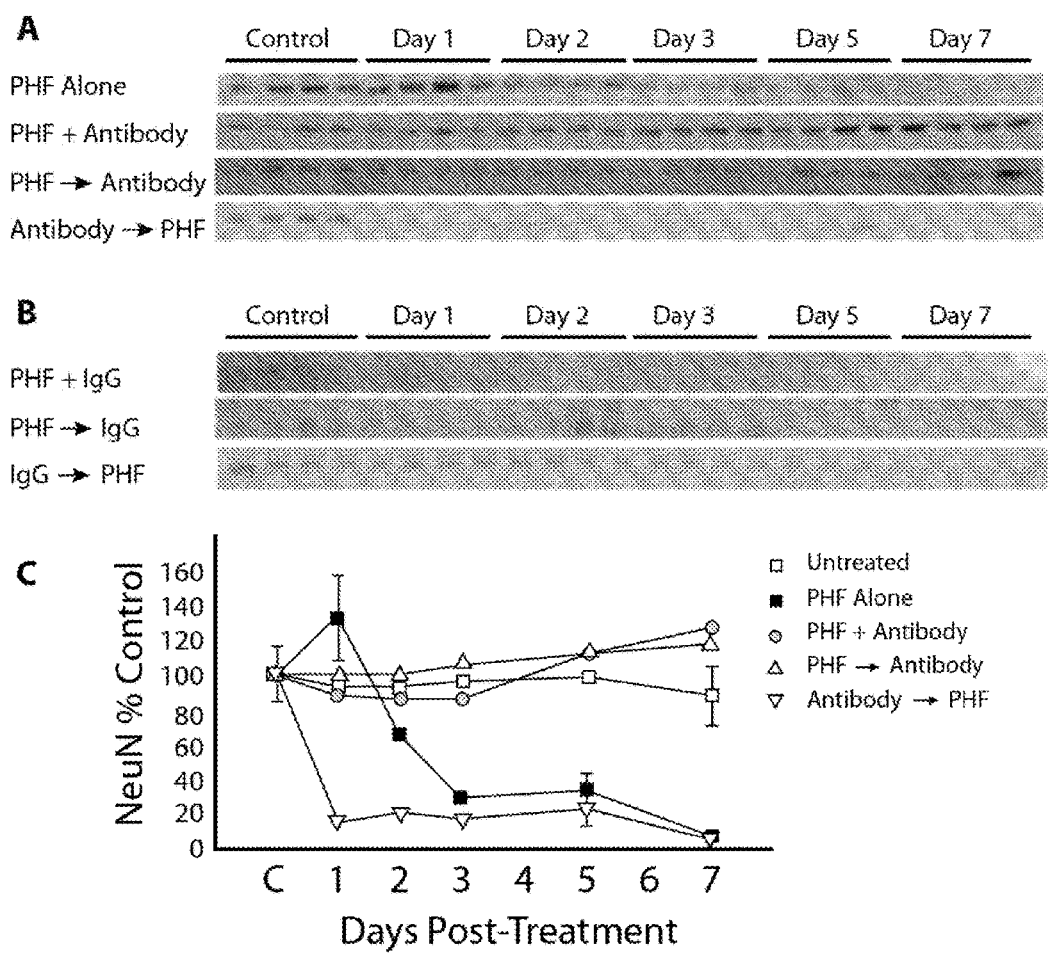
FIG. 3, Panels A-C show immunoblots showing the ability of Antibody 4E6G7 (Panel A; 10 μg/mL) to prevent loss of NeuN signal relative to cells treated with 10 μg/mL PHF and 1 μg/mL non-specific mouse IgG (Panel B). Panel C shows the quantitation of signal in samples treated with PHF alone or a combination of PHF and Antibody 4E6G7.

When incubated in the presence of 10 μg/mL PHF, the NeuN signal steadily declined and was reduced 94% relative to untreated control samples by day 7 (FIG. 3, Panels A-B). As was the case with the LDH samples, the PHF+Antibody and PHF→Antibody paradigms resulted in NeuN levels that were significantly higher than those of samples incubated with PHF alone (samples were 16% and 24% above untreated control on day 7, p=0.000003 and 0.00002). Also as above, the Antibody→PHF dosing method was not effective in preventing the loss of NeuN over the treatment period (93% loss, p=0.0008 relative to control) and showed no improvement over the PHF alone samples (FIG. 3, Panel C). As in the LDH assay, the IgG1 had no effect on PHF-induced toxicity.

Figure 4:
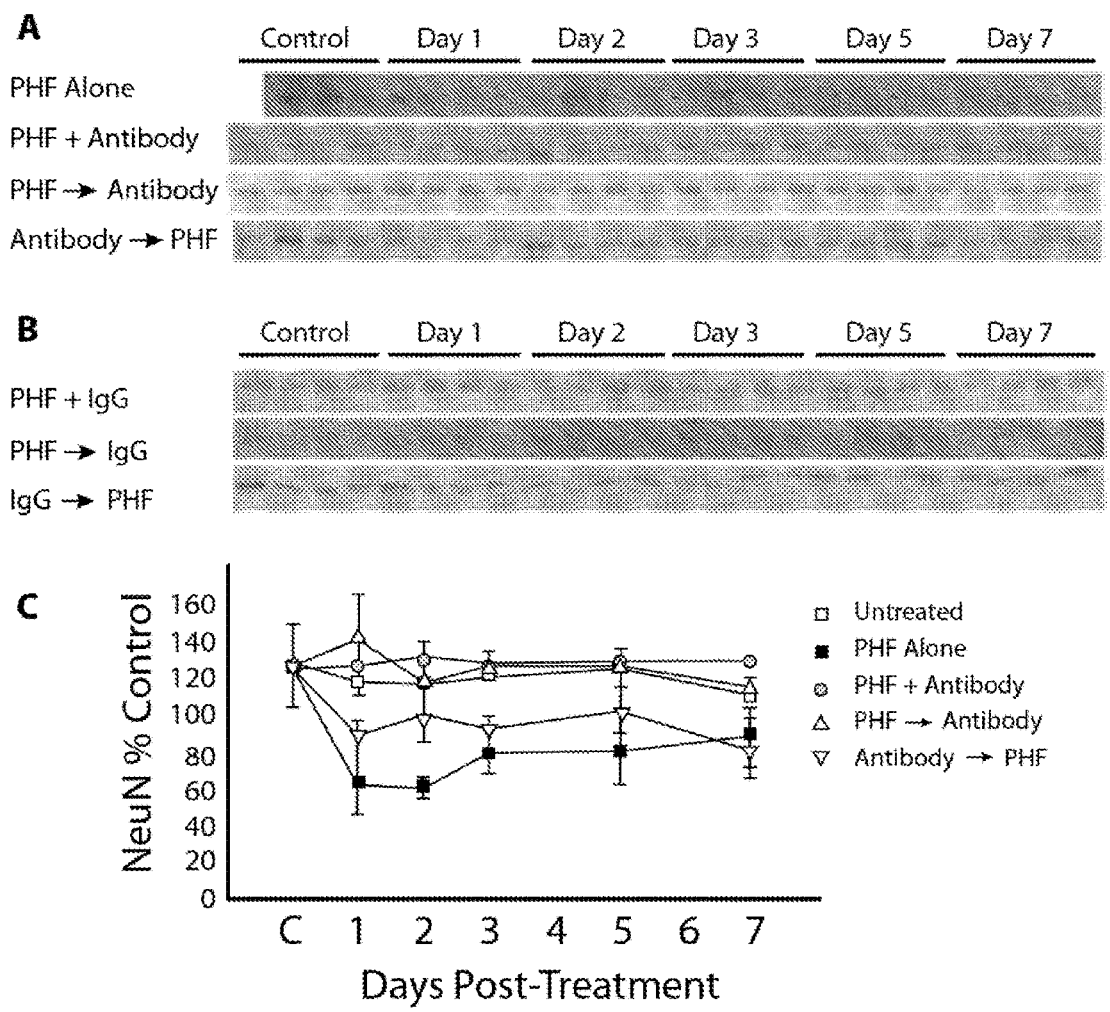
FIG. 4, Panels A-C show that PHF induces a loss of NeuN at 1 μg/mL, and that this effect can be prevented with Antibody 4E6G7. Immunoblots are shown for samples treated with 1 μg/mL PHF alone or 1 μg/mL PHF and either 1 μg/mL Antibody 4E6G7 (Panel A) or 1 μg/mL of control IgG (Panel B). Panel C shows the quantitation of signal in samples treated with PHF alone or a combination of PHF and Antibody 4E6G7.

Additional groups of neurons were incubated with 1 μg/mL PHF and 1 μg/mL of Antibody 4E6G7 or control IgG (FIG. 4, Panels A-B). A 30% loss of NeuN signal relative to untreated control cells was observed in the PHF alone group (p=0.03) after seven days in culture (Panel C). As in the 10 μg/mL experiments, the PHF+Antibody and PHF→Antibody groups showed efficacy in preventing the loss of NeuN, and at day 7 were comparable to untreated controls and significantly higher that PHF alone samples (p=0.03). The Antibody→PHF group also showed a decline in NeuN levels (36% decrease relative to untreated control) comparable to that of neurons incubated with PHF alone samples, confirming the inefficacy of this approach at the dosage employed. As in the higher PHF dose samples, control mouse IgG1 was ineffective in preventing toxicity under any of the dosing conditions and did not differ significantly from the results seen with PHF alone.

These data show that Tau antibodies can be effective at mediating the toxicity triggered by exposure to misfolded Tau aggregates. Antibody 4E6G7 prevented toxicity, and then only under certain conditions. When Antibody 4E6G7 is added prior to PHF, it is possible that the relatively low level of Tau native to the neurons does not provide sufficient targets to promote the retention of antibody necessary to fully protect the cells.

Example 4

Antibody 4E6G7: Tau Antibody-Mediated Prevention of Changes in Tau Levels

Figure 5:
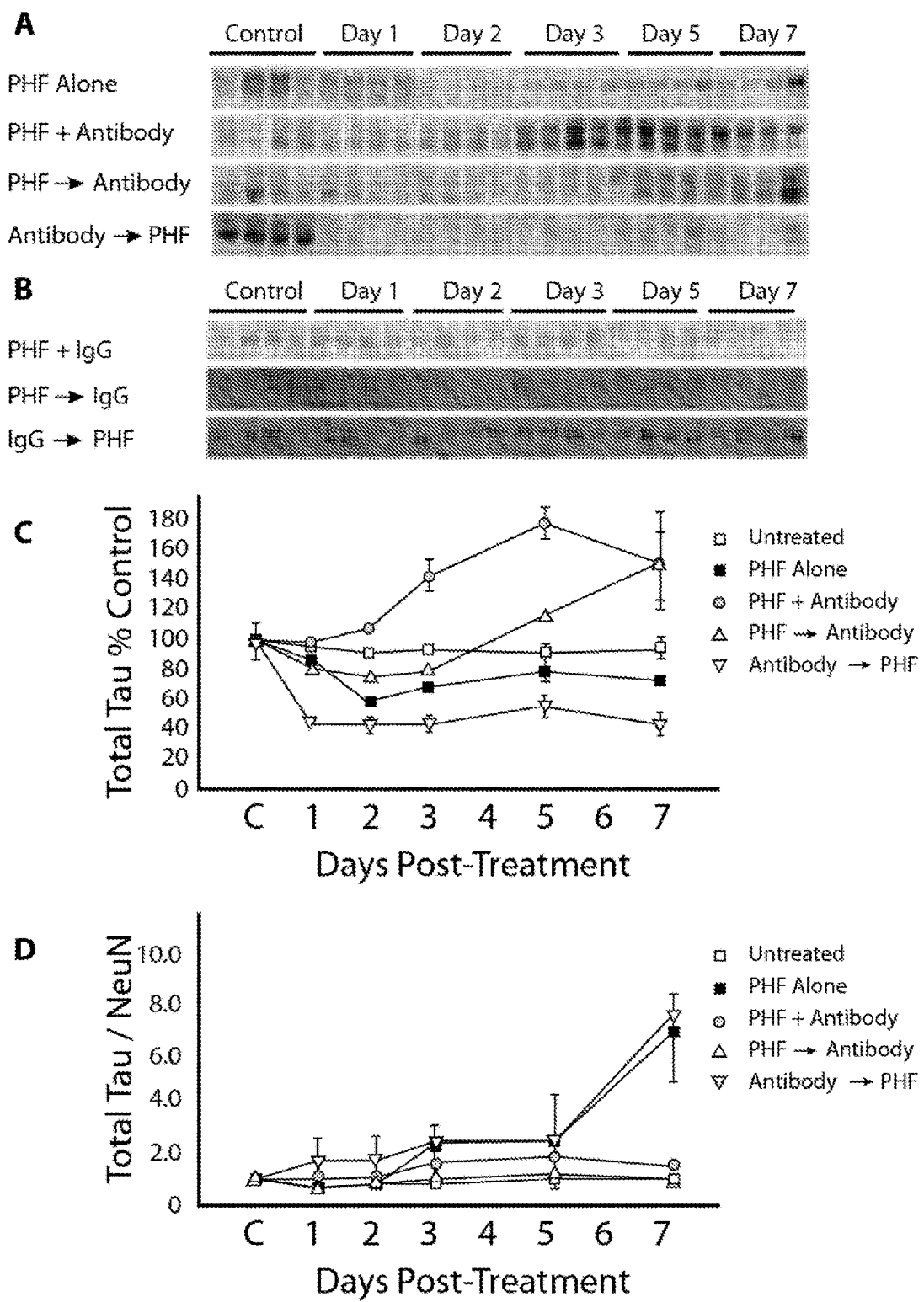
FIG. 5, Panels A-D show that Antibody 4E6G7 can prevent increases in intracellular Tau caused by exposure to 10 μg/mL PHF material. Panel A shows immunoblots of samples incubated with PHF or PHF in combination with Antibody 4E6G7, probed with a pan-Tau antibody. Panel B shows immunoblots of samples from cells incubated with a control mouse IgG and PHF. Panel C shows the quantitation of total Tau levels in samples incubated with PHF and Antibody 4E6G7. Panel D shows the results normalized for NeuN levels.

In addition to measures of toxicity, the effect of PHF and antibody treatments on Tau levels were also investigated. At the 10 μg/mL concentration, the total Tau levels in the PHF alone group showed an initial decrease followed by a recovery (FIG. 5, Panels A-D). However, by day 7, total Tau levels were significantly reduced relative to control cells (a 29% decrease, p=0.002) (Panel C). However, the Antibody 4E6G7 PHF+Antibody and PHF→Antibody groups have significantly higher Tau levels (48% and 51% above control) than cells incubated with PHF alone (Panel C). Again the Antibody→PHF group and IgG1 groups were ineffective in preventing changes in Tau levels compared to PHF alone cells.

When these results are normalized for NeuN levels, the remaining cells in the PHF group are observed to have significantly more Tau that control cells (5.6-fold increase, p=0.0005 and 0.04) (FIG. 5, Panel D). In the PHF+Antibody and PHF→Antibody groups, adjusted Tau levels are comparable to control and significantly lower than for cells that had received PHF alone (p=0.01 and 0.001 respectively). Results for the control IgG1 treated cells did not differ significantly from those of cells that had received PHF alone. Controlling for NeuN did not alter the pattern of results for such control cells.

Figure 6:
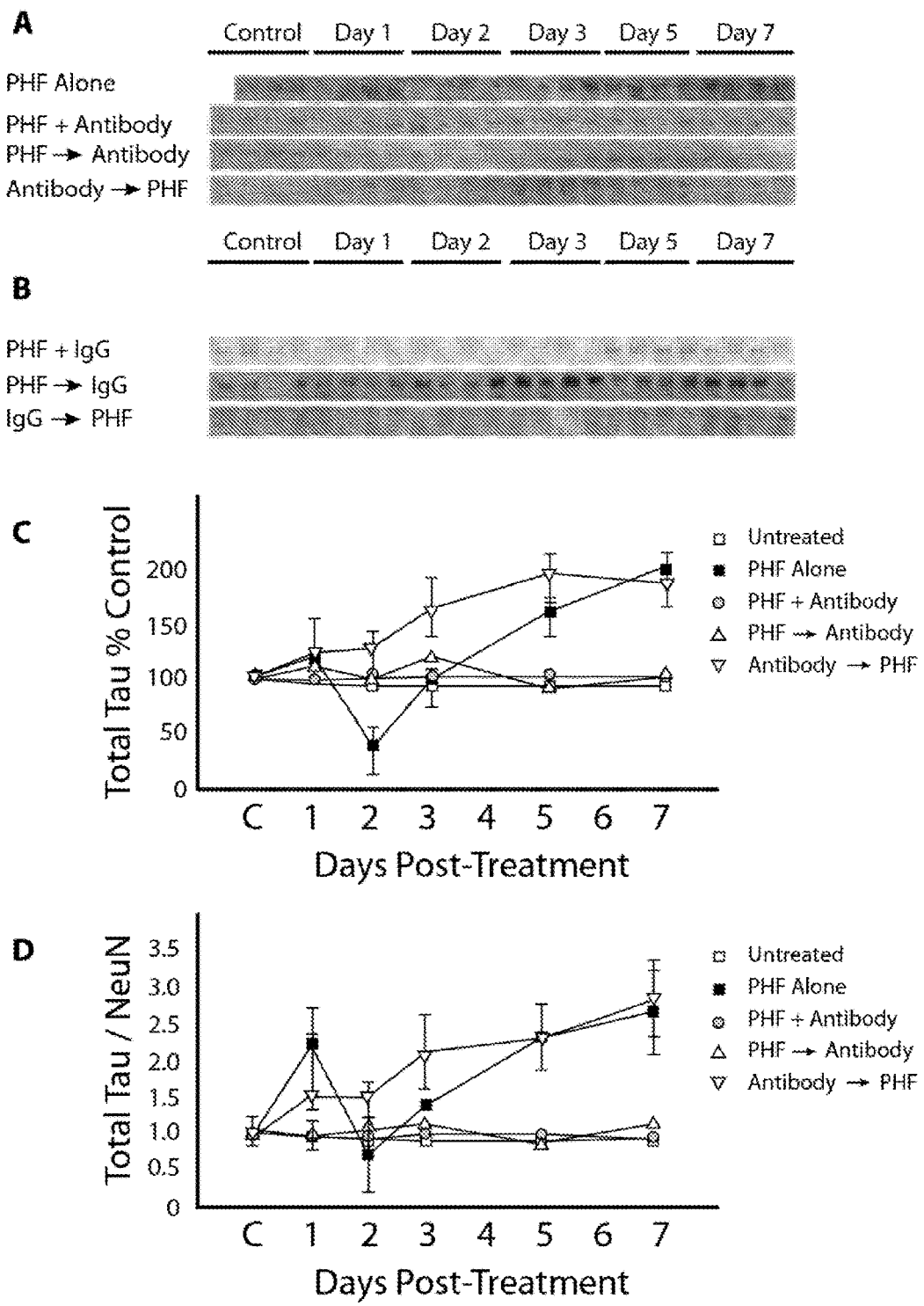
FIG. 6, Panels A-D shows that PHF at 1 mg/mL can promote increases in intracellular Tau, and that Antibody 4E6G7 can prevent these effects. Panel A and Panel B: Immunoblots for samples exposed to PHF, PHF+Antibody or PHF+IgG control, probed with a pan-Tau polyclonal antibody. Panel C: Quantitation of total Tau levels. Panel D: Intracellular Tau production normalized to NeuN.

At the 1 μg/mL dose, the increased Tau levels were evident even before normalization with NeuN levels (FIG. 6, Panels A-D). FIG. 6, Panels A-D show that PHF at 1 mg/mL can promote increases in intracellular Tau, and Antibody 4E6G7 can prevent these effects. Panels A-B show immunoblots for samples exposed to PHF alone, PHF+Antibody, PHF→Antibody and Antibody→PHF for Antibody 4E6G7 (Panel A) or control IgG (Panel B), probed with a pan-Tau polyclonal antibody. Panel C shows a quantitation of total Tau levels. At 1 μg/mL, PHF promotes significant increases in intracellular Tau (95% above control, p=0.001). For Antibody 4E6G7, the PHF+Antibody and PHF→Antibody were significantly lower than the PHF alone samples (p=0.001 for both). Cells treated with Antibody→PHF were not reduced relative to cells that had been treated with PHF alone. Adjusting for NeuN levels, again the PHF alone treatment significantly increased intracellular Tau relative to control cells (1.6-fold increase, p=0.02). For Antibody 4E6G7, the PHF+Antibody and PHF→Antibody treated cells, but not Antibody→PHF treated cells, exhibited significantly lower corrected Tau levels compared to the PHF alone groups (p=0.03 for both) and did not differ from untreated controls (Panel D). IgG1 does not prevent against significant increases in total Tau after exposure to PHF with or without controlling for NeuN levels.

In addition to total Tau levels, the levels of Tau phosphorylated at $^{\{P\}}$Ser199 was investigated. The phosphorylation of Tau at serine 199 ($^{\{P\}}$Ser199) appears to be involved in Alzheimer's disease and other neurological conditions (Biernat, J. et al. (1992) "*The Switch Of Tau Protein To An Alzheimer-Like State Includes The Phosphorylation Of Two Serine-Proline Motifs Upstream Of The Microtubule Binding Region*," EMBO J. 11(4):1593-1597; Takamatsu, J. (1998) "*Selective Expression Of Ser* 199/202 *Phosphory-* lated Tau In A Case Of Frontotemporal Dementia," Dement. Geriatr. Cogn. Disord. 9(2):82-89; Itoh, N. et al. (2001) "Large-Scale, Multicenter Study Of Cerebrospinal Fluid Tau Protein Phosphorylated At Serine 199 For The Antemortem Diagnosis Of Alzheimer's Disease," Ann. Neurol. 50(2): 150-156; Maurage, C. A. et al. (2003) "Phosphorylated Serine 199 Of Microtubule Associated Protein Tau Is A Neuronal Epitope Abundantly Expressed In Youth And An Early Marker Of Tau Pathology," Acta Neuropathol. 105 (2):89-97; Hampel, H. et al. (2004) "Measurement Of Phosphorylated Tau Epitopes In The Differential Diagnosis Of Alzheimer Disease: A Comparative Cerebrospinal Fluid Study," Arch. Gen. Psychiatry 61(1):95-102; Morioka, M. et al. (2006) "Hyperphosphorylation At Serine 199/202 Of Tau Factor In The Gerbil Hippocampus After Transient Forebrain Ischemia," Biochem. Biophys. Res. Commun. 347(1): 273-278; Loeffler, D. A. et al. (2015) "Effects Of Antibodies To Phosphorylated And Non-Phosphorylated Tau On In Vitro Tau Phosphorylation At Serine-199: Preliminary Report," Exp. Gerontol. 67:15-18). Thus, antibodies (such as Antibody AT8) that bind to $^{\{P\}}$Ser199 can be used to assess the presence of Alzheimer's disease.

Figure 7:
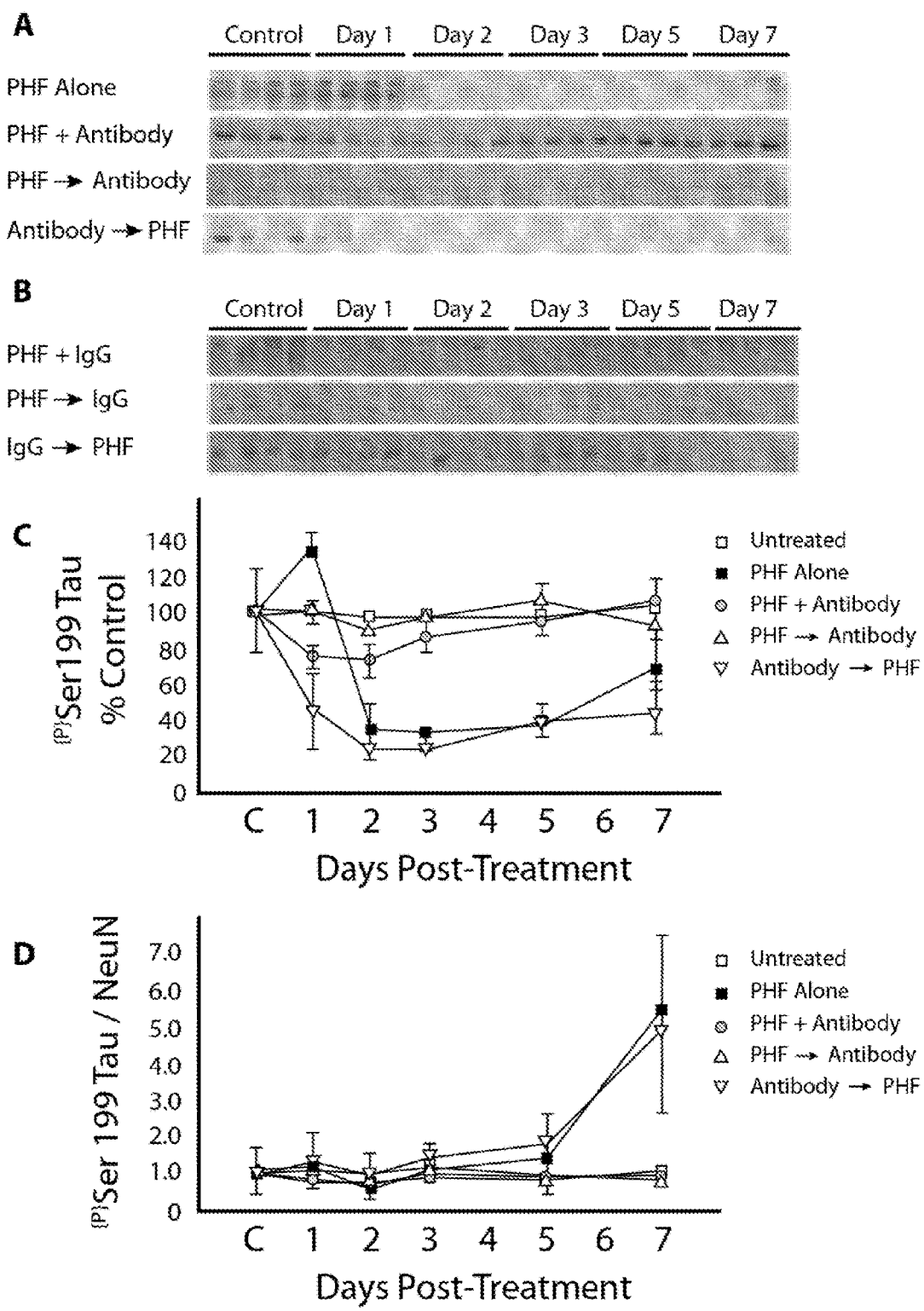
FIG. 7, Panels A-D show the ability of Antibody 4E6G7 to prevent the increase in phosphorylated Tau triggered by exposure to PHF at 10 μg/mL. Panels A-B show immunoblots of cells exposed to PHF alone or to PHF in combination with Antibody 4E6G7 (Panel A) or control IgG (Panel B), probed with a polyclonal antibody recognizing ${p}$Ser199 phospho-Tau. Panel C quantitates ${p}$Ser199 phospho-Tau levels relative to untreated cells. Panel D normalizes the results to NeuN levels.

Under the 10 μg/mL PHF conditions, PHF alone treated samples and Antibody→PHF treated samples had significantly reduced phospho-Tau levels relative to untreated cells (34%, 7%, and 54% reduction, p=0.00004, 0.01 and 0.01, FIG. 7). However, both the PHF+Antibody and PHF→Antibody treatment groups had significantly higher phospho-Tau levels than the PHF alone group (p=0.00001 and 0.00007). None of the IgG1 dosing groups differed significantly to PHF alone.

Correcting for NeuN levels, PHF alone samples showed higher levels of $^{\{P\}}$Ser199 Tau (a 4.1-fold increase, p=0.00004). Phospho-Tau levels in the PHF+Antibody and PHF→Antibody treated cells were significantly lower than those of cells that had been treated with PHF alone (p=0.000001 and 0.000007), and comparable to untreated controls. As with the uncorrected values, the results from cells that were additionally treated with control IgG1 did not differ from those of cells that had received PHF alone, nor did the Antibody→PHF treated group.

Figure 8:
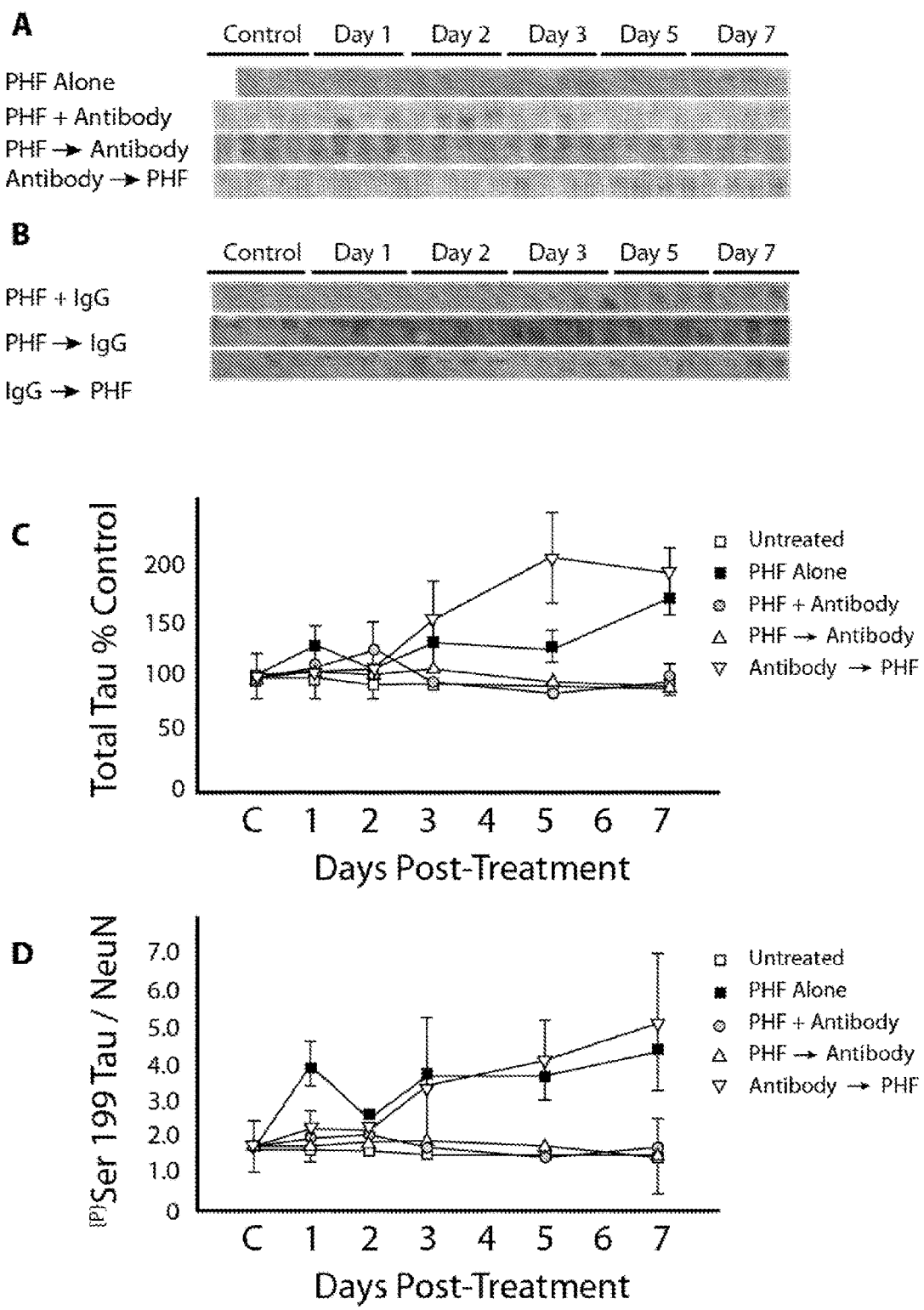
FIG. 8 (Panels A-D) show that lower levels of PHF (1 μg/mL) can also induce increase in phosphorylated Tau levels, and that such increases can be prevented by Antibody 4E6G7. Panels A-B show immunoblots of cells exposed to PHF alone or to PHF in combination with Antibody 4E6G7 (Panel A) or control IgG (Panel B), probed with a polyclonal antibody recognizing ${p}$Ser199 phospho-Tau. Panel C quantitates ${p}$Ser199 phospho-Tau levels relative to untreated cells. Panel D normalizes the results to NeuN levels.

Cells that had been incubated with PHF alone under the 1 μg/mL dosing conditions had significantly higher phospho-Tau levels than untreated control cells (65% above control, p=0.001, FIG. 8, Panels A-D). FIG. 8, Panels A-D show that lower levels of PHF (1 μg/mL) can also induce increase in phosphorylated Tau levels, and that such increases can be prevented by Antibody 4E6G7. Panels A-B show immunoblots of cells exposed to PHF alone or to PHF in combination with Antibody 4E6G7 (Panel A) or control IgG1 (Panel B), probed with a polyclonal antibody recognizing $^{\{P\}}$Ser199 phospho-Tau. Panel C quantitates $^{\{P\}}$Ser199 phospho-Tau levels relative to untreated cells. Panel D normalizes the results to NeuN levels.

In cells treated with 1 μg/mL PHF and Antibody 4E6G7, the antibody was effective in preventing PHF-induced pathological changes when under the PHF+Antibody and PHF→Antibody dosing conditions. Both groups had significantly lower phospho-Tau levels than PHF alone (p=0.01 and 0.006) at levels comparable to untreated controls. However, under the Antibody→PHF dosing condition, Antibody 4E6G7 was ineffective at reducing phospho-tau levels. None of the IgG groups differed compared to the PHF alone samples. Controlled for NeuN levels, these differences remained. The phospho-Tau levels in the PHF alone samples were 1.5 fold higher than that of the untreated control cells (p=0.01). Of the 4E6G7 dosing paradigms, the PHF+Ab and PHF→Ab groups had tau levels comparable to those of untreated controls and significantly lower than those seen in the PHF alone samples (p=0.03 for both). As above, none of the IgG1 groups differed from PHF alone samples.

Example 5

Figure 9:
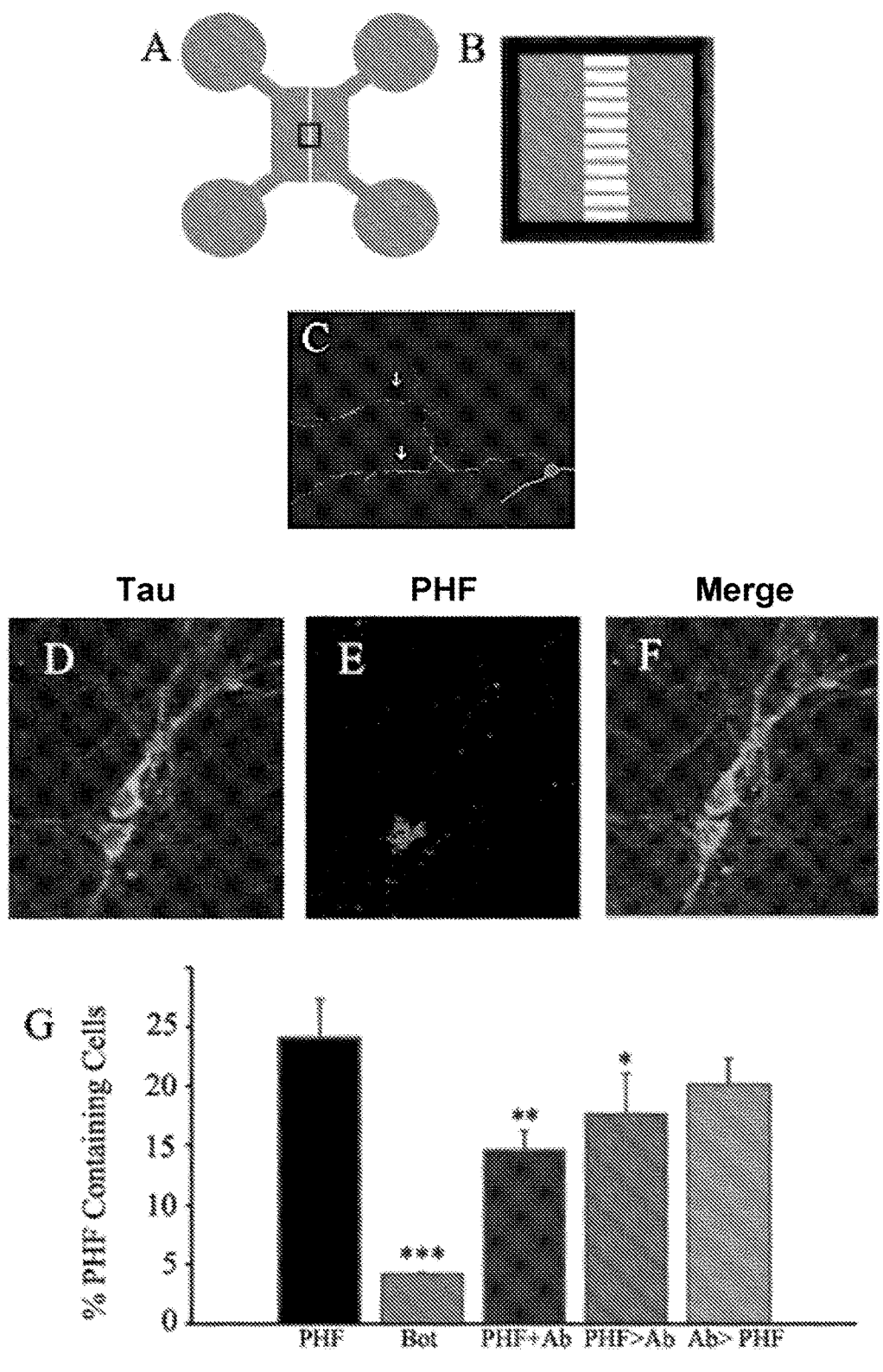
FIG. 9, Panels A-G show that Antibody 4E6G7 can reduce the spread of pathological Tau between cell populations.

Antibody 4E6G7 Can Reduce The Spread Of Pathological Tau Between Cell Populations In order to assess whether treatment with Antibody 4E6G7 could slow the spreading of pathological Tau between cells, JNPL3 and WT neurons were plated on opposite sides of microfluidic axon isolation chambers. FIG. 9, Panel A shows a schematic of the microfluidic chambers, showing the reservoirs that receive the sampled cells. FIG. 9, Panel B is a magnified schematic of the central box in Panel A, showing the microgrooves that connect the two reservoirs. In order to ensure that the axons from JNPL3 cells, but not those of WT cells, crossed through the microgrooves, neurons from JNPL3 mice were plated 72 hours before the WT neurons. After the cell cultures had stabilized, 1 μg/mL of fluorescently labeled PHF material was added to the chamber containing the JNPL3 neurons. Additional cultures were prepared the same way, and treated with a combination of PHF and Antibody 4E6G7 using the PHF+Antibody, PHF→Antibody and Antibody→PHF dosing strategies described above. As a negative control, a further set of cells was incubated with PHF and 50 nM botulinum toxin A. This toxin breaks down SNAP-25/23, a component of synaptic transmission and fusion of multi vesicular bodies (MVBs) with the plasma membrane. Seventy-two hours later, the coverslips were fixed and stained as described above with an antibody recognizing total Tau and the numbers of WT cells containing labeled PHF material was determined (n=969 cells counted). FIG. 9, Panel C is a confocal image showing axons (marked with arrows) growing through the microgrooves. The cell is stained with a pan-Tau antibody. FIG. 9, Panels D-F show fluorescently labeled PHF material (1 μg/mL) that was added to a chamber of the microfluidic device containing JNPL3 cells. FIG. 9, Panel D shows the location of Tau protein. FIG. 9, Panel E shows the location of PHF. FIG. 9, Panel F is a merged image showing both the location of Tau protein and the location of PHF.

In the PHF alone treated cultures, 24±3% of the cells contained fluorescently labeled PHF material. When 50 nM of botulinum toxin was added to PHF treated cultures, this was reduced to 4±0.2% (p=0.0004), indicating that the PHF in the WT cells gets there via synaptic release. PHF+Antibody and PHF→Antibody treatment groups also exhibited reduced numbers of PHF-positive cells (15±2% (p=0.01) and 18±4% (p=0.05), respectively). However, as expected based on other results, there was no significant change in the percentage of PHF-positive cells under Antibody→PHF conditions (FIG. 9, Panel G).

Example 6

Influence of Dosing Method on the Pattern of PHF and Antibody Binding

Figure 10:
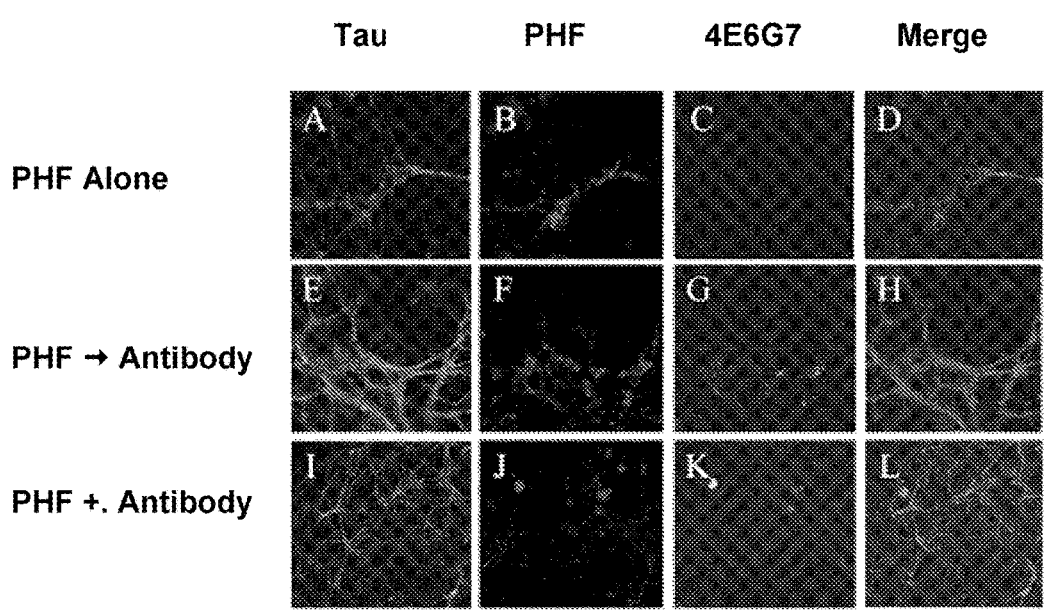
FIG. 10, Panels A-L show the effect of dosing regimen on PHF and antibody binding. Panels A-D show neurons readily take up the PHF-Tau from the media and PHF-positive puncta can be seen in cell bodies and neuronal processes. Panels E-H show the effect of the PHF→Antibody dosing regimen on PHF and antibody binding. Panels I-L show the effect of the PHF+Antibody dosing regimen on PHF and antibody binding. When added together, Antibody 4E6G7 and the PHF material formed large extracellular aggregates.

Fluorescently labeled PHF material and Antibody 4E6G7 were utilized to examine whether the treatment method used affected the pattern of PHF and antibody binding. Primary neurons were incubated with 10 μg/mL PHF or 1 μg/mL Antibody 4E6G7 as follows: PHF alone, PHF+Antibody, PHF=Antibody or Antibody=PHF, as described above. Confocal images were collected 24 h after the last treatment had been applied. All coverslips were stained with Dako pan-Tau polyclonal antibody. PHF was found to have been readily taken up into neurons and could be seen throughout the cells after 24 h in culture (FIG. 10, Panels A-D). In cells from the PHF→Antibody treatment regime, uptake and wide intracellular distribution of PHF material could be seen. Under this dosing regimen, Antibody 4E6G7 was also internalized and co-localized with the previously added PHF (FIG. 10, Panels E-H). However, a different pattern was observed in the PHF+Ab group. Under these conditions, PHF and Antibody 4E6G7 were also seen co-localized, but the PHF-antibody complexes were extracellular (FIG. 10, Panels I-L). These results indicate that although these two dosing methods are effective in reducing pathological changes associated with PHF addition, the mechanism of action differs.

In order to further investigate whether the timing and relative order of antibody and PHF administration affect the mechanism of action, an additional group of cells was plated and dosed as described above. 10 μg/mL PHF was added to JNPL3 neurons, with 4E6G7 added either at the same time or 24 hours later. In additional cultures 1 μg/mL dansylcadaverine (DC), an inhibitor of clathrin mediated endocytosis (Congdon, E. E. et al. (2013) "*Antibody Uptake Into Neurons Occurs Primarily Via Clathrin Dependent Fcgamma Receptor Endocytosis And Is A Prerequisite For Acute Tau Protein Clearance*," J. Biol. Chem. 288(49):35452-35465) was also added along with 4E6G7 in order to determine whether antibody internalization is necessary for 4E6G7 to exert its effects. Thus, these experiments allow confirmation as to whether internalization is required in order to prevent PHF-induced pathology.

Figure 11:
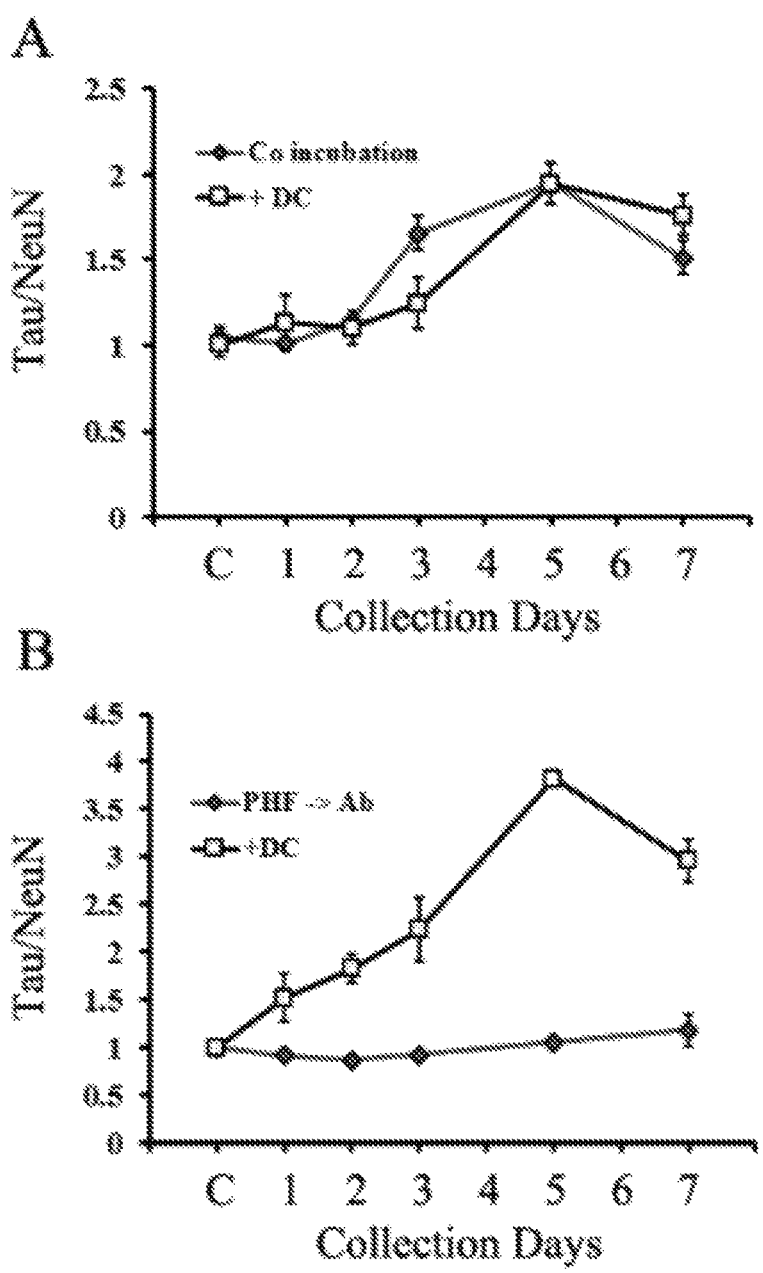
FIG. 11, Panels A-B show that the mechanism of action of Antibody 4E6G7 is influenced by dosing regimen. 10 μg/mL PHF was added to JNPL3 neurons, with Antibody 4E6G7 added either at the same time or 24 hours later. Panel A shows the ratio of Tau/NeuN as a function of the collection day for cells treated using the PHF+Antibody dosing regimen. Panel A shows the ratio of Tau/NeuN as a function of the collection day for cells treated using the PHF→Antibody dosing regimen.

When total Tau levels were examined by immunoblot, no significant difference was observed between samples incubated with or without DC under either dosing conditions. In cells that had been treated with the PHF+Antibody regimen, the addition of DC did not change NeuN levels relative to the Tau/NeuN ratio (FIG. 11, Panel A) or control. However, when cells that had been treated with the PHF→Antibody regimen were incubated with 1 μg/mL DC, a significant decrease in NeuN was observed (reduced to 32% of control compared to cells without DC, p=0.00005). Further, the ratio of Tau/NeuN was significantly shifted in cells that had been treated with the PHF→Antibody regimen where DC had been added (1.18 for cells without DC and 2.95 for DC treated cells, p=0.008; FIG. 11, Panel B). These results indicate that under conditions where Antibody 4E6G7 and PHF are added together, internalization via Fc receptors in unnecessary for the antibody to prevent PHF-induced pathological changes. In contrast, once the PHF material has been taken up by the neurons, preventing antibody internalization blocked its efficacy in preventing PHF toxicity.

Example 7

Prevention of Toxicity and Reduction of Tau Levels by Antibody 4E6G7 and Its Tau-Binding Fragments The data show that Antibody 4E6G7, a monoclonal Tau antibody targeting the $^{\{P\}}$Ser396 and $^{\{P\}}$Ser404 region of Tau protein prevented toxicity and reduced Tau levels induced by the addition of patient-derived PHF material. These findings support the use of Antibody 4E6G7 and its Tau-binding fragments, such as an scFv fragment thereof, in passive Tau immunotherapies.

Alone, addition of 10 or 1 μg/mL PHF-induced cell loss, as measured using LDH and NeuN immunoblotting assays, as well as increased total and phosphorylated Tau in the remaining neurons. It spread between cell populations, through release and subsequent uptake by other neurons. To test the efficacy of Antibody 4E6G7 three different dosing methods were used, differing in the timing of Tau and antibody administration. Two of these methods, addition of the PHF and antibody together, and addition of the antibody 24 h after PHF prevented PHF toxicity and Tau seeding spread. Interestingly, although similarly effective, the mechanism through which the protection occurs differed. With coincubation, extracellular complexes of exogenous PHF and Antibody 4E6G7 formed which neutralized PHF and prevented its uptake. These results support the conclusion that antibodies can be beneficial while working in the interstitial space between cells. In the living brain, these Tau-antibody complexes could then be taken up and cleared by glial cells. When Antibody 4E6G7 was added 24 h after PHF, the two molecules co-localize intracellularly. Antibody 4E6G7 enters the endosomal/lysosomal system and promotes the clearance of native Tau, possibly by promoting disassembly of aggregates (Congdon, E. E. et al. (2013) "*Antibody Uptake Into Neurons Occurs Primarily Via Clathrin-Dependent Fcgamma Receptor Endocytosis And Is A Prerequisite For Acute Tau Protein Clearance*," J. Biol. Chem. 288(49):35452-35465; Gu, J. et al. (2013) "*Two Novel Tau Antibodies Targeting The 396/404 Region Are Primarily Taken Up By Neurons And Reduce Tau Protein Pathology*," J. Biol. Chem. 288(46):33081-33095; Krishnamurthy, P. K. et al. (2011) "*Mechanistic Studies of Antibody-Mediated Clearance of Tau Aggregates Using an ex vivo Brain Slice Model*," Frontiers in Psychiatry/Frontiers Research Foundation 2:59, pages 1-6). This neuronal co-localization between antibody, target, and endosomal/lysosomal markers can also be seen in studies using passive immunotherapy in animal models of Parkinson's disease. Together these findings explain the therapeutic efficacy of Antibody 4E6G7; it is capable of both extracellular blockage of PHF uptake and its intracellular clearance.

In contrast, pre-incubation with Antibody 4E6G7 was significantly less effective at both reducing toxicity and seeding of Tau pathology at the dosage regimens employed. A possible reason for this is the relative lack of the target epitope under these conditions. The levels of Antibody 4E6G7 in neurons correlates with the amount of pathological intracellular Tau. When the antibody is added first, in order to be effective it must be retained in the cell until the addition of the PHF 24 h later. If however, there is a shortage of the target, the antibody will remain unbound, and more prone to degradation or recycling out of the cell. Although Antibody 4E6G7 was ineffective under these conditions, the results presented above do not indicate that it may not be employed in prophylactic therapy for tauopathy, since circulating antibodies could prevent disease initiation by clearing early-stage Tau aggregates. Exogenous antibodies have a half-life of one to three weeks and lower doses could be used in pre-symptomatic individuals at risk.

Example 8

Acute and Long-Term Study of the Efficacy of Antibody 4E6G7 and Its Tau-Binding Fragments The therapeutic efficacy of Antibody 4E6G7 was evaluated using two different mouse models, under acute and long-term treatment conditions. As described below, this rather low affinity antibody provided cognitive benefits after acute and long-term treatment, both of which were associated with clearance of pathological Tau protein. Two models were used, hTau and hTau/PS1 mice: hTau mice (Jackson Laboratories, stock #004808; Andorfer, C. et al. (2003) "*Hyperphosphorylation And Aggregation Of Tau In Mice Expressing Normal Human Tau Isoforms*," J. Neurochem. 86:582-590), express unmutated human Tau protein on a null murine Tau background and develop Tau pathology and tangle with age. This model was used to assess therapeutic benefits of acute passive immunotherapy with Antibody 4E6G7 relative to IgG controls. hTau/PS1 mice were obtained by breeding hTau mice with mice expressing PS1 mutation (M146L; Duff, K. et al. (1996) "*Increased Amyloid-Beta 42(43) In Brains Of Mice Expressing Mutant Presenilin 1*," Nature 383:710-713) and this cross was maintained on a murine Tau KO background. The latter model has accelerated Tau pathology (Boutajangout, A. et al. (2010) "*Immunotherapy Targeting Pathological Tau Prevents Cognitive Decline In A New Tangle Mouse Model*," J. Neurosci. 30:16559-16566). This model was used to assess the benefits of long-term passive immunization with the same antibodies.

A. Behavioral/Cognitive Assessment Methodology

Rotarod: This test is used to measure forelimb and hind limb motor coordination and balance. This procedure was designed to assess motor behavior without a practice confound. Mice were first habituated in four trials to reach a baseline level of performance in first day, and tested in four trails trials next day with 15 min between trials (SDI Rotor-Rod System from San Diego Instruments). Animals were placed on the rod (3.6 cm in diameter) with initial speed set at 1.5 rpm that was then raised every 30 s by 0.5 rpm. A soft foam cushion with plastic cover was placed under the rod to prevent injury from falling. The rod was cleaned with 70% ethanol and then water after each session. In order to assess the performance, the speed of the rod was recorded when the mouse fell or inverted (by clinging) from the top of the rotating barrel.

Locomotor Activity: Mice were first habituated in in a circular open-field activity chamber (55.8 cm in diameter) in group/cage for 15 minutes, and then each mouse was tested individually for 15 min in the same chamber next day. After each session, the field was cleaned with 70% ethanol and then water. A camera above the chamber automatically recorded horizontal movements in each dimension (i.e., x,y) by measuring movement of the animal (EthoVison Video Tracking system from Noldus Information Technology). Results are reported as distance traveled (cm), mean resting time and velocity (average and maximum) of the mouse.

Closed-Field Symmetrical Maze (CFSM): This apparatus is a rectangular field, 65 cm square with 10 cm high walls divided into 36 cm squares and covered by a clear Plexiglas® top. Two boxes, each 16×23×10 cm, were attached to the square at its diagonal corners. The symmetrical maze is a modification of the Hebb-Williams and Rabinovitch-Rosvold types of tests (Pritchett, K. et al. (2004) "*Hebb-Williams Mazes*," Contemp. Top. Lab. Anim. Sci. 43(5):44-45; Meunier, M. et al. (1986) "*The Hebb-Williams Test To Assess Recovery Of Learning After Limbic Lesions In Mice*," Physiol. Behay. 37(6):909-913; Rabinovitch, M. S. et al. (1951) "*A Closed-Field Intelligence Test For Rats*," Can. J. Psychol. 5(3):122-128). Briefly, the main difference is that each end box functions as both a start box and a goal box. The mice run in opposite directions on alternate trials, thereby eliminating inter-trial handling which should minimize stress. The barriers are placed in the field in symmetrical patterns, so that mice face the same turns going in either direction within a given problem. On day 0, mice were adapted to a water-restriction schedule (2 h daily access to water) and habituated in the same environment as was used for testing. On day 1, all mice were given saccharine-flavored water, tinted with green food dye for 10 minutes in each box. On day 2, they were placed in the start box and permitted to explore the field and enter the goal box where saccharine-flavored water reward (0.05 mL) was available. The door to each box was manually opened and closed to allow entry and exit. When the mice were running reliably from the start box to the goal box, they were given four practice trials under the same condition. On day 3, they were given one practice session on a simple problem where two barriers were placed in different symmetrical positions in the field so as to obstruct direct access to the goal box. This practice test was repeated for 4 trials. On day 4, formal testing consisted of three barriers graded for the most difficulty (Boutajangout, A. et al. (2010) "*Immunotherapy Targeting Pathological Tau Prevents Cognitive Decline In A New Tangle Mouse Model*," J. Neurosci. 30:16559-16566; Asuni, A. A. et al. (2006) "*Vaccination Of Alzheimer's Model Mice With Abeta Derivative In Alum Adjuvant Reduces Aβ Burden Without Microhemorrhages*," Eur. J. Neurosci. 24:2530-2542). Mice were given five trials with an inter-trial interval of 2 min. Performance was scored manually by the same observer in terms of errors (i.e., entries and reentries into designated error zones) and time to complete each trial.

In the acute study, mice were then split into control and treatment group which had similar average tests scores and group variance, taking into account as well their performance on the sensorimotor tests. The mice were retested without practice period after treatment.

For the long-term study, mice were only tested at the end of the treatment period and went through three different tests, graded in difficulty (Boutajangout, A. et al. (2010) "*Immunotherapy Targeting Pathological Tau Prevents Cognitive Decline In A New Tangle Mouse Model*," J. Neurosci. 30:16559-16566; Asuni, A. A. et al. (2006) "*Vaccination Of Alzheimer's Model Mice With Abeta Derivative In Alum Adjuvant Reduces Aft Burden Without Microhemorrhages*," Eur. J. Neurosci. 24:2530-2542).

Radial Arm Maze: This test was performed as described by Boutajangout, A. et al. (2012) "*Cognitive And Sensorimotor Tasks For Assessing Functional Impairments In Mouse Models Of Alzheimer's Disease And Related Disorders*," Methods Mol. Biol. 849:529-540. Briefly, the apparatus is an 8-arm elevated radial maze constructed from Plexiglas®. Each arm is 35 cm long and 7 cm wide with a water cup (1 cm in diameter) positioned at the end of each arm. Sidewalls 15 cm high extend 12 cm into each arm to prevent animals from crossing between arms. The central area is an octagonal shaped hub 14 cm in diameter. Clear Plexiglas® guillotine doors, operated remotely by a pulley system control access to the arms. The maze is elevated 75 cm above floor level and situated in a room in which several distinctive objects of a constant location serve as extra maze cues. Prior to testing, mice were adapted for 5 days. During this period, the mice received 0.1% saccharine in water for 1 hour per day and were then adapted 16 hours later to access the sugar solution from a cup placed at the end of each arm. The first two days of adaptation were performed in a Y-maze, which the mice were allowed to explore freely. The subsequent three days of adaptation were performed in the radial arm maze, in which the doors were raised and lowered periodically to accustom the animals to the sound associated with their operation. The same water deprivation schedule was maintained during the 9-day testing period. The mice maintain good health on this schedule. Each testing trial was begun by placing the mouse in the central area and raising all doors. When an arm was entered all doors were lowered. After the mouse consumed the saccharine water, the door to that arm was raised allowing the mouse to return to the central arena. After a 5 sec interval, the next trial was initiated by again raising all of the doors simultaneously. This procedure was continued until the animal had entered all 8 arms or until 10 min has elapsed. Daily acquisition sessions were continued for 9 days. The number of errors (entries to previously visited arms) and time to complete each session were recorded.

Object Recognition Test: This test was performed as described by Boutajangout, A. et al. (2012) "*Cognitive And Sensorimotor Tasks For Assessing Functional Impairments In Mouse Models Of Alzheimer's Disease And Related Disorders*," Methods Mol. Biol. 849:529-540. Briefly, the employed spontaneous object recognition test measures deficits in short term memory, and was conducted in a square-shaped open-field box (48 cm square, with 18 cm high walls constructed from black Plexiglas®), raised 50 cm from the floor. The light intensity was set to 30 lx. On the day before the tests, mice were individually habituated in a session in which they were allowed to explore the empty box for 15 min. During training sessions, two novel objects were placed at diagonal corners in the open-field and the animal was allowed to explore for 15 min. For any given trial, the objects in a pair were 10 cm high, and composed of the same material so that they could not readily be distinguished by olfactory cues. The time spent exploring each object was recorded by a tracking system (San Diego Instruments), and at the end of the training phase, the mouse was removed from the box for the duration of the retention delay (RD=3 h). Normal mice remember a specific object after a delay of 3 h and spend the majority of their time investigating the novel object during the retention trial. During retention tests, the animals were placed back into the same box, in which one of the previous familiar objects used during training was replaced by a novel object, and allowed to explore freely for 6 min. A different object pair was used for each trial for a given animal, and the order of exposure to object pairs as well as the designated sample and novel objects for each pair were counterbalanced within and across groups. The time spent exploring the novel and familiar objects was recorded for the 6 min. The percentage Short Term Memory score is the time spent exploring any one of the two objects (training session) compared to the novel one (retention session).

Fear Conditioning: The test chamber (26 cm×22 cm×18 cm high) had clear Plexiglas® sides and a grid floor that was used to deliver a mild foot shock. The chamber was placed inside a sound-attenuated chamber (internal dimensions: 56 cm×38 cm×36 cm) that had a window through which mice could be observed without disturbance (Coulbourn Habitest from Coulbourn Instrument). On the training day, mice were placed into the test chamber and allowed to explore for 2 min. The conditioned stimulus (CS; a white noise 80 dB sound) was presented for 30 s and followed immediately by a mild foot shock (2 s, 0.7 mA) that served as the unconditioned stimulus (US). After 2 min, the mice received a second CS-US pairing. The Freeze Frame monitor system (San Diego Instruments, San Diego Calif.) was used to control the timing of CS and US presentations and to record freezing behavior. During the conditioning procedure, response to the foot shock (typically runs, jumps, or vocalizations) were also recorded. Mice were tested for contextual fear in 3 h for short term memory and 24 h for long-term memory, during which mice were placed into the original test chamber for 5 min without CS and sound and freezing behavior was recorded.

B. Acute Efficacy Study of Antibody 4E6G7 using hTau Mice

At the start of the hTau Acute efficacy study, the hTau mice were 11-12 months of age and were split into two groups with similar cognitive and motor status prior to receiving three antibody injections and going through retesting on the same behavioral tests in addition to a fear conditioning test, followed by brain extraction for tissue analysis. The mice went through adaptation and pre-tests using Rotorod, Open-Field and Closed-Field Symmetrical Tests on days 1-10 (Boutajangout, A. et al. (2012) "*Cognitive And Sensorimotor Tasks For Assessing Functional Impairments In Mouse Models Of Alzheimer's Disease And Related Disorders*," Methods Mol. Biol. 849:529-540), followed by antibody injection on days 11 and 14 and retesting on days 15-18. A third injection was delivered on day 24 followed by fear conditioning test on days 27-28, and perfusion on day 30.

For the tissue analysis, mice were anesthetized with ketamine/xylazine (250 mg/50 mg per kg body weight, i.p.), and processed as described by Rajamohamedsait, H. B. et al. (2012) "*Histological Staining of Amyloid and Pre-amyloid Peptides and Proteins in Mouse Tissue*," Methods Mol. Biol. 849:411-424. Briefly, the mice were perfused with 25 mL PBS for 10 minutes. The brain was then carefully removed, and the left hemisphere was frozen and stored at $-80°$ C. until processed for Western blots. The right hemisphere was kept in 2% periodate-lysine-paraformaldehyde (PLP) for 24 h, then placed in a DMSO/Glycerol buffer solution for at least another 24 h or until sectioned. Coronal sections (40 µm thick) were obtained on a freezing cryostat, and placed in five series (200 µm apart) into an ethylene glycol cryoprotectant solution and stored at $-30°$ C. until used for immunohistochemistry. Immunostaining was performed with mouse monoclonal Tau antibodies that stain pathological Tau, PHF-1 (1:1000), against the $^{\{P\}}Ser396/^{\{P\}}404$ epitope and MCI (1:100) which recognizes a conformational epitope.

The left hemisphere brain tissue was weighed and homogenized in (5× v/w) modified RIPA buffer (50 mM Tris-HCl, pH 7.4, 150 mM NaCl, 1 mM EDTA, 1 mM NaF, 1 mM $Na_3VO_4$, 1 µg/mL Complete protease inhibitor mixture (Roche Applied Science)). The homogenate was then centrifuged (20,000×g) for 20 min at $20°$ C. and the supernatants were collected as a low speed supernatant (LSS). After protein quantification, the volumes were adjusted for equal protein concentration with dilution in modified O+ buffer (62.5 mM Tris-HCl, pH 6.8, 5% glycerol, 2-mercaptoethanol, 2.3% SDS, 1 mM EGTA, 1 mM phenylmethylsulfonyl fluoride, 1 mM $Na_3VO_4$, 1 µg/mL Complete protease inhibitor, boiled for 5 min, and loaded onto a 12% polyacrylamide gel. For the sarkosyl insoluble fraction, 10% sarkosyl solution was added to the LSS, and the sample was mixed for 30 minutes at room temperature, then centrifuged at 100,000×g for 1 h at $20°$ C. The pellet was then washed in 1% sarkosyl solution and centrifuged again at 100,000×g for 1 h at $20°$ C. The pellet was then air dried for 30 minutes, mixed with 50 µl in modified O+ buffer, vortexed for 1 min, then boiled for 5 min and denoted the "sarkosyl pellet (SP) fraction."

Figure 12:
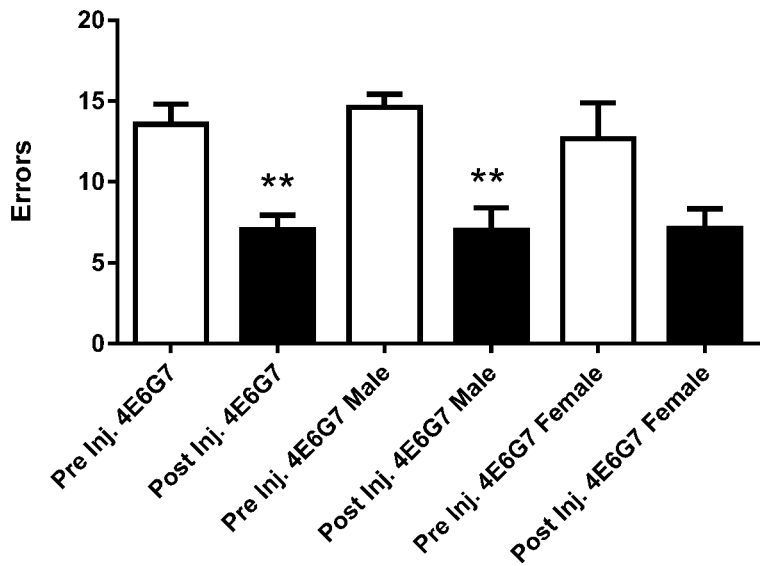
FIG. 12, Panels A-B show that hTau mice that had been immunized with Antibody 4E6G7 exhibited significant improvements in the Closed-Field Symmetrical Maze (CFSM) test (p<0.01) (FIG. 12, Panel A), whereas the control mice did not (FIG. 12, Panel B).
Figure 12:
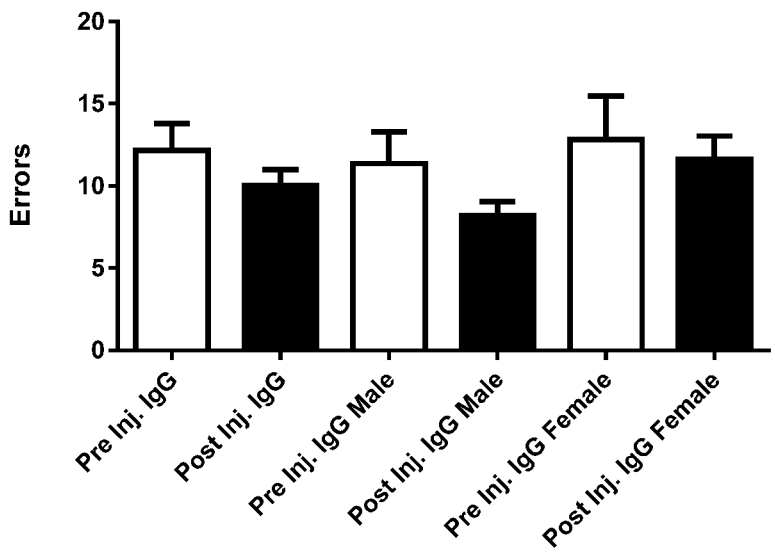

As shown by trial errors, hTau mice that had been immunized with Antibody 4E6G7 exhibited significant improvements in the CFSM test ($p<0.01$) (FIG. 12, Panel A), whereas the control mice did not (FIG. 12, Panel B). Both groups of mice performed similarly in motor function tests (rotor-rod and open-field tests), suggesting the improvements in cognitive functions were direct results of the immunization, but not secondary effects from motor function changes. However, both immunized and control mice failed to show any improvements in fear conditioning tests after treatment.

C. Long-Term Efficacy Study of Antibody 4E6G7 using hTau/PS1 Mice

Immunizations started when the mice were 8-9 months of age and continued weekly for thirteen weeks. In the month prior to sacrifice, the mice went through a battery of cognitive tests (Radial Arm Maze, Closed-Field Symmetrical Tests of varying difficulties, and Object Recognition test, as described above), as well as sensorimotor tests (Rotorod and Open-Field, as described above) to verify that such deficits were not a confounding variable in the cognitive assessment.

Figure 13:
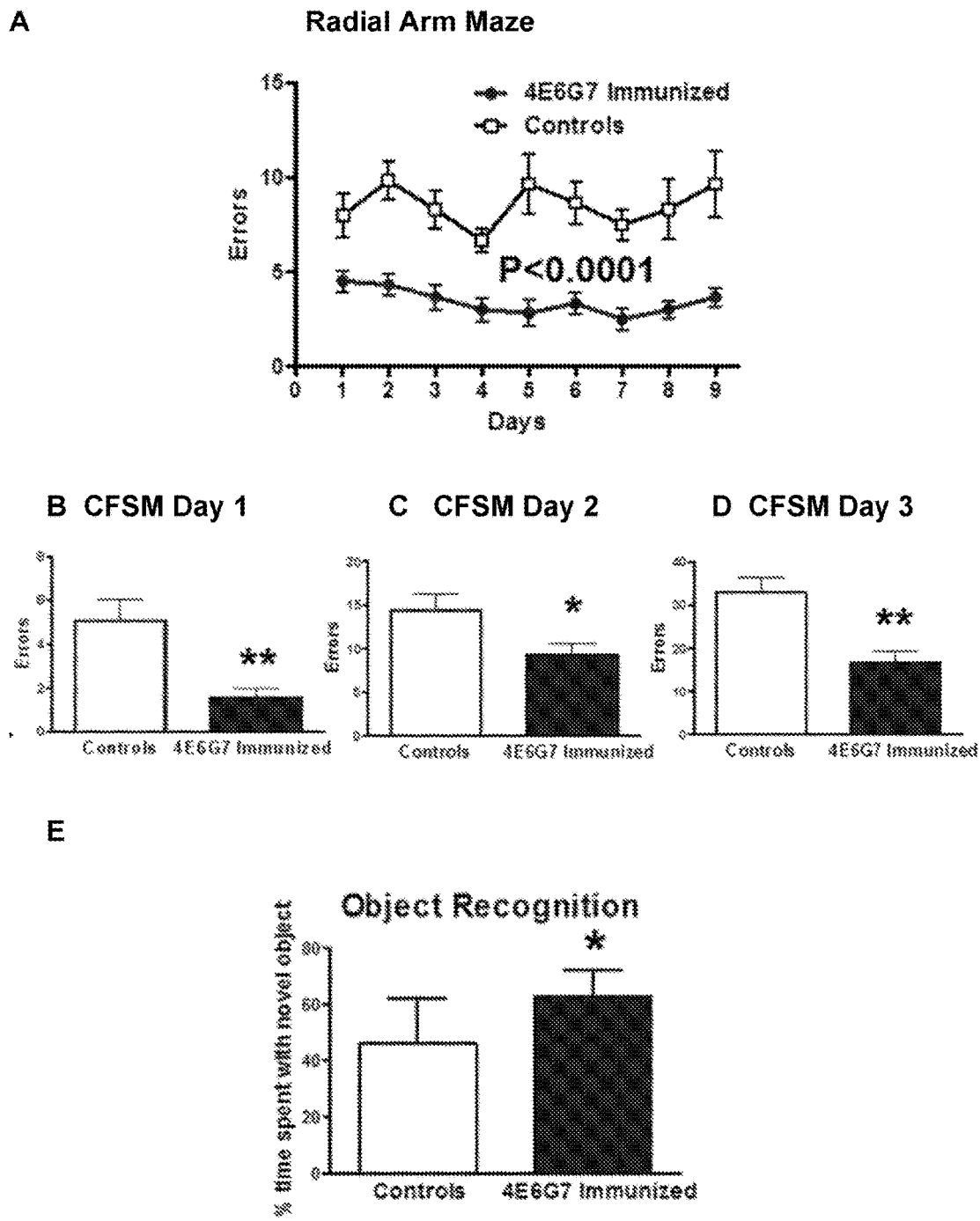
FIG. 13, Panels A-E show that hTau/PS1 mice immunized with Antibody 4E6G7 performed substantially better than control mice on the Radial Arm Maze (Panel A), in the Closed-Field Symmetrical Maze (Panel B (Day 1), Panel C (Day 2) and Panel D (Day 3) and in the Object Recognition Test (Panel E).

The immunized mice were found to perform substantially better than control mice on the Radial Arm Maze ($p<0.0001$; post-hoc, $p<0.01$-$0.001$ on days 2, 3, 5-9) (FIG. 13, Panel A), the CFSM with 35-69% fewer errors in simple, intermediate and complex tasks ($p<0.05$-$0.003$) (FIG. 13, Panels B-D), and the Object Recognition Task (63% time spent with a novel object vs. 46% for controls, $p<0.05$; FIG. 13, Panels E). The groups did not differ in various sensorimotor tasks, indicating that the robust cognitive improvements cannot be explained by sensorimotor effects, which further strengthens the results.

Figure 14:
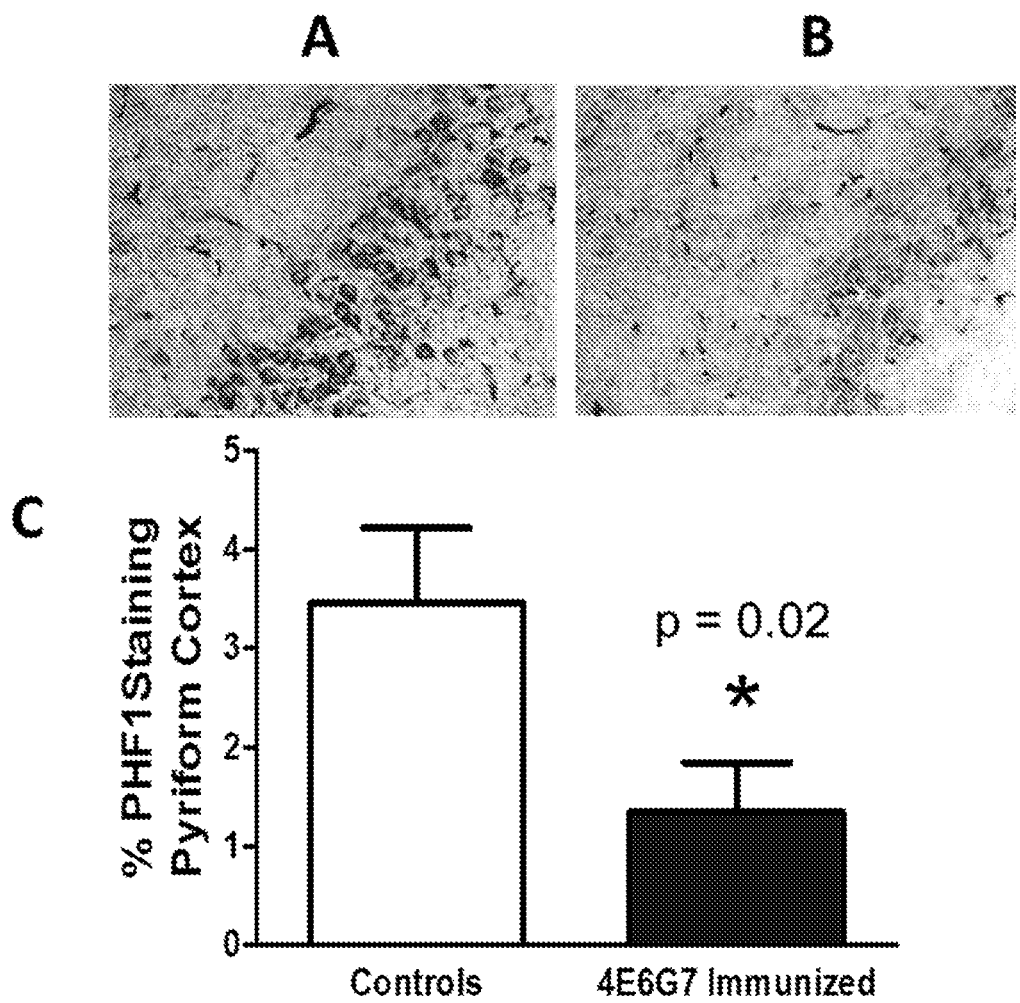
FIG. 14, Panels A-C show PHF-1-stained brain sections for control mice (FIG. 14, Panel A) and hTau/PS1 mice immunized with Antibody 4E6G7 (FIG. 14, Panel B).

Immunohistochemistry was performed as described in the Acute Efficacy Study. Quantitative analysis of PHF-1-stained brain sections revealed 61% reduction in pathological Tau in the pyriform cortex in the immunized mice, compared to IgG injected controls. FIG. 14, Panels A-C show PHF-1-stained brain sections for control mice (FIG. 14, Panel A) and hTau/PS1 mice immunized with Antibody 4E6G7 (FIG. 14, Panel B). FIG. 14, Panel C shows a quantitative analysis of the PHF-1 staining of brain cells of control and immunized mice.

Example 9

Antibody 4E6G7 Exhibits Properties that Are Not Observed with Other Antibodies Directed to the $^{\{p\}}$Ser404 Epitope of Tau In order to further demonstrate the novel characteristics of Antibody 4E6G7, its characteristics were compared with those of a control anti-Tau antibody (Antibody 6B2G12; also designated as Antibody 6B2) that had also been raised against the $^{\{p\}}$Ser404 Epitope of Tau (Krishnaswamy, S. et al. (2014) "*Antibody-Derived in vivo Imaging of Tau Pathology,*" J. Neurosci. 34(50):16835-16850); Congdon, E. E., et al. (2013) "*Antibody Uptake Into Neurons Occurs Primarily Via Clathrin-Dependent Fcgamma Receptor Endocytosis And Is A Prerequisite For Acute Tau Protein Clearance,*" J. Biol. Chem. 288(49):35452-35465; Gu, J. et al. (2013) "*Two Novel Tau Antibodies Targeting The 396/404 Region Are Primarily Taken Up By Neurons And Reduce Tau Protein Pathology,*" J. Biol. Chem. 288(46):33081-33095). Both Antibody 4E6G7 and Antibody 6B2G12 are capable of entering neurons and co-localizing with tau (Gu, J. et al. (2013) "*Two Novel Tau Antibodies Targeting The 396/404 Region Are Primarily Taken Up By Neurons And Reduce Tau Protein Pathology,*" J. Biol. Chem. 288(46):33081-33095).

In brain slice cultures, both antibodies reduce soluble phospho-tau after 6 weeks of treatment. However, despite having been elicited against the same epitope, the two antibodies display multiple different functional characteristics. However, only Antibody 4E6G7 and not Antibody 6B2G12, is found to acutely reduce tau levels in primary neurons via an intracellular mechanism (Congdon, E. E., et al. (2013) "*Antibody Uptake Into Neurons Occurs Primarily Via Clathrin-Dependent Fcgamma Receptor Endocytosis And Is A Prerequisite For Acute Tau Protein Clearance,*" J. Biol. Chem. 288(49):35452-35465; Gu, J. et al. (2013) "*Two Novel Tau Antibodies Targeting The 396/404 Region Are Primarily Taken Up By Neurons And Reduce Tau Protein Pathology,*" J. Biol. Chem. 288(46):33081-33095). The two antibodies display different binding characteristics with Antibody 4E6G7 being phospho-selective and Antibody 6B2G12 having conformational properties influenced by phosphorylation and an apparent higher affinity for tau (Gu, J. et al. (2013) "*Two Novel Tau Antibodies Targeting The 396/404 Region Are Primarily Taken Up By Neurons And Reduce Tau Protein Pathology,*" J. Biol. Chem. 288(46): 33081-33095).

Figure 15:
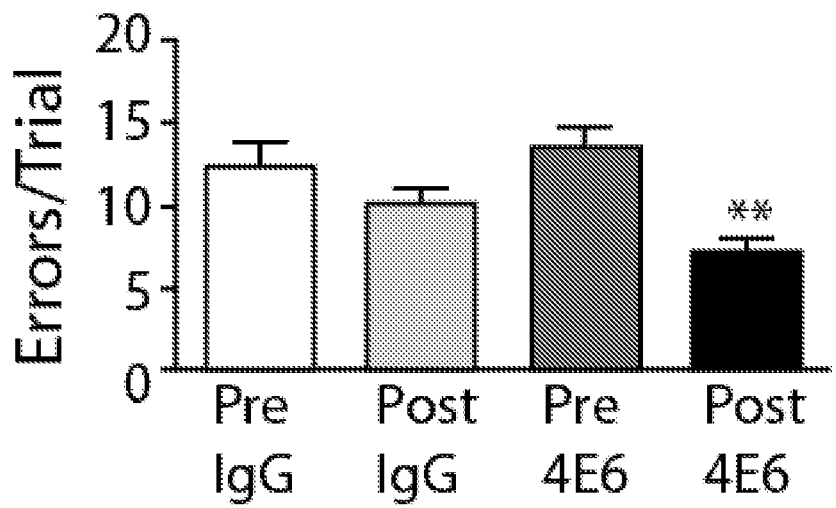
FIG. 15, Panels A-B show that Antibody 4E6G7-immunized mice (Panel A) exhibited significant improvements in Closed Field Symmetrical (CFS) Maze (48% fewer errors, p<0.01), compared to their pre-immunization performance, whereas control IgG treated mice did not improve. When divided by gender, both males and females treated with Antibody 4E6G7 showed significant improvement over their pre-treatment performance (52% and 44% fewer errors, p<0.01 and p<0.05, respectively, see text for average and SEM). Repeated measures, two-way ANOVA revealed a significant effect of treatment (p=0.0018) but not of gender (p=0.5145), indicating that the results seen are not attributable to gender differences. In contrast, animals treated with IgG did not show improvement when all animals were considered together, or when divided by gender. Panel B shows Antibody 6B2G12-immunized mice did not improve in the same test. **: p<0.01.
Figure 15:
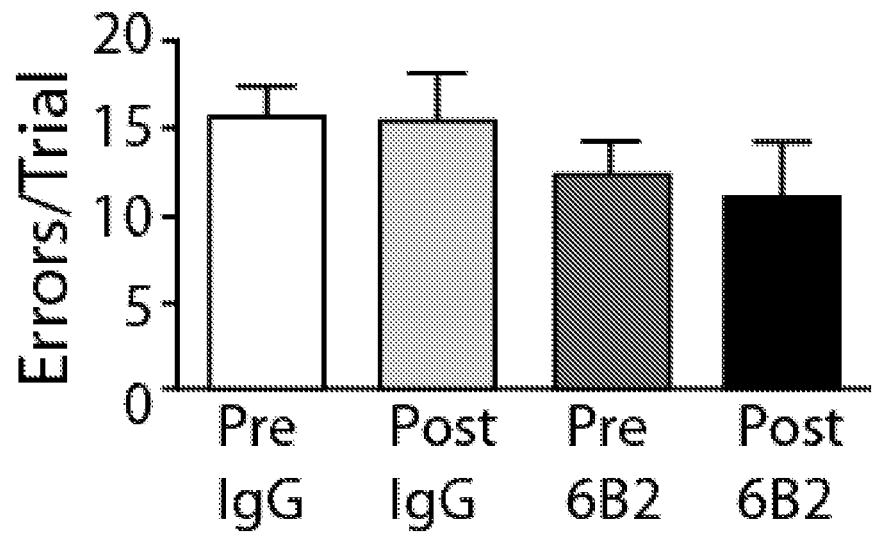

Antibody 4E6G7, but not Antibody 6B2G12, acutely improves cognition in hTau mice and reduces soluble phospho-Tau protein. As shown by trial errors, acute treatment of hTau mice with Antibody 4E6G7 led to significant improvements in cognition, spatial learning and memory as determined in the CFSM test (48% fewer errors in post-test vs. pre-test; 13.6 (average errors)±1.2 (SEM) to 7.1±0.9, $p<0.01$), whereas the IgG control mice did not improve compared to their pre-injection performance (FIG. 15, Panel A) These differences were not gender related. Antibody 4E6G7-treated males (52% fewer errors; 14.6±0.8 to 7.0±1.4, $p<0.01$) performed similar to Antibody 4E6G7-treated females (44% fewer errors; 12.7±2.2 to 7.1±1.2, $p<0.05$). Repeated measures, two-way ANOVA revealed a treatment effect ($p=0.0018$), but not a gender effect ($p=0.5145$). Conversely, Antibody 6B2G12 treatment did not result in improvements in this test (FIG. 15, Panel B).

Additional differences in the properties of these antibodies were also identified. As indicated above, incubation with AD-derived PHF at 1 μg/mL or at 10 μg/mL was found to induce toxicity in primary neurons as determined by LDH assay (see e.g., FIGS. 1-2) and NeuN immunoblotting (see e.g., FIGS. 3-4), and Antibody 4E6G7 was found to prevent these effects; however, Antibody 6B2G12 was found to be unable prevent these effects. Similarly, treatment with Antibody 4E6G7 (at 10 μg/mL or 1 μg/mL) was found to prevent changes in tau levels caused by PHF exposure (see, e.g., FIGS. 5-6), whereas treatment with Antibody 6B2G12 was found to have no effect. Additionally, Antibody 4E6G7 was found to be able to prevent the increase in phosphorylated Tau that is triggered by exposure to 1 μg/mL or 10 μg/mL PHF see, e.g., FIGS. 7-8); Antibody 6B2G12 was found to be unable to prevent such an increase.

Neither antibody showed benefits in a fear conditioning test. Both treatment groups of mice performed similarly to IgG controls in motor function tests (rotor rod and open field tests), suggesting that the Antibody 4E6G7-mediated improvements in cognitive functions were direct results of the immunization, but not secondary effects from motor function changes.

Example 10

Antibody 4E6G7 Recognizes Primarily Solubilized PHF

In order to further examine the basis for the differing properties of Antibody 4E6G7 and Antibody 6B2G12, binding of the antibodies to tau peptides, solubilized PHF and other tau fractions, was characterized in BIACORE™, dot blot and ELISA assays.

BIACORE™ Assay

The binding of Antibody 4E6G7 and Antibody 6B2G12 to tau peptides corresponding to the 396/404 region of the tau protein was examined using a biacore assay. Neither antibody showed binding to the P-Ser396 which differs from previously published ELISA assays (Gu, J. et al. (2013) "*Two Novel Tau Antibodies Targeting The 396/404 Region Are Primarily Taken Up By Neurons And Reduce Tau Protein Pathology*," J. Biol. Chem. 288(46):33081-33095). However, for all other epitope peptides, Antibody 6B2G12 yielded $K_D$ values substantially lower ($10^{-9}$-$10^{-10}$ M) than those seen with Antibody 4E6G7 ($10^{-7}$ M), indicating much higher affinity for the immunogen epitope (Table 5). Using ELISA, Antibody 4E6G7 was found to bind very poorly to the P-Ser396 peptide coated onto the plate, however, Antibody 6B2G12 did show binding. This may be due to conformational changes which occur in the peptide when binding to the plate, or differences that occur when the antibody is immobilized. We observed similar lack of binding of Antibody 4E6G7 and Antibody 6B2G12 to the P-Ser396 peptide in solution in competition ELISAs, confirming the accuracy of the BIACORE™ data. These findings emphasize that a variety of methods should be used when assessing antibody affinity.

TABLE 5

| $K_D$ (Biacore) | Antibody 4E6G7 | Antibody 6B2G12 |
|---|---|---|
| 30 Amino Acid Peptides | | |
| Tau379-408 [P-Ser396/404] | $2.71 \times 10^{-7}$ | $3.95 \times 10^{-10}$ |
| Tau379-408 | $2.12 \times 10^{-7}$ | $2.51 \times 10^{-9}$ |
| 23 Amino Acid Peptides | | |
| Tau386-408 [P-Ser396/404] | $4.69 \times 10^{-7}$ | $2.39 \times 10^{-9}$ |
| Tau386-408 [P-Ser404] | $2.78 \times 10^{-7}$ | $4.11 \times 10^{-9}$ |
| Tau386-408 [P-Ser396] | ND | ND |

Dot Blot Assay

Binding of Antibody 4E6G7 and Antibody 6B2G12 to PHF was assayed using a dot blot of different tau fractions (FIG. 1, FIG. 16, Panel A). The solubilized PHF-, sarkosyl soluble- and sarkosyl insoluble fractions from the same human AD brain were applied to nitrocellulose membrane, which was then incubated with Antibody 4E6G7 or Antibody 6B2G12 (FIG. 16, Panel A). Antibody 4E6G7 had higher affinity for solubilized PHF but Antibody 6B2G12 bound better to the sarkosyl insoluble fraction. Neither antibody bound well to the sarkosyl soluble fraction. Both Antibody 4E6G7 and Antibody 6B2G12 showed limited binding to control samples using dot blot (FIG. 16, Panel B). No visible reactivity was seen in the sarkosyl soluble fraction, and only minimal reactivity in the other two fractions. Note that the control tissue had very limited if any pathological tau and the pelletable material was much less than in the AD tissue and likely contains various proteins. Same amount of protein was blotted for AD and control tissue.

ELISA Assays

Two different ELISA assays were performed to assess binding of Antibody 4E6G7 and Antibody 6B2G12 to different tau fractions from AD and control brain. In the first, the plate was coated with material from either the sarkosyl soluble, solubilized PHF or sarkosyl insoluble fractions (1 µg/well) and dilutions of antibody were added.

When plates were coated with the solubilized PHF (FIG. 16, Panel C), Antibody 6B2G12 showed significantly higher binding to wells coated with material from AD brain than control for all dilutions up to $\frac{1}{125}$ k (p<0.0001-0.05) and significantly higher binding that Antibody 4E6G7 to either AD or control at $\frac{1}{200}$-$\frac{1}{5}$ k (p<0.0001). In contrast, Antibody 4E6G7 did not show significantly higher binding to AD tau versus control tau at any of the dilutions.

In plates coated with sarkosyl soluble tau (FIG. 16, Panel D), low binding was detected even at the highest antibody concentrations. At the $\frac{1}{200}$ dilution, Antibody 6B2G12 showed significantly higher binding to AD tau than tau from control brain, and also higher binding than Antibody 4E6G7 to either AD or control tau (p<0.01, 0.05 and 0.05 respectively). None of the other dilutions or conditions showed any significant differences between samples.

Finally, when the plates were coated with the sarkosyl insoluble tau (FIG. 16, Panel E), Antibody 6B2G12 showed significantly higher binding than Antibody 4E6G7 to AD tau at the $\frac{1}{200}$-$\frac{1}{125}$ k dilutions (p<0.0001-0.05) and also significantly higher binding to AD tau at the same dilutions (p<0.0001-0.05). Again, there was no significant difference in binding to AD versus control with Antibody 4E6G7.

A competition ELISA was then performed to determine antibody binding to PHF in solution. In this assay, plates were coated with solubilized PHF as described above, but before antibodies were added aliquots were incubated for 1 hour with increasing concentrations of solubilized PHF (0.01-1 µg/ml). Under these conditions, binding to solubilized PHF markedly inhibited binding of Antibody 4E6G7 to the PHF coated onto the plate, but Antibody 6B2G12 binding was not affected. At the highest PHF concentration, Antibody 4E6G7 binding to the wells was reduced by 85%. The IC50 value was determined to be 71 nM (FIG. 16, Panel F). In contrast, Antibody 6B2G12 did not show reduced binding to the wells at any PHF concentration. These data indicate that the two antibodies are binding to different tau species within the AD-derived PHF material; Antibody 4E6G7 to solubilized PHF and Antibody 6B2G12 to aggregated PHF.

The ELISA and dot blot binding data, particularly when considered with the findings from confocal and biochemical analyses, suggests that efficacy of Antibody 4E6G7 (and the lack thereof for Antibody 6B2G12) may be explained by their respective degree of interaction/neutralization of PHF. Dot blot assay and ELISA data show that although both Antibody 4E6G7 and Antibody 6B2G12 bind to PHF, the affinity and preferred species differs, with Antibody 6B2G12 potentially binding to a more highly aggregated but less toxic tau form (FIG. 16, Panel A).

In contrast to results obtained with Antibody 6B2G12, in all assays, Antibody 4E6G7 showed less binding to aggregated tau and preferential binding to solubilized PHF. Despite strong binding to the solubilized PHF fraction on dot blots relative to control samples, in ELISA assays, Antibody 4E6G7 showed a limited ability to bind to tau that was aggregated onto the wells. Ab-PHF complexes are not seen with the co-incubation of Antibody 6B2G12 and PHF because the latter is in its solubilized form in the culture media which does not bind Antibody 6B2G12 (FIG. 16, Panel F). (The solubility of the PHF fraction under experimental concentrations was confirmed using ultra-centrifugation.) pH changes in endosomes/lysosomes may promote aggregation, resulting in a mixture of soluble and insoluble forms of PHF and, therefore, binding of both antibodies in these vesicles (the PHF→Ab condition). However, only binding of Antibody 4E6G7 to the solubilized PHF form is beneficial, whereas binding by Antibody 6B2G12 has no effect. This detailed clarification has major implications for the development of tau immunotherapies and for understanding the pathogenesis of tauopathies, for it indicates that therapeutic efficacy is associated with an ability to bind to soluble (or solubilized) PHF.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An antibody-based molecule that is capable of immunospecifically binding to the $^{\{p\}}$Ser404 Epitope of Tau, wherein said $^{\{p\}}$Ser404 Epitope is present on a peptide having the sequence of Tau 386-408 ($^{\{p\}}$Ser396/$^{\{p\}}$Ser404) (SEQ ID NO:8):

TDHGAEIVYK$^{\{P\}}$SPVVSGDT$^{\{P\}}$SPRHL wherein the residues at positions 11 and 19 thereof are phosphoserine, wherein said antibody-based molecule is additionally capable of binding to phosphorylated Tau with greater selectivity than to non-phosphorylated Tau, and wherein said antibody-based molecule comprises:
(a) a Light Chain CDR1 comprising the amino acid sequence of SEQ ID NO:10;
(b) a Light Chain CDR2 comprising the amino acid sequence of SEQ ID NO:11;
(c) a Light Chain CDR3 comprising the amino acid sequence of SEQ ID NO:12;
(d) a Heavy Chain CDR1 comprising the amino acid sequence of SEQ ID NO:14;
(e) a Heavy Chain CDR2 comprising the amino acid sequence of SEQ ID NO:15; and
(f) a Heavy Chain CDR3 comprising the amino acid sequence of SEQ ID NO:16.

2. The antibody-based molecule of claim 1, wherein said molecule binds to solubilized PHF.

3. The antibody-based molecule of claim 1, wherein said molecule is an antibody that binds said $^{\{p\}}$Ser404 Epitope of Tau, or comprises a $^{\{p\}}$Ser404 Epitope-binding fragment of an antibody.

4. The antibody-based molecule of claim 3, wherein said molecule comprises a $^{\{p\}}$Ser404 Epitope-binding fragment of an antibody and is a single domain antibody fragment, an immunoglobulin Light Chain Variable Domain and an immunoglobulin Heavy Chain Variable Domain, an scFv or a diabody.

5. The antibody-based molecule of claim 3, wherein said molecule is an antibody that binds said $^{\{p\}}$Ser404 Epitope of Tau.

6. The antibody-based molecule of claim 3, wherein said molecule is a fragment of an antibody, wherein said fragment binds said $^{\{p\}}$Ser404 Epitope of Tau.

7. The antibody-based molecule of claim 1, wherein said molecule is a humanized antibody or comprises an epitope-binding fragment of a humanized antibody.

8. The antibody-based molecule according to claim 1, wherein said molecule is an antibody that binds said $^{\{p\}}$Ser404 Epitope of Tau, or comprises a $^{\{p\}}$Ser404 Epitope-binding fragment thereof that, upon peripheral injection into a recipient, substantially co-localizes with a Tau aggregate.

9. The antibody-based molecule of claim 1, wherein said antibody-based molecule is an antibody that binds said $^{\{p\}}$Ser404 Epitope of Tau, or a $^{\{p\}}$Ser404 Epitope-binding fragment thereof, that comprises a Variable Light Chain Domain having the amino acid sequence of SEQ ID NO:9 and/or a Variable Heavy Chain Domain having the amino acid sequence of SEQ ID NO:13.

10. The antibody-based molecule of claim 9, wherein said molecule is an scFv that comprises the amino acid sequence of SEQ ID NO:17.

11. The antibody-based molecule of claim 1, which is detectably labeled.

12. The antibody-based molecule of claim 11, wherein said detectable label is a fluorescent label, a chemoluminescent label, a paramagnetic label, a radioisotopic label or an enzyme label.

13. A method for detecting or measuring the presence or amount of phosphorylated Tau protein in the brain, cerebrospinal fluid, blood, serum or plasma of a recipient subject, which comprises administering the detectably-labeled antibody-based molecule of claim 11 to said recipient subject and detecting or measuring binding between said molecule and said phosphorylated Tau.

14. The method of claim 13, wherein said detection or measurement comprises in vivo or ex vivo imaging of said antibody-based molecule bound to said phosphorylated Tau protein.

15. The method of claim 13, wherein said detected or measured binding is diagnostic of Alzheimer's disease or another tauopathy in said subject.

16. The method of claim 13, wherein said subject is a human.

17. The method of claim 15, wherein said method is diagnostic of a tauopathy selected from the group consisting of: frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

18. A pharmaceutical composition which comprises:
(a) the antibody-based molecule of claim 1 in an amount effective to treat said Alzheimer's disease or other tauopathy, and
(b) one or more carriers, diluents and/or stabilizers.

19. A method for treating Alzheimer's disease or another tauopathy of a subject, which comprises administering an effective amount of the pharmaceutical composition of claim 18 to said subject.

20. The method of claim 19, wherein said subject is a human.

21. The method of claim 19, wherein said method treats a tauopathy selected from the group consisting of: fronto-temporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

\* \* \* \* \*